(12) United States Patent
Khanzhin et al.

(10) Patent No.: US 7,906,537 B2
(45) Date of Patent: Mar. 15, 2011

(54) SUBSTITUTED P-DIAMINOBENZENE DERIVATIVES

(75) Inventors: Nikolay Khanzhin, Frederiksberg (DK); Mario Rottlander, Greve (DK); Andreas Ritzen, Vanlose (DK); William P. Watson, Vanlose (DK)

(73) Assignee: H. Lundbeck A/S, Valby-Copenhagen (DK)

( * ) Notice: Subject to any disclaimer, the term of this patent is extended or adjusted under 35 U.S.C. 154(b) by 508 days.

(21) Appl. No.: 10/550,448

(22) PCT Filed: Mar. 18, 2004

(86) PCT No.: PCT/DK2004/000186
§ 371 (c)(1),
(2), (4) Date: Nov. 16, 2005

(87) PCT Pub. No.: WO2004/082677
PCT Pub. Date: Sep. 30, 2004

(65) Prior Publication Data
US 2006/0183791 A1 Aug. 17, 2006

Related U.S. Application Data

(60) Provisional application No. 60/456,698, filed on Mar. 21, 2003.

(30) Foreign Application Priority Data

Mar. 21, 2003 (DK) .................................. 200300441

(51) Int. Cl.
*A61K 31/44* (2006.01)
*C07D 213/643* (2006.01)
*C07D 213/00* (2006.01)

(52) U.S. Cl. ........................................ 514/357; 546/329
(58) Field of Classification Search ................... 514/357; 546/329
See application file for complete search history.

(56) References Cited

U.S. PATENT DOCUMENTS

| 5,384,330 | A | | 1/1995 | Dieter et al. | |
|---|---|---|---|---|---|
| 6,071,968 | A | | 6/2000 | Nishino et al. | |
| 6,498,275 | B1 | * | 12/2002 | Butlin et al. | 564/202 |
| 2004/0087798 | A1 | * | 5/2004 | Yamada | 546/336 |

FOREIGN PATENT DOCUMENTS

| EP | 554543 B1 | 2/1996 |
|---|---|---|
| EP | 1 264 820 A1 | 12/2002 |
| JP | 2-196769 | 8/1990 |
| JP | 02196769 A | 8/1990 |
| JP | 05163223 A | 6/1993 |
| JP | 2001071637 A | 3/2001 |
| JP | 2004-75648 | 3/2004 |
| JP | 2004075648 A | 3/2004 |
| WO | WO-92/13828 A1 | 8/1992 |
| WO | WO 99/62506 * | 12/1999 |
| WO | 0107020 A2 | 2/2001 |
| WO | WO-01/07020 | 2/2001 |
| WO | WO-01/07020 A2 | 2/2001 |
| WO | WO 01/68585 A1 * | 9/2001 |
| WO | WO-02/49628 A1 | 6/2002 |
| WO | 03016266 A1 | 2/2003 |

OTHER PUBLICATIONS

Patani et al. "Bioisosterism: A Rational Approach in Drug Design" Chemical Reviews, 1996, vol. 96, pp. 3147-3176.*
Grehn, L., et al., "Selective cathodic cleavage of protected, mixed primary-secondary amines", J. Chem Research, Synopses (1991), (6), pp. 144-145, abstract (HCAplus; Acc.No. 1991:480775).
Martinelli, J.E., et al., "Methotrexate analogs. 12. Synthesis and biological properties of some aza homologs", J. Med. Chem. (1979), 22(7), pp. 869-874, abstract (HCAplus; Acc.No. 1979:483166).
Kimiatsu Nomura et al., "Heat-Developable diazo recording material", JP 2001 071637 Mar. 21, 2001, Fuji Photo Film Co., Abstract.
Martin J. Main et al., "Modulation of KCNQ2/3 Potassium Channels by the Novel Anticonvulsant Retigabine", Molecular Pharmacology, vol. 58, No. 2, Aug. 2000, pp. 253-262.
Scott, et al., "A medium-throughout functional assay of KCNQ2 potassium channel using rubidium efflux and atomic absorption . . .", Analytical Biochemistry, 2003, 3. 1-7.

* cited by examiner

*Primary Examiner* — Joseph R Kosack

(57) ABSTRACT

The present invention relates to aniline derivatives of the general formula I or pharmaceutically acceptable salts thereof and their use.

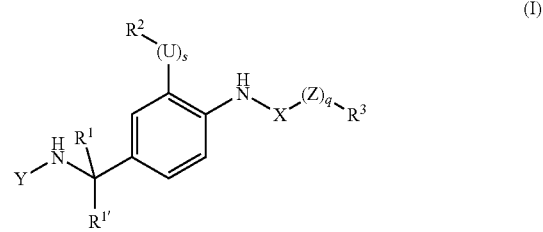

(I)

19 Claims, No Drawings

US 7,906,537 B2

SUBSTITUTED P-DIAMINOBENZENE DERIVATIVES

This application is a §371 national stage of International Application No. PCT/DK2004/000186, filed Mar. 18, 2004, which was published in English as International Publication No. WO 2004/082677, and claims the benefit of priority of U.S. Provisional Application No. 60/456,698, filed Mar. 21, 2003 and Danish Patent Application No. PA 200300441, filed Mar. 21, 2003.

FIELD OF THE INVENTION

The present invention relates to novel substituted p-diaminobenzene derivatives being openers of the KCNQ family potassium ion channels. The compounds are useful for the prevention, treatment and inhibition of disorders and diseases being responsive to opening of the KCNQ family potassium ion channels, one such disease is epilepsy.

BACKGROUND OF THE INVENTION

Ion channels are cellular proteins that regulate the flow of ions, including potassium, calcium, chloride and sodium into and out of cells. Such channels are present in all animal and human cells and affect a variety of processes including neuronal transmission, muscle contraction, and cellular secretion.

Humans have over 70 genes encoding potassium channel subunits (Jentsch *Nature Reviews Neuroscience* 2000, 1, 21-30) with a great diversity with regard to both structure and function. Neuronal potassium channels, which are found in the brain, are primarily responsible for maintaining a negative resting membrane potential, as well as controlling membrane repolarisation following an action potential.

One subset of potassium channel genes is the KCNQ family. Mutations in four out of five KCNQ genes have been shown to underlie diseases including cardiac arrhythmias, deafness and epilepsy (Jentsch *Nature Reviews Neuroscience* 2000, 1, 21-30).

The KCNQ4 gene is thought to encode the molecular correlate of potassium channels found in outer hair cells of the cochlea and in Type I hair cells of the vestibular apparatus, in which mutations can lead to a form of inherited deafness.

KCNQ1 (KvLQT1) is co-assembled with the product of the KCNE1 (minimal K(+)-channel protein) gene in the heart to form a cardiac-delayed rectifier-like K(+) current. Mutations in this channel can cause one form of inherited long QT syndrome type 1 (LQT1), as well as being associated with a form of deafness (Robbins *Pharmacol Ther* 2001, 90, 1-19).

The genes KCNQ2 and KCNQ3 were discovered in 1988 and appear to be mutated in an inherited form of epilepsy known as benign familial neonatal convulsions (Rogawski *Trends in Neurosciences* 2000, 23, 393-398). The proteins encoded by the KCNQ2 and KCNQ3 genes are localised in the pyramidal neurons of the human cortex and hippocampus, regions of the brain associated with seizure generation and propagation (Cooper et al. *Proceedings National Academy of Science USA* 2000, 97, 4914-4919).

KCNQ2 and KCNQ3 are two potassium channel subunits that form "M-currents" when expressed in vitro. The M-current is a non-inactivating potassium current found in many neuronal cell types. In each cell type, it is dominant in controlling membrane excitability by being the only sustained current in the range of action potential initiation (Marrion *Annual Review Physiology* 1997, 59, 483-504). Modulation of the M-current has dramatic effects on neuronal excitability, for example activation of the current will reduce neuronal excitability. Openers of these KCNQ channels, or activators of the M-current, will reduce excessive neuronal activity and may thus be of use in the treatment, prevention or inhibition of seizures and other diseases and disorders characterised by excessive neuronal activity, such as neuronal hyperexcitability including convulsive disorders, epilepsy and neuropathic pain.

Retigabine (D-23129; N-(2-amino-4-(4-fluorobenzylamino)-phenyl)carbamic acid ethyl ester) and analogues thereof are disclosed in EP554543. Retigabine is an anti-convulsive compound with a broad spectrum and potent anticonvulsant properties, both in vitro and in vivo. It is active after oral and intraperitoneal administration in rats and mice in a range of anticonvulsant tests including: electrically induced seizures, seizures induced chemically by pentylenetetrazole, picrotoxin and N-methyl-D-aspartate (NMDA) and in a genetic animal model, the DBA/2 mouse (Rostock et al. *Epilepsy Research* 1996, 23, 211-223). In addition, retigabine is active in the amygdala kindling model of complex partial seizures, further indicating that this compound has potential for anti-convulsive therapy. In clinical trials, retigabine has recently shown effectiveness in reducing the incidence of seizures in epileptic patients (Bialer et al. *Epilepsy Research* 2002, 51, 31-71).

Retigabine has been shown to activate a K(+) current in neuronal cells and the pharmacology of this induced current displays concordance with the published pharmacology of the M-channel, which recently was correlated to the KCNQ2/3 K(+) channel heteromultimer. This suggests that activation of KCNQ2/3 channels may be responsible for some of the anticonvulsant activity of this agent (Wickenden et al. *Molecular Pharmacology* 2000, 58, 591-600)—and that other agents working by the same mechanism may have similar uses.

KCNQ 2 and 3 channels have also been reported to be upregulated in models of neuropathic pain (Wickenden et al. *Society for Neuroscience Abstracts* 2002, 454.7), and potassium channel modulators have been hypothesised to be active in both neuropathic pain and epilepsy (Schroder et al. *Neuropharmacology* 2001, 40, 888-898).

Retigabine has also been shown to be beneficial in animal models of neuropathic pain (Blackburn-Munro and Jensen *European Journal of Pharmacology* 2003, 460, 109-116), and it is thus suggested that openers of KCNQ channels will be of use in treating pain disorders including neuropathic pain.

The localisation of KCNQ channel mRNA is reported in brain and other central nervous system areas associated with pain (Goldstein et al. *Society for Neuroscience Abstracts* 2003, 53.8).

In addition to a role in neuropathic pain, the expression of mRNA for KCNQ 2-5 in the trigeminal and dorsal root ganglia and in the trigeminal nucleus caudalis implies that openers of these channels may also affect the sensory processing of migraine pain (Goldstein et al. *Society for Neuroscience Abstracts* 2003, 53.8).

Recent reports demonstrate that mRNA for KCNQ 3 and 5, in addition to that for KCNQ2, are expressed in astrocytes and glial cells. Thus KCNQ 2, 3 and 5 channels may help modulate synaptic activity in the CNS and contribute to the neuroprotective effects of KCNQ channel openers (Noda et al., *Society for Neuroscience Abstracts* 2003, 53.9).

Retigabine and other KCNQ modulators may thus exhibit protection against the neurodegenerative aspects of epilepsy, as retigabine has been shown to prevent limbic neurodegeneration and the expression of markers of apoptosis following kainic acid-induced status epilepticus in the rat (Ebert et al. *Epilepsia* 2002, 43 Suppl 5, 86-95). This may have relevance for preventing the progression of epilepsy in patients, i.e. be anti-epileptogenic. Retigabine has also been shown to delay the progression of hippocampal kindling in the rat, a further model of epilepsy development (Tober et al. *European Journal Of Pharmacology* 1996, 303, 163-169).

It is thus suggested that these properties of retigabine and other KCNQ modulators may prevent neuronal damage induced by excessive neuronal activation, and may be of use in the treatment of neurodegenerative diseases, and be disease modifying (or anti-epileptogenic) in patients with epilepsy.

Given that anticonvulsant compounds such as benzodiazepines and chlormethiazole are used clincially in the treatment of the ethanol withdrawal syndrome and that other anticonvulsant compounds e.g. gabapentin, are very effective in animal models of this syndrome (Watson et al. *Neuropharmacology* 1997, 36, 1369-1375), other anticonvulsant compounds such as KCNQ openers are thus expected to be effective in this condition.

mRNA for KCNQ 2 and 3 subunits are found in brain regions associated with anxiety and emotional behaviours such as bipolar disorder e.g. hippocampus and amygdala (Saganich et al. *Journal of Neuroscience* 2001, 21, 4609-4624), and retigabine is reportedly active in some animal models of anxiety-like behaviour (Hartz et al. *Journal of Psychopharmacology* 2003, 17 suppl 3, A28,B16), and other clinically used anticonvulsant compounds are used in the treatment of bipolar disorder.

WO 200196540 discloses the use of modulators of the M-current formed by expression of KCNQ2 and KCNQ3 genes for insomnia, while WO 2001092526 discloses that modulators of KCNQ5 can be utilized for the treatment of sleep disorders.

WO01/022953 describes the use of retigabine for prophylaxis and treatment of neuropathic pain such as allodynia, hyperalgesic pain, phantom pain, neuropathic pain related to diabetic neuropathy and neuropathic pain related to migraine.

WO02/049628 describes the use of retigabine for the prevention, treatment, inhibition and amelioration of anxiety disorders such as anxiety, generalized anxiety disorder, panic anxiety, obsessive compulsive disorder, social phobia, performance anxiety, post-traumatic stress disorder, acute stress reaction, adjustment disorders, hypochondriacal disorders, separation anxiety disorder, agoraphobia and specific phobias.

WO97/15300 describes the use of retigabine for the treatment of neurodegenerative disorders such as Alzheimer's disease; Huntington's chorea; sclerosis such as multiple sclerosis and amyotrophic lateral sclerosis; Creutzfeld-Jakob disease; Parkinson's disease; encephalopathies induced by AIDS or infection by rubella viruses, herpes viruses, borrelia and unknown pathogens; trauma-induced neurodegenerations; neuronal hyperexcitation states such as in medicament withdrawal or intoxication; and neurodegenerative diseases of the peripheral nervous system such as polyneuropathies and polyneuritides.

Hence, there is a great desire for novel compounds, which are potent openers of the KCNQ family potassium channels.

Also desired are novel compounds with improved properties relative to known compounds, which are openers of the KCNQ family potassium channels, such as retigabine. Improvement of one or more of the following parameters is desired: half-life, clearance, selectivity, interactions with other medications, bioavailability, potency, formulability, chemical stability, metabolic stability, membrane permeability, solubility and therapeutic index. The improvement of such parameters may lead to improvements such as:

an improved dosing regime by reducing the number of required doses a day,
ease of administration to patients on multiple medications,
reduced side effects,
enlarged therapeutic index,
improved tolerability or
improved compliance.

SUMMARY OF THE INVENTION

One object of the present invention is to provide novel compounds, which are potent openers of the KCNQ family potassium channels.

The compounds of the invention are substituted aniline derivatives of the general formula I or salts thereof

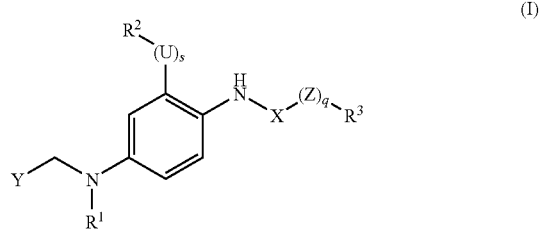

(I)

wherein Y, U, X, Z, s, q, $R^1$, $R^2$ and $R^3$ are as defined below.

The invention further relates to a pharmaceutical composition comprising one or more compounds of formula I and the use thereof.

DETAILED DESCRIPTION OF THE INVENTION

Accordingly, the present invention relates to substituted p-diaminobenzene derivatives of the general formula I

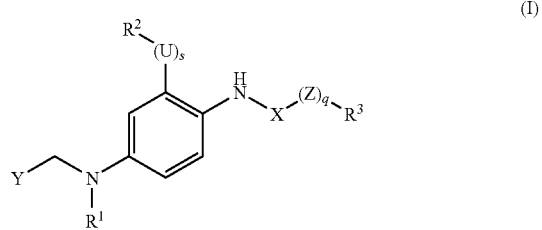

(I)

wherein
s is 0 or 1;
U is O, S, $SO_2$, $SO_2NR^{11}$, CO—O or CO—$NR^{11}$; wherein
$R^{11}$ is selected from the group consisting of hydrogen, $C_{1-6}$-alk(en/yn)yl, $C_{3-8}$-cycloalk(en)yl, $C_{3-8}$-cycloalk(en)yl-$C_{1-6}$-alk(en/yn)yl; or
$R^2$ and $R^{11}$ together with the nitrogen atom form a 5-8 membered saturated or unsaturated ring which optionally contains 1, 2 or 3 further heteroatoms;
q is 0 or 1;
X is CO or $SO_2$; with the proviso that q is 0 when X is $SO_2$;
Z is O or S;
$R^1$ is selected from the group consisting of hydrogen, $C_{1-6}$-alk(en/yn)yl, $C_{3-8}$-cycloalk(en)yl, $C_{3-8}$-cycloalk(en)yl-$C_{1-6}$-alk(en/yn)yl, acyl, hydroxy-$C_{1-6}$-alk(en/yn)yl, hydroxy-$C_{3-8}$-cycloalk(en)yl, hydroxy-$C_{3-8}$-cycloalk(en)

yl-$C_{1-6}$-alk(en/yn)yl, halo-$C_{1-6}$-alk(en/yn)yl, halo-$C_{3-8}$-cycloalk(en)yl, halo-$C_{3-8}$-cycloalk(en)yl-$C_{1-6}$-alk(en/yn)yl, cyano-$C_{1-6}$-alk(en/yn)yl, cyano-$C_{3-8}$-cycloalk(en)yl and cyano-$C_{3-8}$-cycloalk(en)yl-$C_{1-6}$-alk(en/yn)yl;

$R^2$ is selected from the group consisting of hydrogen, $C_{1-6}$-alk(en/yn)yl, $C_{3-8}$-cycloalk(en)yl, $C_{3-8}$-cycloalk(en)-$C_{1-6}$-alk(en/yn)yl, Ar, Ar—$C_{1-6}$-alk(en/yn)yl, Ar—$C_{3-8}$-cycloalk(en)yl, Ar—$C_{3-8}$-cycloalk(en)yl-$C_{1-6}$-alk(en/yn)yl, acyl, hydroxy-$C_{1-6}$-alk(en/yn)yl, hydroxy-$C_{3-8}$-cycloalk(en)yl, hydroxy-$C_{3-8}$-cycloalk(en)yl-$C_{1-6}$-alk(en/yn)yl, halogen, halo-$C_{1-6}$-alk(en/yn)yl, halo-$C_{3-8}$-cycloalk(en)yl, halo-$C_{3-8}$-cycloalk(en)yl-$C_{1-6}$-alk(en/yn)yl, cyano, cyano-$C_{1-6}$-alk(en/yn)yl, cyano-$C_{3-8}$-cycloalk(en)yl, cyano-$C_{3-8}$-cycloalk(en)yl-$C_{1-6}$-alk(en/yn)yl, $NR^{10}R^{10'}$—$C_{1-6}$-alk(en/yn)yl, $NR^{10}R^{10'}$—$C_{3-8}$-cycloalk(en)yl and $NR^{10}R^{10'}$—$C_{3-8}$-cycloalk(en)yl-$C_{1-6}$-alk(en/yn)yl; wherein $R^{10}$ and $R^{10'}$ are independently selected from the group consisting of hydrogen, $C_{1-6}$-alk(en/yn)yl, $C_{3-8}$-cycloalk(en)yl, $C_{3-8}$-cycloalk(en)yl-$C_{1-6}$-alk(en/yn)yl, hydroxy-$C_{1-6}$-alk(en/yn)yl, hydroxy-$C_{3-8}$-cycloalk(en)yl, hydroxy-$C_{3-8}$-cycloalk(en)yl-$C_{1-6}$-alk(en/yn)yl, halo-$C_{1-6}$-alk(en/yn)yl, halo-$C_{3-8}$-cycloalk(en)yl, halo-$C_{3-8}$-cycloalk(en)yl-$C_{1-6}$-alk(en/yn)yl, cyano-$C_{1-6}$-alk(en/yn)yl, cyano-$C_{3-8}$-cycloalk(en)yl and cyano-$C_{3-8}$-cycloalk(en)yl-$C_{1-6}$-alk(en/yn)yl, or $R^{10}$ and $R^{10'}$ together with the nitrogen atom form a 5-8 membered saturated or unsaturated ring which optionally contains 1, 2 or 3 further heteroatoms;

provided that when $R^2$ is halogen or cyano then s is 0; and
provided that U is O or S when s is 1 and $R^2$ is a hydrogen atom or acyl;

$R^3$ is selected from the group consisting of $C_{1-6}$-alk(en/yn)yl, $C_{3-8}$-cycloalk(en)yl, heterocycloalk(en)yl, $C_{3-8}$-cycloalk(en)yl-$C_{1-6}$-alk(en/yn)yl, $C_{1-6}$-alk(en/yn)yl-$C_{3-8}$-cycloalk(en)yl, $C_{1-6}$-alk(en/yn)yl-heterocycloalk(en)yl, heterocycloalk(en)yl-$C_{1-6}$-alk(en/yn)yl, Ar, Ar—$C_{1-6}$-alk(en/yn)yl, Ar—$C_{3-8}$-cycloalk(en)yl, Ar-heterocycloalk(en)yl, Ar—$C_{3-8}$-cycloalk(en)yl-$C_{1-6}$-alk(en/yn)yl, Ar—$C_{1-6}$-alk(en/yn)yl-$C_{3-8}$-cycloalk(en)yl, Ar—$C_{1-6}$-alk(en/yn)yl-heterocycloalk(en)yl, $C_{1-6}$-alk(en/yn)yloxy-$C_{1-6}$-alk(en/yn)yl, $C_{3-8}$-cycloalk(en)yloxy-$C_{1-6}$-alk(en/yn)yl, $C_{1-6}$-alk(en/yn)yloxy-$C_{3-8}$-cycloalk(en)yl, $C_{1-6}$-alk(en/yn)yloxy-heterocycloalk(en)yl, Ar-oxy-$C_{1-6}$-alk(en/yn)yl, Ar—$C_{1-6}$-alk(en/yn)yloxy-$C_{1-6}$-alk(en/yn)yl, $C_{1-6}$-alk(en/yn)yloxy-carbonyl-$C_{1-6}$-alk(en/yn)yl, $C_{3-8}$-cycloalk(en)yloxy-carbonyl-$C_{1-6}$-alk(en/yn)yl, $C_{3-8}$-cycloalk(en)yl-$C_{1-6}$-alk(en/yn)yloxy-carbonyl-$C_{1-6}$-alk(en/yn)yl, hydroxy-$C_{1-6}$-alk(en/yn)yl, hydroxy-$C_{3-8}$-cycloalk(en)yl, hydroxy-heterocycloalk(en)yl, hydroxy-$C_{3-8}$-cycloalk(en)yl-$C_{1-6}$-alk(en/yn)yl, hydroxy-$C_{1-6}$-alk(en/yn)yl-$C_{3-8}$-cycloalk(en)yl, hydroxy-$C_{1-6}$-alk(en/yn)yl-heterocycloalk(en)yl, halo-$C_{1-6}$-alk(en/yn)yl, halo-$C_{3-8}$-cycloalk(en)yl, halo-heterocycloalk(en)yl, halo-$C_{3-8}$-cycloalk(en)yl-$C_{1-6}$-alk(en/yn)yl, halo-$C_{1-6}$-alk(en/yn)yl-$C_{3-8}$-cycloalk(en)yl, halo-$C_{1-6}$-alk(en/yn)yl-heterocycloalk(en)yl, halo-$C_{1-6}$-alk(en/yn)yl-Ar, halo-$C_{3-8}$-cycloalk(en)yl-Ar, halo-$C_{3-8}$-cycloalk(en)yl-$C_{1-6}$-alk(en/yn)yl-Ar, halo-$C_{1-6}$-alk(en/yn)yl-$C_{3-8}$-cycloalk(en)yl-Ar, cyano-$C_{1-6}$-alk(en/yn)yl, cyano-$C_{3-8}$-cycloalk(en)yl, cyano-heterocycloalk(en)yl, cyano-$C_{3-8}$-cycloalk(en)yl-$C_{1-6}$-alk(en/yn)yl, cyano-$C_{1-6}$-alk(en/yn)yl-$C_{3-8}$-cycloalk(en)yl, cyano-$C_{1-6}$-alk(en/yn)yl-heterocycloalk(en)yl, acyl-$C_{1-6}$-alk(en/yn)yl, acyl-$C_{3-8}$-cycloalk(en)yl, acyl-heterocycloalk(en)yl, acyl-$C_{3-8}$-cycloalk(en)yl-$C_{1-6}$-alk(en/yn)yl, acyl-$C_{1-6}$-alk(en/yn)yl-$C_{3-8}$-cycloalk(en)yl, acyl-$C_{1-6}$-alk(en/yn)yl-heterocycloalk(en)yl, $NR^{12}R^{12'}$, optionally substituted $NR^{12}R^{12'}$—$C_{1-6}$-alk(en/yn)yl, optionally substituted $NR^{12}R^{12'}$—$C_{3-8}$-cycloalk(en)yl, optionally substituted $NR^{12}R^{12'}$—$C_{3-8}$-cycloalk(en)yl-$C_{1-6}$-alk(en/yn)yl; wherein $R^{12}$ and $R^{12'}$ are independently selected from the group consisting of hydrogen, $C_{1-6}$-alk(en/yn)yl, $C_{3-8}$-cycloalk(en)yl, $C_{3-8}$-cycloalk(en)yl-$C_{1-6}$-alk(en/yn)yl, Ar, Ar—$C_{1-6}$-alk(en/yn)yl, Ar—$C_{3-8}$-cycloalk(en)yl, Ar—$C_{3-8}$-cycloalk(en)yl-$C_{1-6}$-alk(en/yn)yl, Ar-heterocycloalk(en)yl, Ar-oxy-$C_{1-6}$-alk(en/yn)yl, Ar-oxy-$C_{3-8}$-cycloalk(en)yl, Ar-oxy-$C_{3-8}$-cycloalk(en)yl-$C_{1-6}$-alk(en/yn)yl, Ar-oxy-heterocycloalk(en)yl, hydroxy-$C_{1-6}$-alk(en/yn)yl, hydroxy-$C_{3-8}$-cycloalk(en)yl, hydroxy-$C_{3-8}$-cycloalk(en)yl-$C_{1-6}$ alk(en/yn)yl, halo-$C_{1-6}$-alk(en/yn)yl, halo-$C_{3-8}$-cycloalk(en)yl, halo-$C_{3-8}$-cycloalk(en)yl-$C_{3-8}$-alk(en/yn)yl, Cyano-$C_{1-6}$-alk(en/yn)yl, cyano-$C_{3-8}$-cycloalk(en)yl and cyano-$C_{3-8}$-cycloalk(en)yl-$C_{1-6}$-alk(en/yn)yl, or $R^{12}$ and $R^{12'}$ together with the nitrogen atom form a 5-8 membered saturated or unsaturated ring which optionally contains 1, 2 or 3 further heteroatoms;

with the proviso that when $R^3$ is $NR^{12}R^{12'}$ then q is 0; and

Y represents a group of formula XXIV, XXV, XXVI, XXVII, XXVIII, XXXXI or XXXXII:

wherein the line represents a bond attaching the group represented by Y to the carbon atom;

W is O or S;
V is N, C or CH;
T is N, NH or O,
a is 0, 1, 2 or 3;
b is 0, 1, 2, 3 or 4;
c is 0 or 1;
d is 0, 1, 2 or 3;
e is 0, 1 or 2;
f is 0, 1, 2, 3, 4 or 5;
g is 0, 1, 2, 3 or 4;
h is 0, 1, 2 or 3;

j is 0, 1 or 2;

k is 0, 1, 2 or 3; and each $R^5$ is independently selected from the group consisting of a $C_{1-6}$-alk(en/yn)yl, $C_{3-8}$-cycloalk(en)yl, $C_{3-8}$-cycloalk(en)yl-$C_{1-6}$-alk(en/yn)yl, Ar, Ar—$C_{1-6}$-alk(en/yn)yl, Ar—$C_{3-8}$-cycloalk(en)yl, Ar—$C_{3-8}$-cycloalk(en)yl-$C_{1-6}$-alk(en/yn)yl, Ar-oxy, Ar-oxy-$C_{1-6}$-alk(en/yn)yl, Ar-oxy-$C_{3-8}$-cycloalk(en)yl, $C_{1-6}$-alk(en/yn)yl-heterocycloalk(en)yl, Ar-oxy-$C_{3-8}$-cycloalk(en)yl-$C_{1-6}$-alk(en/yn)yl, acyl, $C_{1-6}$-alk(en/yn)yloxy, $C_{3-8}$-cycloalk(en)yloxy, $C_{3-8}$-cycloalk(en)yl-$C_{1-6}$-alk(en/yn) yloxy, $C_{1-6}$-alk(en/yn)yloxycarbonyl, halogen, halo-$C_{1-6}$-alk(en/yn)yl, halo-$C_{3-8}$-cycloalk(en)yl, halo-$C_{3-8}$-cycloalk(en)yl-$C_{1-6}$-alk(en/yn)yl, —CO—$NR^6R^{6'}$, cyano, cyano-$C_{1-6}$-alk(en/yn)yl, cyano-$C_{3-8}$-cycloalk(en)yl, cyano-$C_{3-8}$-cycloalk(en)yl-$C_{1-6}$-alk(en/yn)yl, $NR^7R^{7'}$, S—$R^8$ and $SO_2R^8$, or two adjacent $R^5$ together with the aromatic group form a 5-8 membered ring which optionally contains one or two heteroatoms;

$R^6$ and $R^{6'}$ are independently selected from the group consisting of hydrogen, $C_{1-6}$-alk(en/yn)yl, $C_{3-8}$-cycloalk(en)yl, $C_{3-8}$-cycloalk(en)yl-$C_{1-6}$-alk(en/yn)yl and Ar;

$R^7$ and $R^{7'}$ are independently selected from the group consisting of hydrogen, $C_{1-6}$-alk(en/yn)yl, $C_{3-8}$-cycloalk(en)yl, $C_{3-8}$-cycloalk(en)yl-$C_{1-6}$-alk(en/yn)yl, Ar, heterocycloalk(en)yl-$C_{1-6}$-alk(en/yn)yl, heterocycloalk(en)yl-$C_{3-8}$-cycloalk(en)yl, heterocycloalk(en)yl-$C_{3-8}$-cycloalk(en)yl-$C_{1-6}$-alk(en/yn)yl, heterocycloalk(en)yl-Ar and acyl; or $R^7$ and $R^{7'}$ together with the nitrogen atom form a 5-8 membered saturated or unsaturated ring which optionally contains 1, 2 or 3 further heteroatoms; and $R^8$ is selected from the group consisting of hydrogen, $C_{1-6}$-alk(en/yn)yl, $C_{3-8}$-cycloalk(en)yl, $C_{3-8}$-cycloalk(en)yl-$C_{1-6}$-alk(en/yn)yl, Ar and —$NR^9R^{9'}$; wherein $R^9$ and $R^{9'}$ are independently selected from the group consisting of hydrogen, $C_{1-6}$-alk(en/yn)yl, $C_{3-8}$-cycloalk(en)yl and $C_{3-8}$-cycloalk(en)yl-$C_{1-6}$-alk(en/yn)yl;

or salts thereof.

In one embodiment, the invention relates to compounds of formula I, wherein s is 1.

In another embodiment, the invention relates to compounds of formula I, wherein s is 0.

In yet another embodiment, the invention relates to compounds of formula I, wherein s is 1 and U is O.

In yet another embodiment, the invention relates to compounds of formula I, wherein s is 1 and U is S.

In yet another embodiment, the invention relates to compounds of formula I, wherein s is 1 and U is $SO_2$.

In yet another embodiment, the invention relates to compounds of formula I, wherein s is 1 and U is $SO_2NR^{11}$. In such compounds, the sulphur atom of $SO_2NR^{11}$ is attached to the benzene ring of formula I whereas the nitrogen atom is attached to $R^2$.

In yet another embodiment, the invention relates to compounds of formula I, wherein s is 1 and U is CO—O. In such compounds, the carbonyl group of CO—O is attached to the benzene ring of formula I whereas the oxygen atom is attached to $R^2$.

In yet another embodiment, the invention relates to compounds of formula I, wherein s is 1 and U is CO—$NR^{11}$. In such compounds, the carbonyl group of CO—$NR^{11}$ is attached to the benzene ring of formula I whereas the nitrogen atom is attached to $R^2$.

In yet another embodiment, the invention relates to compounds of formula I, wherein $R^{11}$ is a hydrogen atom.

In yet another embodiment, the invention relates to compounds of formula I, wherein X is CO.

In yet another embodiment, the invention relates to compounds of formula I, wherein X is $SO_2$, with the proviso that q is 0 when X is $SO_2$.

In yet another embodiment, the invention relates to compounds of formula I, wherein q is 0.

In yet another embodiment, the invention relates to compounds of formula I, wherein q is 1.

In yet another embodiment, the invention relates to compounds of formula I, wherein q is 1 and Z is O.

In yet another embodiment, the invention relates to compounds of formula I, wherein q is 1 and Z is S.

In yet another embodiment, the invention relates to compounds of formula I, wherein X is CO, q is 1 and Z is O.

In yet another embodiment, the invention relates to compounds of formula I, wherein X is CO, q is 1 and Z is S.

In yet another embodiment, the invention relates to compounds of formula I, wherein X is CO and q is 0.

In yet another embodiment, the invention relates to compounds of formula I, wherein X is $SO_2$ and q is 0.

In another embodiment, the invention relates to compounds of formula I, wherein $R^1$ is selected from the group consisting of acyl, hydroxy-$C_{1-6}$-alk(en/yn)yl, hydroxy-$C_{3-8}$-cycloalk(en)yl, hydroxy-$C_{3-8}$-cycloalk(en)yl-$C_{1-6}$-alk(en/yn)yl, halo-$C_{1-6}$-alk(en/yn)yl, halo-$C_{3-8}$-cycloalk(en)yl, halo-$C_{3-8}$-cycloalk(en)yl-$C_{1-6}$-alk(en/yn)yl, cyano-$C_{1-6}$-alk(en/yn)yl, cyano-$C_{3-8}$-cycloalk(en)yl and cyano-$C_{3-8}$-cycloalk(en)yl-$C_{1-6}$-alk(en/yn)yl.

One embodiment of the invention relates to compounds of the general formula I, wherein $R^1$ is selected from the group consisting of hydrogen, $C_{1-6}$-alk(en/yn)yl, $C_{3-8}$-cycloalk(en)yl and $C_{3-8}$-cycloalk(en)yl-$C_{1-6}$-alk(en/yn)yl.

A preferred embodiment of the invention relates to compounds of the general formula I, wherein $R^1$ is selected from the group consisting of hydrogen and $C_{1-6}$-alk(en/yn)yl.

In yet another embodiment, the invention relates to compounds of formula I, wherein $R^1$ is $C_{1-6}$-alk(en/yn)yl, typically $C_{1-3}$-alk(en/yn)yl.

In yet another embodiment, the invention relates to compounds of formula I, wherein $R^1$ is a hydrogen atom.

In yet another embodiment, the invention relates to compounds of formula I, wherein $R^2$ is selected from the group consisting of hydrogen, acyl, hydroxy-$C_{1-6}$-alk(en/yn)yl, hydroxy-$C_{3-8}$-cycloalk(en)yl-$C_{1-6}$-alk(en/yn)yl, cyano-$C_{1-6}$-alk(en/yn)yl, cyano-$C_{3-8}$-cycloalk(en)yl, cyano-$C_{3-8}$-cycloalk(en)yl-$C_{1-6}$-alk(en/yn)yl, $NR^{10}R^{10'}$—$C_{1-6}$-alk(en/yn)yl, $NR^{10}R^{10'}$—$C_{3-8}$-cycloalk(en)yl and $NR^{10}R^{10'}$—$C_{3-8}$-cycloalk(en)yl-$C_{1-6}$-alk(en/yn)yl; wherein $R^{10}$ and $R^{10'}$ are independently selected from the group consisting of hydrogen, $C_{1-6}$-alk(en/yn)yl, $C_{3-8}$-cycloalk(en)yl, $C_{3-8}$-cycloalk(en)yl-$C_{1-6}$-alk(en/yn)yl, hydroxy-$C_{1-6}$-alk(en/yn)yl, hydroxy-$C_{3-8}$-cycloalk(en)yl, hydroxy-$C_{3-8}$-cycloalk(en)yl-$C_{1-6}$-alk(en/yn)yl, halo-$C_{1-6}$-alk(en/yn)yl, halo-$C_{3-8}$-cycloalk(en)yl, halo-$C_{3-8}$-cycloalk(en)yl-$C_{1-6}$-alk(en/yn)yl, cyano-$C_{1-6}$-alk(en/yn)yl, cyano-$C_{3-8}$-cycloalk(en)yl and cyano-$C_{3-8}$-cycloalk(en)yl-$C_{1-6}$-alk(en/yn)yl, or $R^{10}$ and $R^{10'}$ together with the nitrogen atom form a 5-8 membered saturated or unsaturated ring which optionally contains 1, 2 or 3 further heteroatoms;

provided that U is O or S when s is 1 and $R^2$ is a hydrogen atom or acyl.

When $R^2$ represents $NR^{10}R^{10'}$—$C_{1-6}$-alk(en/yn)yl, $NR^{10}R^{10'}$—$C_{3-8}$-cycloalk(en)yl or $NR^{10}R^{10'}$—$C_{3-8}$-cycloalk(en)yl-$C_{1-6}$-alk(en/yn)yl then the nitrogen atom is linked to the remainder of the molecule via $C_{1-6}$-alk(en/yn)yl, $C_{3-8}$-cycloalk(en)yl or $C_{3-8}$-cycloalk(en)yl-$C_{1-6}$-alk(en/yn)yl.

In yet another embodiment, the invention relates to compounds of formula I, wherein $R^2$ is selected from the group consisting of hydrogen, $C_{1-6}$-alk(en/yn)yl, $C_{3-8}$-cycloalk(en)yl, $C_{3-8}$-cycloalk(en)yl-$C_{1-6}$-alk(en/yn)yl, Ar, Ar—$C_{1-6}$-alk(en/yn)yl, Ar—$C_{3-8}$-cycloalk(en)yl, Ar—$C_{3-8}$-cycloalk(en)yl-$C_{1-6}$-alk(en/yn)yl, halogen, halo-$C_{1-6}$-alk(en/yn)yl, halo-$C_{3-8}$-cycloalk(en)yl, halo-$C_{3-8}$-cycloalk(en)yl-$C_{1-6}$-alk(en/yn)yl and cyano;

provided that when $R^2$ is halogen or cyano then s is 0; and provided that U is O or S when s is 1 and $R^2$ is a hydrogen atom.

In yet another embodiment, the invention relates to compounds of formula I, wherein $R^2$ is selected from the group consisting of hydrogen, $C_{1-6}$-alk(en/yn)yl, $C_{3-8}$-cycloalk(en)yl, Ar, Ar—$C_{1-6}$-alk(en/yn)yl, halogen, halo-$C_{1-6}$-alk(en/yn)yl and cyano;

provided that when $R^2$ is halogen or cyano then s is 0; and provided that U is O or S when s is 1 and $R^2$ is a hydrogen atom.

In a preferred embodiment, the invention relates to compounds of formula I, wherein $R^2$ is selected from the group consisting of $C_{1-6}$-alk(en/yn)yl, $C_{3-8}$-cycloalk(en)yl, Ar—$C_{1-6}$-alk(en/yn)yl, halogen and cyano; provided that when $R^2$ is halogen or cyano then s is 0.

In yet another embodiment, the invention relates to compounds of formula I, wherein $R^2$ is a hydrogen atom.

In yet another embodiment, the invention relates to compounds of formula I, wherein $R^2$ is not a hydrogen atom.

In yet another embodiment, the invention relates to compounds of formula I, wherein $R^2$ is $C_{1-6}$-alk(en/yn)yl, $C_{1-3}$-alk(en/yn)yl.

In yet another embodiment, the invention relates to compounds of formula I, wherein $R^2$ is $C_{3-8}$-cycloalk(en)yl, typically $C_{3-6}$-cycloalk(en)yl.

In yet another embodiment, the invention relates to compounds of formula I, wherein $R^2$ is Ar.

In yet another embodiment, the invention relates to compounds of formula I, wherein $R^2$ is not Ar.

In yet another embodiment, the invention relates to compounds of formula I, wherein $R^2$ is Ar—$C_{1-6}$-alk(en/yn)yl, typically Ar—$C_{1-3}$-alk(en/yn)yl.

In yet another embodiment, the invention relates to compounds of formula I, wherein $R^2$ is a halogen atom, typically a chloro atom, a bromo atom or an iodo atom.

In yet another embodiment, the invention relates to compounds of formula I, wherein $R^2$ is halo-$C_{1-6}$-alk(en/yn)yl, typically halo-$C_{1-3}$-alk(en/yn)yl.

In yet another embodiment, the invention relates to compounds of formula I, wherein $R^2$ is not halo-$C_{1-6}$-alk(en/yn)yl, typically halo-$C_{1-3}$-alk(en/yn)yl.

In yet another embodiment, the invention relates to compounds of formula I, wherein $R^2$ is cyano.

In yet another embodiment, the invention relates to compounds of formula I, wherein $R^{10}$ and $R^{10'}$ are independently selected from the group consisting of hydrogen, $C_{1-6}$-alk(en/yn)yl, $C_{3-8}$-cycloalk(en)yl, $C_{3-8}$-cycloalk(en)yl-$C_{1-6}$-alk(en/yn)yl.

In yet another embodiment, the invention relates to compounds of formula I, wherein $R^{10}$ and $R^{10'}$ are independently selected from the group consisting of hydrogen and $C_{1-6}$-alk(en/yn)yl.

In yet another embodiment, the invention relates to compounds of formula I, wherein s is 1, U is O and $R^2$ is selected from the group consisting of $C_{1-6}$-alk(en/yn)yl, $C_{3-8}$-cycloalk(en)yl, $C_{3-8}$-cycloalk(en)yl-$C_{1-6}$-alk(en/yn)yl, Ar—$C_{1-6}$-alk(en/yn)yl, Ar—$C_{3-8}$-cycloalk(en)yl, Ar—$C_{3-8}$-cycloalk(en)yl-$C_{1-6}$-alk(en/yn)yl, halo-$C_{1-6}$-alk(en/yn)yl, halo-$C_{3-8}$-cycloalk(en)yl and halo-$C_{3-8}$-cycloalk(en)yl-$C_{1-6}$-alk(en/yn)yl.

In yet another embodiment, the invention relates to compounds of formula I, wherein s is 1, U is O and $R^2$ is selected from the group consisting of $C_{1-6}$-alk(en/yn)yl, $C_{3-8}$-cycloalk(en)yl, Ar—$C_{1-6}$-alk(en/yn)yl and halo-$C_{1-6}$-alk(en/yn)yl.

In yet another embodiment, the invention relates to compounds of formula I, wherein s is 1, U is O and $R^2$ is selected from the group consisting of $C_{1-6}$-alk(en/yn)yl, $C_{3-8}$-cycloalk(en)yl and Ar—$C_{1-6}$-alk(en/yn)yl.

In yet another embodiment, the invention relates to compounds of formula I, wherein s is 1, U is S and $R^2$ is selected from the group consisting of $C_{1-6}$-alk(en/yn)yl, $C_{3-8}$-cycloalk(en)yl, $C_{3-8}$-cycloalk(en)yl-$C_{1-6}$-alk(en/yn)yl, Ar—$C_{1-6}$-alk(en/yn)yl, Ar—$C_{3-8}$ cycloalk(en)yl and Ar—$C_{3-8}$-cycloalk(en)yl-$C_{1-6}$ alk(en/yn)yl.

In yet another embodiment, the invention relates to compounds of formula I, wherein s is 1, U is S and $R^2$ is selected from the group consisting of $C_{1-6}$-alk(en/yn)yl and Ar—$C_{1-6}$-alk(en/yn)yl.

In yet another embodiment, the invention relates to compounds of formula I, wherein s is 1, U is S and $R^2$ is selected from the group consisting of $C_{3-8}$-cycloalk(en)yl and Ar—$C_{1-6}$-alk(en/yn)yl.

In yet another embodiment, the invention relates to compounds of formula I, wherein s is 0 and $R^2$ is selected from the group consisting of $C_{1-6}$-alk(en/yn)yl, $C_{3-8}$-cycloalk(en)yl, $C_{3-8}$-cycloalk(en)yl-$C_{1-6}$-alk(en/yn)yl, Ar, halogen, halo-$C_{1-6}$-alk(en/yn)yl, halo-$C_{3-8}$-cycloalk(en)yl, halo-$C_{3-8}$-cycloalk(en)yl-$C_{1-6}$-alk(en/yn)yl and cyano.

In yet another embodiment, the invention relates to compounds of formula I, wherein s is 0 and $R^2$ is selected from the group consisting of $C_{1-6}$-alk(en/yn)yl, Ar, halogen, halo-$C_{1-6}$-alk(en/yn)yl and cyano.

In yet another embodiment, the invention relates to compounds of formula I, wherein s is 0 and $R^2$ is selected from the group consisting of $C_{1-6}$-alk(en/yn)yl, halogen and cyano.

In yet another embodiment, the invention relates to compounds of formula I, wherein s is 1, U is CO—O and $R^2$ is selected from the group consisting of $C_{1-6}$-alk(en/yn)yl, $C_{3-8}$-cycloalk(en)yl, $C_{3-8}$-cycloalk(en)yl-$C_{1-6}$-alk(en/yn)yl.

In yet another embodiment, the invention relates to compounds of formula I, wherein s is 1, U is CO—O and $R^2$ is $C_{1-6}$-alk(en/yn)yl.

In yet another embodiment, the invention relates to compounds of formula I, wherein s is 1, U is CO—$NR^{11}$, $R^{11}$ is a hydrogen atom and $R^2$ is different from $C_{3-8}$-cycloalk(en)yl, hydroxy-$C_{3-8}$-cycloalk(en)yl, halo-$C_{3-8}$-cycloalk(en)yl, cyano-$C_{3-8}$-cycloalk(en)yl and Ar.

In yet another embodiment, the invention relates to compounds of formula I, wherein s is 1, U is CO—$NR^{11}$ and $R^2$ is selected from the group consisting of $C_{1-6}$-alk(en/yn)yl, $C_{3-8}$-cycloalk(en)yl, $C_{3-8}$-cycloalk(en)yl-$C_{1-6}$-alk(en/yn)yl.

In yet another embodiment, the invention relates to compounds of formula I, wherein s is 1, U is CO—$NR^{11}$ and $R^2$ is $C_{1-6}$-alk(en/yn)yl.

In yet another embodiment, the invention relates to compounds of formula I, wherein $R^{11}$ is a hydrogen atom.

In yet another embodiment, the invention relates to compounds of formula I, wherein $R^3$ is selected from the group consisting of heterocycloalk(en)yl, $C_{1-6}$-alk(en/yn)yl-heterocycloalk(en)yl, Ar-heterocycloalk(en)yl, Ar—$C_{1-6}$-alk(en/yn)yl-heterocycloalk(en)yl, $C_{1-6}$-alk(en/yn)yloxy-heterocycloalk(en)yl, hydroxy-$C_{1-6}$-alk(en/yn)yl, hydroxy-$C_{3-8}$-cycloalk(en)yl, hydroxy-heterocycloalk(en)yl, hydroxy-$C_{3-8}$-cycloalk(en)yl-$C_{1-6}$-alk(en/yn)yl, hydroxy-$C_{1-6}$-alk(en/ yn)yl-$C_{3-8}$-cycloalk(en)yl, hydroxy-$C_{1-6}$-alk(en/yn)yl-heterocycloalk(en)yl, halo-heterocycloalk(en)yl, halo-$C_{1-6}$-alk(en/yn)yl-heterocycloalk(en)yl, cyano-$C_{1-6}$-alk(en/yn)yl, cyano-$C_{3-8}$-cycloalk(en)yl, cyano-heterocycloalk(en)yl, cyano-$C_{3-8}$-cycloalk(en)yl-$C_{1-6}$-alk(en/yn)yl, cyano-$C_{1-6}$-alk(en/yn)yl-$C_{3-8}$-cycloalk(en)yl, cyano-$C_{1-6}$-alk(en/yn)yl-heterocycloalk(en)yl, acyl-$C_{1-6}$-alk(en/yn)yl, acyl-$C_{3-8}$-cycloalk(en)yl, acyl-heterocycloalk(en)yl, acyl-$C_{3-8}$-cycloalk(en)yl-$C_{1-6}$-alk(en/yn)yl, acyl-$C_{1-6}$-alk(en/yn)yl-$C_{3-8}$-cycloalk(en)yl, acyl-$C_{1-6}$-alk(en/yn)yl-heterocycloalk(en)yl, $NR^{12}R^{12'}$; wherein $R^{12}$ and $R^{12'}$ are independently selected from the group consisting of hydrogen, $C_{1-6}$-alk(en/yn)yl, $C_{3-8}$-cycloalk(en)yl, $C_{3-8}$-cycloalk(en)yl-$C_{1-6}$-alk(en/yn)yl, Ar, Ar—$C_{1-6}$-alk(en/yn)yl, Ar—$C_{3-8}$-cycloalk(en)yl, Ar—$C_{3-8}$-cycloalk(en)yl-$C_{1-6}$-alk(en/yn)yl, Ar-heterocycloalk(en)yl, Ar-oxy-$C_{1-6}$-alk(en/yn)yl, Ar-oxy-$C_{3-8}$-cycloalk(en)yl, Ar-oxy-$C_{3-8}$-cycloalk(en)yl-$C_{1-6}$-alk(en/yn)yl, Ar-oxy-heterocycloalk(en)yl, hydroxy-$C_{1-6}$-alk(en/yn)yl, hydroxy-$C_{3-8}$-cycloalk(en)yl, hydroxy-$C_{3-8}$-cycloalk(en)yl-$C_{1-6}$-alk(en/yn)yl, halo-$C_{1-6}$-alk(en/yn)yl, halo-$C_{3-8}$-cycloalk(en)yl, halo-$C_{3-8}$-cycloalk(en)yl-$C_{1-6}$-alk(en/yn)yl, cyano-$C_{1-6}$-alk(en/yn)yl, cyano-$C_{3-8}$-cycloalk(en)yl and cyano-$C_{3-8}$-cycloalk(en)yl-$C_{1-6}$-alk(en/yn)yl, or $R^{12}$ and $R^{2'}$ together with the nitrogen atom form a 5-8 membered saturated or unsaturated ring which optionally contains 1, 2 or 3 further heteroatoms;

with the proviso that when $R^3$ is $NR^{12}R^{12'}$ then q is 0.

When $R^3$ represents $NR^{12}R^{12'}$—$C_{1-6}$-alk(en/yn)yl, $NR^{12}R^{12'}$—$C_{3-8}$-cycloalk(en)yl or $NR^{12}R^{12'}$—$C_{3-8}$-cycloalk(en)yl-$C_{1-6}$-alk(en/yn)yl then the nitrogen atom is linked to the $X-(Z)_p$ group via the $C_{1-6}$-alk(en/yn)yl, $C_{3-8}$-cycloalk(en)yl or $C_{3-8}$-cycloalk(en)yl-$C_{1-6}$-alk(en/yn)yl group.

In yet another embodiment, the invention relates to compounds of formula I, wherein $R^3$ is selected from the group consisting of $C_{1-6}$-alk(en/yn)yl, $C_{3-8}$-cycloalk(en)yl, $C_{3-8}$-cycloalk(en)yl-$C_{1-6}$-alk(en/yn)yl, $C_{1-6}$-alk(en/yn)yl-$C_{3-8}$-cycloalk(en)yl, heterocycloalk(en)yl-$C_{1-6}$-alk(en/yn)yl, heterocycloalk(en)yl, Ar, Ar—$C_{1-6}$-alk(en/yn)yl, Ar—$C_{3-8}$-cycloalk(en)yl, Ar—$C_{3-8}$-cycloalk(en)yl-$C_{1-6}$-alk(en/yn)yl, Ar—$C_{1-6}$-alk(en/yn)yl-$C_{3-8}$-cycloalk(en)yl, $C_{1-6}$-alk(en/yn)yloxy-$C_{1-6}$-alk(en/yn)yl, $C_{3-8}$-cycloalk(en)yloxy-$C_{1-6}$-alk(en/yn)yl, $C_{1-6}$-alk(en/yn)yloxy-$C_{3-8}$-cycloalk(en)yl, Ar-oxy-$C_{1-6}$-alk(en/yn)yl, Ar—$C_{1-6}$-alk(en/yn)yloxy-$C_{1-6}$-alk(en/yn)yl, $C_{1-6}$-alk(en/yn)yloxy-carbonyl-$C_{1-6}$-alk(en/yn)yl, $C_{3-8}$-cycloalk(en)yloxy-carbonyl-$C_{1-6}$-alk(en/yn)yl, $C_{3-8}$-cycloalk(en)yl-$C_{1-6}$-alk(en/yn)yloxy-carbonyl-$C_{1-6}$-alk(en/yn)yl, halo-$C_{1-6}$-alk(en/yn)yl, halo-$C_{3-8}$-cycloalk(en)yl, halo-$C_{3-8}$-cycloalk(en)yl-$C_{1-6}$-alk(en/yn)yl, halo-$C_{1-6}$-alk(en/yn)yl-$C_{3-8}$-cycloalk(en)yl, halo-$C_{1-6}$-alk(en/yn)yl-Ar, halo-$C_{3-8}$-cycloalk(en)yl-Ar, halo-$C_{3-8}$-cycloalk(en)yl-$C_{1-6}$-alk(en/yn)yl-Ar, halo-$C_{1-6}$-alk(en/yn)yl-$C_{3-8}$-cycloalk(en)yl-Ar, $NR^{12}R^{12'}$, optionally substituted $NR^{12}R^{12'}$—$C_{1-6}$-alk(en/yn)yl, optionally substituted $NR^{12}R^{12'}$—$C_{3-8}$-cycloalk(en)yl and optionally substituted $NR^{12}R^{12'}$—$C_{3-8}$-cycloalk(en)yl-$C_{1-6}$-alk(en/yn)yl.

In yet another embodiment, the invention relates to compounds of formula I, wherein $R^3$ is selected from the group consisting of $C_{1-6}$-alk(en/yn)yl, $C_{3-8}$-cycloalk(en)yl, $C_{3-8}$-cycloalk(en)yl-$C_{1-6}$-alk(en/yn)yl, heterocycloalk(en)yl-$C_{1-6}$-alk(en/yn)yl, heterocycloalk(en)yl, Ar, Ar—$C_{1-6}$-alk(en/yn)yl, $C_{1-6}$-alk(en/yn)yloxy-$C_{1-6}$-alk(en/yn)yl, Ar-oxy-$C_{1-6}$-alk(en/yn)yl, Ar—$C_{1-6}$-alk(en/yn)yloxy-$C_{1-6}$-alk(en/yn)yl, $C_{1-6}$-alk(en/yn)yloxy-carbonyl-$C_{1-6}$-alk(en/yn)yl, halo-$C_{1-6}$-alk(en/yn)yl, halo-$C_{1-6}$-alk(en/yn)yl-Ar, $NR^{12}R^{12'}$, optionally substituted $NR^{12}R^{12'}$—$C_{1-6}$-alk(en/yn)yl, and optionally substituted $NR^{12}R^{12'}$—$C_{3-8}$-cycloalk(en)yl.

In a preferred embodiment, the invention relates to compounds of formula I, wherein $R^3$ is $C_{1-6}$-alk(en/yn)yl, typically $C_{1-3}$-alk(en/yn)yl.

In yet another embodiment, the invention relates to compounds of formula I, wherein $R^3$ is $C_{3-8}$-cycloalk(en)yl.

In yet another embodiment, the invention relates to compounds of formula I, wherein $R^3$ is $C_{3-8}$-cycloalk(en)yl-$C_{1-6}$-alk(en/yn)yl.

In yet another embodiment, the invention relates to compounds of formula I, wherein $R^3$ is Ar.

In yet another embodiment, the invention relates to compounds of formula I, wherein $R^3$ is heterocycloalk(en)yl.

In yet another embodiment, the invention relates to compounds of formula I, wherein $R^3$ is not heterocycloalk(en)yl.

In yet another embodiment, the invention relates to compounds of formula I, wherein $R^3$ is heterocycloalk(en)yl-$C_{1-6}$-alk(en/yn)yl.

In yet another embodiment, the invention relates to compounds of formula I, wherein $R^3$ is not heterocycloalk(en)yl-$C_{1-6}$-alk(en/yn)yl.

In yet another embodiment, the invention relates to compounds of formula I, wherein $R^3$ is Ar—$C_{1-6}$-alk(en/yn)yl.

In yet another embodiment, the invention relates to compounds of formula I, wherein $R^3$ is $C_{1-6}$-alk(en/yn)yloxy-$C_{1-6}$-alk(en/yn)yl.

In yet another embodiment, the invention relates to compounds of formula I, wherein $R^3$ is not $C_{1-6}$-alk(en/yn)yloxy-$C_{1-6}$-alk(en/yn)yl.

In yet another embodiment, the invention relates to compounds of formula I, wherein $R^3$ is Ar-oxy-$C_{1-6}$-alk(en/yn)yl.

In yet another embodiment, the invention relates to compounds of formula I, wherein $R^3$ is Ar—$C_{1-6}$-alk(en/yn)yloxy-$C_{1-6}$-alk(en/yn)yl.

In yet another embodiment, the invention relates to compounds of formula I, wherein $R^3$ is $C_{1-6}$-alk(en/yn)yloxy-carbonyl-$C_{1-6}$-alk(en/yn)yl.

In yet another embodiment, the invention relates to compounds of formula I, wherein $R^3$ is halo-$C_{1-6}$-alk(en/yn)yl.

In yet another embodiment, the invention relates to compounds of formula I, wherein $R^3$ is halo-$C_{1-6}$-alk(en/yn)yl-Ar.

In yet another embodiment, the invention relates to compounds of formula I, wherein $R^3$ is not halo-$C_{1-6}$-alk(en/yn)yl-Ar.

In yet another embodiment, the invention relates to compounds of formula I, wherein $R^3$ is $NR^{12}R^{12'}$.

In yet another embodiment, the invention relates to compounds of formula I, wherein $R^3$ is not $NR^{12}R^{12'}$.

In yet another embodiment, the invention relates to compounds of formula I, wherein $R^3$ is optionally substituted $NR^{12}R^{12'}$—$C_{1-6}$-alk(en/yn)yl.

In yet another embodiment, the invention relates to compounds of formula I, wherein $R^3$ is different from optionally substituted $NR^{12}R^{12'}$—$C_{1-6}$-alk(en/yn)yl.

In yet another embodiment, the invention relates to compounds of formula I, wherein $R^3$ is optionally substituted $NR^{12}R^{12'}$—$C_{3-8}$-cycloalk(en)yl.

In yet another embodiment, the invention relates to compounds of formula I, wherein $R^3$ is different from optionally substituted $NR^{12}R^{12'}$—$C_{3-8}$-cycloalk(en)yl.

In yet another embodiment, the invention relates to compounds of formula I, wherein $R^3$ is optionally substituted $NR^{12}R^{12'}$—$C_{3-8}$-cycloalk(en)yl-$C_{1-6}$-alk(en/yn)yl.

In yet another embodiment, the invention relates to compounds of formula I, wherein $R^3$ is different from optionally substituted $NR^{12}R^{12'}$—$C_{3-8}$-cycloalk(en)yl-$C_{1-6}$-alk(en/yn)yl.

In yet another embodiment, the invention relates to compounds of formula I, wherein $R^{12}$ and $R^{12'}$ are independently selected from the group consisting of Ar-heterocycloalk(en)yl, Ar-oxy-$C_{1-6}$-alk(en/yn)yl, Ar-oxy-$C_{3-8}$-cycloalk(en)yl, Ar-oxy-$C_{3-8}$-cycloalk(en)yl-$C_{1-6}$-alk(en/yn)yl, Ar-oxy-heterocycloalk(en)yl, hydroxy-$C_{1-6}$-alk(en/yn)yl, hydroxy-$C_{3-8}$-cycloalk(en)yl, hydroxy-$C_{3-8}$-cycloalk(en)yl-$C_{1-6}$-alk(en/yn)yl, halo-$C_{1-6}$-alk(en/yn)yl, halo-$C_{3-8}$-cycloalk(en)yl, halo-$C_{3-8}$-cycloalk(en)yl-$C_{1-6}$-alk(en/yn)yl, cyano-$C_{1-6}$-alk(en/Yn)yl, cyano-$C_{3-8}$-cycloalk(en)yl and cyano-$C_{3-8}$-cycloalk(en)yl-$C_{1-6}$-alk(en/yn)yl, or
$R^{12}$ and $R^{12'}$ together with the nitrogen atom form a 5-8 membered saturated or unsaturated ring which optionally contains 1, 2 or 3 further heteroatoms;
with the proviso that when $R^3$ is $NR^{12}R^{12'}$ then q is 0.

In yet another embodiment, the invention relates to compounds of formula I, wherein $R^{12}$ and $R^{12'}$ are independently selected from the group consisting of hydrogen, $C_{1-6}$-alk(en/yn)yl, $C_{3-8}$-cycloalk(en)yl, $C_{3-8}$-cycloalk(en)yl-$C_{1-6}$-alk(en/yn)yl, Ar, Ar—$C_{1-6}$-alk(en/yn)yl, Ar—$C_{3-8}$-cycloalk(en)yl, Ar—$C_{3-8}$-cycloalk(en)yl-$C_{1-6}$-alk(en/yn)yl.

In yet another embodiment, the invention relates to compounds of formula I, wherein $R^{12}$ and $R^{12'}$ are independently selected from the group consisting of hydrogen, $C_{1-6}$-alk(en/yn)yl and Ar.

In yet another embodiment, the invention relates to compounds of formula I, wherein at least one of $R^{12}$ and $R^{12'}$ is a hydrogen atom.

In yet another embodiment, the invention relates to compounds of formula I, wherein at least one of $R^{12}$ and $R^{12'}$ is $C_{1-6}$-alk(en/yn)yl.

In yet another embodiment, the invention relates to compounds of formula I, wherein at least one of $R^{12}$ and $R^{12'}$ is Ar.

In yet another embodiment, the invention relates to compounds of formula I, wherein X is CO, q is 1, Z is O and $R^3$ is selected from the group consisting of $C_{1-6}$-alk(en/yn)yl, $C_{3-8}$-cycloalk(en)yl, $C_{3-8}$-cycloalk(en)yl-$C_{1-6}$-alk(en/yn)yl, $C_{1-6}$-alk(en/yn)yl-$C_{3-8}$-cycloalk(en)yl, Ar, Ar—$C_{3-8}$ alk(en/yn)yl, Ar—$C_{3-8}$-cycloalk(en)yl, Ar—$C_{3-8}$-cycloalk(en)yl-$C_{1-6}$-alk(en/yn)yl, Ar—$C_{1-6}$-alk(en/yn)yl-$C_{3-8}$-cycloalk(en)yl, $C_{1-6}$-alk(en/yn)yloxy-$C_{1-6}$-alk(en/yn)yl, $C_{3-8}$-cycloalk(en)yloxy-$C_{1-6}$-alk(en/yn)yl, $C_{1-6}$-alk(en/yn)yloxy-$C_{3-8}$-cycloalk(en)yl, Ar-oxy-$C_{1-6}$-alk(en/yn)yl, Ar—$C_{1-6}$-alk(en/yn)yloxy-$C_{1-6}$-alk(en/yn)yl, halo-$C_{1-6}$-alk(en/yn)yl, halo-$C_{3-8}$-cycloalk(en)yl, halo-$C_{3-8}$-cycloalk(en)yl-$C_{1-6}$-alk(en/yn)yl and halo-$C_{1-6}$-alk(en/yn)yl-$C_{3-8}$-cycloalk(en)yl.

In yet another embodiment, the invention relates to compounds of formula I, wherein X is CO, q is 1, Z is O and $R^3$ is selected from the group consisting of $C_{1-6}$-alk(en/yn)yl, Ar, Ar—$C_{1-6}$-alk(en/yn)yl, $C_{1-6}$-alk(en/yn)yloxy-$C_{1-6}$-alk(en/yn)yl, Ar—$C_{1-6}$-alk(en/yn)yloxy-$C_{1-6}$-alk(en/yn)yl and halo-$C_{1-6}$-alk(en/yn)yl.

In yet another embodiment, the invention relates to compounds of formula I, wherein X is CO, q is 1, Z is O and $R^3$ is not $C_{1-6}$-alk(en/yn)yloxy-$C_{1-6}$-alk(en/yn)yl.

In yet another embodiment, the invention relates to compounds of formula I, wherein X is CO, q is 1, Z is O and $R^3$ is $C_{1-6}$-alk(en/yn)yl, typically $C_{1-3}$-alk(en/yn)yl.

In yet another embodiment, the invention relates to compounds of formula I, wherein X is CO, q is 1, Z is S and $R^3$ is selected from the group consisting of $C_{1-6}$-alk(en/yn)yl, $C_{3-8}$-cycloalk(en)yl, $C_{3-8}$-cycloalk(en)yl-$C_{1-6}$-alk(en/yn)yl, $C_{1-6}$-alk(en/yn)yl-$C_{3-8}$-cycloalk(en)yl, Ar—$C_{1-6}$-alk(en/yn)yl, Ar—$C_{3-8}$-cycloalk(en)yl, Ar—$C_{3-8}$-cycloalk(en)yl-$C_{1-6}$-alk(en/yn)yl and Ar—$C_{1-6}$-alk(en/yn)yl-$C_{3-8}$-cycloalk(en)yl.

In yet another embodiment, the invention relates to compounds of formula I, wherein X is CO, q is 1, Z is S and $R^3$ is selected from the group consisting of $C_{1-6}$-alk(en/yn)yl and Ar—$C_{1-6}$-alk(en/yn)yl.

In yet another embodiment, the invention relates to compounds of formula I, wherein X is CO, q is 1, Z is S and $R^3$ is $C_{1-6}$-alk(en/yn)yl.

In yet another embodiment, the invention relates to compounds of formula I, wherein X is CO, q is 0, $R^3$ is selected from the group consisting of $C_{1-6}$-alk(en/yn)yl, $C_{3-8}$-cycloalk(en)yl, $C_{3-8}$-cycloalk(en)yl-$C_{1-6}$-alk(en/yn)yl, $C_{1-6}$-alk(en/yn)yl-$C_{3-8}$-cycloalk(en)yl, heterocycloalk(en)yl, Ar, Ar—$C_{1-6}$-alk(en/yn)yl, Ar—$C_{3-8}$-cycloalk(en)yl, Ar—$C_{3-8}$-cycloalk(en)yl-$C_{1-6}$-alk(en/yn)yl, Ar—$C_{1-6}$ alk(en/yn)yl-$C_{3-8}$-cycloalk(en)yl, Ar-oxy-$C_{1-6}$-alk(en/yn)yl, Ar—$C_{1-6}$-alk(en/yn)yloxy-$C_{1-6}$-alk(en/yn)yl, $C_{1-6}$-alk(en/yn)yloxy-carbonyl-$C_{1-6}$-alk(en/yn)yl, $C_{3-8}$-cycloalk(en)yloxy-carbonyl-$C_{1-6}$-alk(en/yn)yl, $C_{3-8}$-cycloalk(en)yl-$C_{1-6}$-alk(en/yn)yloxy-carbonyl-$C_{1-6}$-alk(en/yn)yl, halo-$C_{1-6}$-alk(en/yn)yl, halo-$C_{3-8}$-cycloalk(en)yl, halo-$C_{3-8}$-cycloalk(en)yl-$C_{1-6}$-alk(en/yn)yl, halo-$C_{1-6}$-alk(en/yn)yl-$C_{3-8}$-cycloalk(en)yl, halo-$C_{1-6}$-alk(en/yn)yl-Ar, halo-$C_{3-8}$-cycloalk(en)yl-Ar, halo-$C_{3-8}$-cycloalk(en)yl-$C_{1-6}$-alk(en/yn)yl-Ar, halo-$C_{1-6}$-alk(en/yn)yl-$C_{3-8}$-cycloalk(en)yl-Ar, $NR^{12}R^{12'}$, optionally substituted $NR^{12}R^{12'}$—$C_{1-6}$-alk(en/yn)yl, and optionally substituted $NR^{12}R^{12'}$—$C_{3-8}$-cycloalk(en)yl.

In yet another embodiment, the invention relates to compounds of formula I, wherein X is CO, q is 0, $R^3$ is selected from the group consisting of $C_{1-6}$-alk(en/yn)yl, $C_{3-8}$-cycloalk(en)yl, $C_{3-8}$-cycloalk(en)yl-$C_{1-6}$-alk(en/yn)yl, heterocycloalk(en)yl, Ar, Ar—$C_{1-6}$-alk(en/yn)yl, Ar-oxy-$C_{1-6}$-alk(en/yn)yl, $C_{1-6}$-alk(en/yn)yloxy-carbonyl-$C_{1-6}$-alk(en/yn)yl, halo-$C_{1-6}$-alk(en/yn)yl, halo-$C_{1-6}$-alk(en/yn)yl-Ar, $NR^{12}R^{12'}$, optionally substituted $NR^{12}R^{12'}$—$C_{1-6}$-alk(en/yn)yl, and optionally substituted $NR^{12}R^{12'}$—$C_{3-8}$-cycloalk(en)yl.

In yet another embodiment, the invention relates to compounds of formula I, wherein X is $SO_2$, q is 0 and $R^3$ is selected from the group consisting of $C_{1-6}$-alk(en/yn)yl, $C_{3-8}$-cycloalk(en)yl, $C_{3-8}$-cycloalk(en)yl-$C_{1-6}$-alk(en/yn)yl, $C_{1-6}$-alk(en/yn)yl-$C_{3-8}$-cycloalk(en)yl, Ar—$C_{1-6}$-alk(en/yn)yl, Ar—$C_{3-8}$-cycloalk(en)yl, Ar—$C_{3-8}$-cycloalk(en)yl-$C_{1-6}$-alk(en/yn)yl, Ar—$C_{1-6}$-alk(en/yn)yl-$C_{3-8}$-cycloalk(en)yl.

In yet another embodiment, the invention relates to compounds of formula I, wherein X is $SO_2$, q is 0 and $R^3$ is selected from the group consisting of $C_{1-6}$-alk(en/yn)yl and Ar—$C_{1-6}$-alk(en/yn)yl.

In a preferred embodiment, the invention relates to compounds of formula I, wherein $R^3$ is Ar and q is 1.

In a preferred embodiment, the invention relates to compounds of formula I, wherein $R^3$ is Ar and q is 0.

In a preferred embodiment, the invention relates to compounds of formula I, wherein $R^3$ is not Ar when q is 0.

In another embodiment, the invention relates to compounds of formula I, wherein Y is of formulae XXIV, XXV, XXVII, XXXXI or XXXXII.

In another embodiment, the invention relates to compounds of formula I, wherein Y is of formula XXIV.

In yet another embodiment, the invention relates to compounds of formula I, wherein Y is of formula XXV.

In yet another embodiment, the invention relates to compounds of formula I, wherein Y is of formula XXVII.

In yet another embodiment, the invention relates to compounds of formula I, wherein Y is of formula XXXXI.

In yet another embodiment, the invention relates to compounds of formula I, wherein Y is of formula XXXXII.

In yet another embodiment, the invention relates to compounds of formula I, wherein W is an oxygen atom.

In yet another embodiment, the invention relates to compounds of formula I, wherein W is a sulphur atom.

In yet another embodiment, the invention relates to compounds of formula I, wherein V is a nitrogen atom.

In yet another embodiment, the invention relates to compounds of formula I, wherein V is CH.

In yet another embodiment, the invention relates to compounds of formula I, wherein T is a nitrogen atom.

In yet another embodiment, the invention relates to compounds of formula I, wherein T is an oxygen atom.

In yet another embodiment, the invention relates to compounds of formula I, wherein each $R^5$ is independently selected from the group consisting of Ar-oxy-$C_{1-6}$-alk(en/yn)yl, Ar-oxy-$C_{3-8}$-cycloalk(en)yl, Ar-oxy-$C_{3-8}$-cycloalk(en)yl-$C_{1-6}$-alk(en/yn)yl, acyl, —CO—$NR^6R^{6'}$, cyano, cyano-$C_{1-6}$-alk(en/yn)yl, cyano-$C_{3-8}$-cycloalk(en)yl and cyano-$C_{3-8}$-cycloalk(en)yl-$C_{1-6}$-alk(en/yn)yl.

In yet another embodiment, the invention relates to compounds of formula I, wherein each $R^5$ is independently selected from the group consisting of a $C_{1-6}$-alk(en/yn)yl, $C_{3-8}$-cycloalk(en)yl, $C_{3-8}$-cycloalk(en)yl-$C_{1-6}$-alk(en/yn)yl, $C_{1-6}$-alk(en/yn)yl-heterocycloalk(en)yl, Ar, Ar—$C_{1-6}$-alk(en/yn)yl, Ar—$C_{3-8}$-cycloalk(en)yl, Ar—$C_{3-8}$-cycloalk(en)yl-$C_{1-6}$-alk(en/yn)yl, $C_{1-6}$-alk(en/yn)yloxy, $C_{3-8}$-cycloalk(en)yloxy, $C_{3-8}$-cycloalk(en)yl-$C_{1-6}$-alk(en/yn)yloxy, Ar-oxy, $C_{1-6}$-alk(en/yn)yloxy-carbonyl, halogen, halo-$C_{1-6}$-alk(en/yn)yl, halo-$C_{3-8}$-cycloalk(en)yl, halo-$C_{3-8}$-cycloalk(en)yl-$C_{1-6}$-alk(en/yn)yl, $NR^7R^{7'}$, S—$R^8$ and $SO_2R^8$, or two adjacent $R^5$ together with the aromatic group form a 5-8 membered ring, which optionally contains one or two heteroatoms.

When $R^5$ represents $NR^7R^{7'}$—$C_{1-6}$-alk(en/yn)yl, $NR^7R^{7'}$—$C_{3-8}$-cycloalk(en)yl or $NR^7R^{7'}$—$C_{3-8}$-cycloalk(en)yl-$C_{1-6}$-alk(en/yn)yl then the nitrogen atom is linked to the remainder of the molecule via $C_{1-6}$-alk(en/yn)yl, $C_{3-8}$-cycloalk(en)yl or $C_{3-8}$-cycloalk(en)yl-$C_{1-6}$-alk(en/yn)yl.

In yet another embodiment, the invention relates to compounds of formula I, wherein each $R^5$ is independently selected from the group consisting of a $C_{1-6}$-alk(en/yn)yl, Ar, $C_{1-6}$-alk(en/yn)yloxy, halogen, —$NR^7R^{7'}$, —S—$R^8$ and —$SO_2R^8$, or two adjacent $R^5$ together with the aromatic group form a 5-8 membered ring, which optionally contains one or two heteroatoms.

In a preferred embodiment, the invention relates to compounds of formula I, wherein each $R^5$ is independently selected from the group consisting of a $C_{1-6}$-alk(en/yn)yl, Ar, $C_{1-6}$-alk(en/yn)yloxy, Ar-oxy, $C_{1-6}$-alk(en/yn)yl-heterocycloalk(en)yl, $C_{1-6}$-alk(en/yn)yloxy-carbonyl, halogen, halo-$C_{1-6}$-alk(en/yn)yl, $NR^7R^{7'}$, S—$R^8$ and $SO_2R^8$, or two adjacent $R^5$ together with the aromatic group form a 5-8 membered ring, which optionally contains one or two heteroatoms.

In yet another embodiment, the invention relates to compounds of formula I, wherein one $R^5$ is $C_{1-6}$-alk(en/yn)yl.

In yet another embodiment, the invention relates to compounds of formula I, wherein one $R^5$ is $C_{3-8}$-cycloalk(en)yl.

In yet another embodiment, the invention relates to compounds of formula I, wherein one $R^5$ is $C_{3-8}$-cycloalk(en)yl-$C_{1-6}$-alk(en/yn)yl.

In yet another embodiment, the invention relates to compounds of formula I, wherein one $R^5$ is Ar.

In yet another embodiment, the invention relates to compounds of formula I, wherein one $R^5$ is Ar—$C_{1-6}$-alk(en/yn)yl.

In yet another embodiment, the invention relates to compounds of formula I, wherein no $R^5$ is Ar—$C_{1-6}$-alk(en/yn)yl.

In yet another embodiment, the invention relates to compounds of formula I, wherein one $R^5$ is Ar—$C_{3-8}$-cycloalk(en)yl.

In yet another embodiment, the invention relates to compounds of formula I, wherein no $R^5$ is Ar—$C_{3-8}$-cycloalk(en)yl.

In yet another embodiment, the invention relates to compounds of formula I, wherein one $R^5$ is Ar—$C_{3-8}$-cycloalk(en)yl-$C_{1-6}$-alk(en/yn)yl.

In yet another embodiment, the invention relates to compounds of formula I, wherein no $R^5$ is Ar—$C_{3-8}$-cycloalk(en)yl-$C_{1-6}$-alk(en/yn)yl.

In yet another embodiment, the invention relates to compounds of formula I, wherein one $R^5$ is $C_{3-8}$ alk(en/yn)yloxy.

In yet another embodiment, the invention relates to compounds of formula I, wherein one $R^5$ is $C_{3-8}$-cycloalk(en)yloxy.

In yet another embodiment, the invention relates to compounds of formula I, wherein one $R^5$ is $C_{3-8}$-cycloalk(en)yl-$C_{1-6}$-alk(en/yn)yloxy.

In yet another embodiment, the invention relates to compounds of formula I, wherein one $R^5$ is Ar-oxy.

In yet another embodiment, the invention relates to compounds of formula I, wherein no $R^5$ is Ar-oxy.

In yet another embodiment, the invention relates to compounds of formula I, wherein one $R^5$ is $C_{1-6}$-alk(en/yn)yl-heterocycloalk(en)yl.

In yet another embodiment, the invention relates to compounds of formula I, wherein no $R^5$ is $C_{1-6}$-alk(en/yn)yl-heterocycloalk(en)yl.

In yet another embodiment, the invention relates to compounds of formula I, wherein one $R^5$ is $C_{1-6}$-alk(en/yn)yloxy-carbonyl.

In yet another embodiment, the invention relates to compounds of formula I, wherein no $R^5$ is $C_{1-6}$ alk(en/yn)yloxy-carbonyl.

In yet another embodiment, the invention relates to compounds of formula I, wherein one $R^5$ is a halogen atom.

In yet another embodiment, the invention relates to compounds of formula I, wherein one $R^5$ is halo-$C_{1-6}$-alk(en/yn)yl.

In yet another embodiment, the invention relates to compounds of formula I, wherein no $R^5$ is halo-$C_{1-6}$-alk(en/yn)yl.

In yet another embodiment, the invention relates to compounds of formula I, wherein one $R^5$ is halo-$C_{3-8}$-cycloalk(en)yl.

In yet another embodiment, the invention relates to compounds of formula I, wherein no $R^5$ is halo-$C_{3-8}$-cycloalk(en)yl.

In yet another embodiment, the invention relates to compounds of formula I, wherein one $R^5$ is halo-$C_{3-8}$-cycloalk(en)yl-$C_{1-6}$-alk(en/yn)yl.

In yet another embodiment, the invention relates to compounds of formula I, wherein no $R^5$ is halo-$C_{3-8}$-cycloalk(en)yl-$C_{1-6}$-alk(en/yn)yl.

In yet another embodiment, the invention relates to compounds of formula I, wherein one $R^5$ is $NR^7R^{7'}$.

In yet another embodiment, the invention relates to compounds of formula I, wherein no $R^5$ is $NR^7R^{7'}$.

In yet another embodiment, the invention relates to compounds of formula I, wherein one $R^5$ is S—$R^8$.

In yet another embodiment, the invention relates to compounds of formula I, wherein one $R^5$ is $SO_2R^8$.

In yet another embodiment, the invention relates to compounds of formula I, wherein two adjacent $R^5$ together with the aromatic group form a 5-8 membered ring, which optionally contains one or two heteroatoms.

In a preferred embodiment, the invention relates to compounds of formula I, wherein two adjacent $R^5$ together form —$(CH_2)_{n'}$—$CH_2$—, —CH=CH—$(CH_2)_{m'}$—, —$CH_2$—CH=CH—$(CH_2)_{p'}$—, —CH=CH—CH=CH—, —$(CH_2)_{n'}$—O—, —O—$(CH_2)_{m'}$—O—, —$CH_2$—O—$(CH_2)_{p'}$—O—, —$CH_2$—O—$CH_2$—O—$CH_2$—, —$(CH_2)_{n'}$—S—, —S—$(CH_2)_{m'}$—S—, —$CH_2$—S—$(CH_2)_{p'}$—S—, —$CH_2$—S—$CH_2$—S—$CH_2$—, —$(CH_2)_{n'}$—NH—, —NH—$(CH_2)_{m'}$—NH—, —$CH_2$—NH—$(CH_2)_{p'}$—NH—, —CH=CH—NH—, —O—$(CH_2)_{m'}$—NH—, —$CH_2$—O—$(CH_2)_{p'}$—NH— or —O—$(CH_2)_{p'}$—NH—$CH_2$—, —S—$(CH_2)_{m'}$—NH—, —N=CH—NH—, —N=CH—O— or —N=CH—S—, wherein m' is 1, 2 or 3, n' is 2, 3 or 4 and p' is 1 or 2.

In yet another embodiment, the invention relates to compounds of formula I, wherein two adjacent $R^5$ together form —$CH_2$—O—$CH_2$—.

In yet another embodiment, the invention relates to compounds of formula I, wherein two adjacent $R^5$ together form —CH=CH—CH=CH—.

In yet another embodiment, the invention relates to compounds of formula I, wherein $R^7$ and $R^{7'}$ are independently selected from the group consisting of hydrogen, $C_{1-6}$-alk(en/yn)yl, $C_{3-8}$-cycloalk(en)yl and $C_{3-8}$-cycloalk(en)yl-$C_{1-6}$-alk(en/yn)yl.

In yet another embodiment, the invention relates to compounds of formula I, wherein $R^7$ and $R^{7'}$ are independently selected from the group consisting of hydrogen and $C_{1-6}$-alk(en/yn)yl.

In yet another embodiment, the invention relates to compounds of formula I, wherein one of $R^7$ and $R^{7'}$ are $C_{1-6}$-alk(en/yn)yl, typically $C_{1-3}$-alk(en/yn)yl.

In yet another embodiment, the invention relates to compounds of formula I, wherein both $R^7$ and $R^{7'}$ are $C_{1-6}$-alk(en/yn)yl, typically $C_{1-3}$-alk(en/yn)yl.

In yet another embodiment, the invention relates to compounds of formula I, wherein $R^8$ is selected from the group consisting of hydrogen, $C_{1-6}$-alk(en/yn)yl, $C_{3-8}$-cycloalk(en)yl, $C_{3-8}$-cycloalk(en)yl-$C_{1-6}$-alk(en/yn)yl and Ar.

In a preferred embodiment, the invention relates to compounds of formula I, wherein $R^8$ is selected from the group consisting of $C_{1-6}$-alk(en/yn)yl and Ar.

In a preferred embodiment, the invention relates to compounds of formula I, wherein $R^8$ is $C_{1-6}$-alk(en/yn)yl.

In a preferred embodiment, the invention relates to compounds of formula I, wherein $R^8$ is Ar.

In yet another embodiment, the invention relates to compounds of formula I, wherein X is $SO_2$, q is 0 and $R^3$ is $C_{1-6}$-alk(en/yn)yl, with the proviso that $R^3$ is different from a methyl group.

In yet another embodiment, the invention relates to compounds of formula I, wherein q is 0, $R^3$ is a methyl group and X is different from $SO_2$.

In yet another embodiment, the invention relates to compounds of formula I, wherein X is $SO_2$, q is 1 and U is different from O.

In yet another embodiment, the invention relates to compounds of formula I, wherein s is 1, U is O and X is different from $SO_2$.

In yet another embodiment, the invention relates to compounds of formula I, wherein X is CO, q is 0 and $R^3$ is $C_{1-6}$-alk(en/yn)yl, with the proviso that $R^3$ is different from a methyl group.

In yet another embodiment, the invention relates to compounds of formula I, wherein s is 1, U is different from O, X is CO, q is 0 and $R^3$ is a methyl group.

In yet another embodiment, the invention relates to compounds of formula I, wherein s is 1, U is O, X is CO, q is 0 and $R^3$ is $C_{1-6}$-alk(en/yn)yl, with the proviso that $R^3$ is different from a methyl group.

The molecular weight of the compounds of the invention may vary from compound to compound. The molecular weight of a compound of formula I is typically more than 200 and less than 600, and more typically more than 250 and less than 550.

One aspect of the invention, relates to compounds of general formula XXIX and salts thereof:

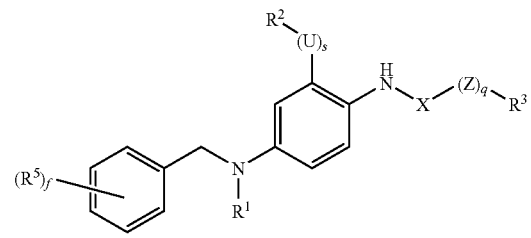

(XXIX)

wherein f, s, q, U, X, Z, $R^1$, $R^2$, $R^3$ and $R^5$ are as defined above, accordingly any of f, s, q, U, X, Z, $R^1$, $R^2$, $R^3$, $R^4$, $R^5$, $R^6$, $R^{6'}$, $R^7$, $R^{7'}$, $R^8$, $R^9$, $R^{9'}$, $R^{10}$, $R^{10'}$, $R^{11}$, $R^{12}$ and $R^{12'}$ are as defined under formula I. Any of the embodiments related to formula I are also embodiments of formula XXIX.

In another embodiment, the invention relates to compounds of the general formula XXIX, wherein f is 0.

In another embodiment, the invention relates to compounds of the general formula XXIX being substituted by one substituent $R^5$, such as in the ortho-, meta- or para-position.

In yet another embodiment, the invention relates to compounds of the general formula XXIX being substituted by two independently selected $R^5$ substituents, such as in the ortho- and para-position, in the meta- and para-position and in the ortho- and meta-position.

In yet another embodiment, the invention relates to compounds of the general formula XXIX being substituted by three independently selected $R^5$ substituents.

Another aspect of the invention relates to compounds of the general formula XXX or salts thereof:

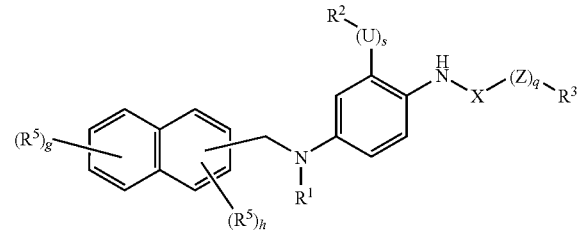

(XXX)

wherein g, h, s, q, U, X, Z, $R^1$, $R^2$, $R^3$ and $R^5$ are as defined above, accordingly any of g, h, s, q, U, X, Z, $R^1$, $R^2$, $R^3$, $R^5$, $R^6$, $R^{6'}$W $R^7$, $R^{7'}$, $R^8$, $R^9$, $R^{9'}$, $R^{10}$, $R^{11}$, $R^{12}$ and $R^{12'}$ are as defined under formula I. Any of the embodiments related to formula I are also embodiments of formula XXX.

In an embodiment, the invention relates to compounds of the general formula XXX, wherein the nitrogen atom is attached to position 1 of the naphtyl group via the methylene group.

In another embodiment, the invention relates to compounds of the general formula XXX, wherein the nitrogen atom is attached to position 2 of the naphtyl group via the methylene group.

In yet another embodiment, the invention relates to compounds of the general formula XXX, wherein g is 0, 1, 2 or 3, typically 0, 1 or 2.

In yet another embodiment, the invention relates to compounds of the general formula XXX, wherein h is 0, 1 or 2, typically 0 or 1.

In yet another embodiment, the invention relates to compounds of the general formula XXX, wherein both g and h are 0.

In yet another embodiment, the invention relates to compounds of the general formula X being substituted by one substituent $R^5$, in a particular aspect thereof g is 0 and h is 1 and in another particular aspect thereof g is 1 and h is 0.

In yet another embodiment, the invention relates to compounds of the general formula XXX being substituted by two independently selected $R^5$ substituents, in a particular aspect thereof g is 0 and h is 2, in another particular aspect thereof g is 1 and h is 1 and in yet another aspect thereof g is 2 and h is 0.

In yet another embodiment, the invention relates to compounds of the general formula XXX being substituted by three independently selected $R^5$ substituents, in a particular aspect thereof g is 0 and h is 3, in another particular aspect thereof g is 1 and h is 2, in yet another aspect thereof g is 2 and h is 1 and in yet another aspect thereof g is 3 and h is 0.

Yet another aspect of the invention relates to compounds of the general formula XXXI or salts thereof:

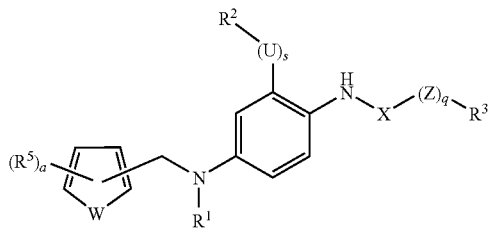

(XXXI)

wherein a, s, q, U, W, X, Z, $R^1$, $R^2$, $R^3$ and $R^5$ are as defined above, accordingly any of a, s, q, U, W, X, Z, $R^1$, $R^2$, $R^3$, $R^5$, $R^6$, $R^{6'}$, $R^7$, $R^{7'}$, $R^8$, $R^9$, $R^{9'}$, $R^{10}$, $R^{10'}$, $R^{11}$, $R^{12}$ and $R^{12'}$ are as defined under formula I. Any of the embodiments related to formula I are also embodiments of formula XXXI.

In an embodiment, the invention relates to compounds of the general formula XXXI, wherein the nitrogen atom is attached to position 2 of the heteroaromatic group via the methylene group.

In another embodiment, the invention relates to compounds of the general formula XXXI, wherein the nitrogen atom is attached to position 3 of the heteroaromatic group via the methylene group.

In yet another embodiment, the invention relates to compounds of the general formula XXXI, wherein a is 0, 1 or 2.

In yet another embodiment, the invention relates to compounds of the general formula XXXI, wherein a is 0.

In yet another embodiment, the invention relates to compounds of the general formula XXXI being substituted by one substituent $R^5$.

In yet another embodiment, the invention relates to compounds of the general formula XXXI being substituted by two independently selected $R^5$ substituents.

Yet another aspect of the invention relates to compounds of the general formula XXXII or salts thereof:

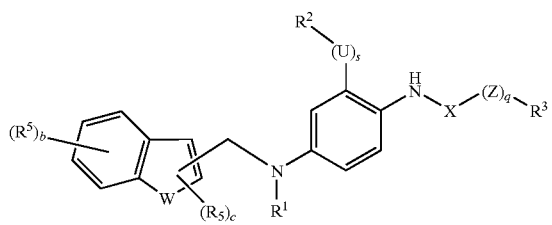

(XXXII)

wherein b, c, s, q, U, W, X, Z, $R^1$, $R^2$, $R^3$ and $R^5$ are as defined above, accordingly any of b, e, s, q, U, W, X, Z, $R^1$, $R^2$, $R^3$, $R^5$, $R^6$, $R^{6'}$, $R^7$, $R^{7'}$, $R^8$, $R^9$, $R^{9'}$, $R^{10}$, $R^{10'}$, $R^{11}$, $R^{12}$ and $R^{12'}$ are as defined under formula I. Any of the embodiments related to formula I are also embodiments of formula XXXII.

In one embodiment, the invention relates to compounds of the general formula XXXII, wherein the nitrogen atom is attached to position 2 of the heteroaromatic group via the methylene group.

In another embodiment, the invention relates to compounds of the general formula XXXII, wherein the nitrogen atom is attached to position 3 of the heteroaromatic group via the methylene group.

In yet another embodiment, the invention relates to compounds of the general formula XXXII, wherein b is 0, 1, 2 or 3, typically 0, 1 or 2.

In yet another embodiment, the invention relates to compounds of the general formula XXXII, wherein c is 0 or 1, typically 0.

In yet another embodiment, the invention relates to compounds of the general formula XXXII, wherein both b and c are 0.

In yet another embodiment, the invention relates to compounds of the general formula XXXII being substituted by one substituent $R^5$, in an aspect thereof b is 0 and c is 1 and in another aspect thereof b is 1 and c is 0.

In yet another embodiment, the invention relates to compounds of the general formula XXXII being substituted by two independently selected $R^5$ substituents, in an aspect thereof b is 1 and c is 1 and in another aspect thereof b is 2 and c is 0.

In yet another embodiment, the invention relates to compounds of the general formula XXXII being substituted by three independently selected $R^5$ substituents, in an aspect thereof b is 2 and c is 1 and in another aspect thereof b is 3 and c is 0.

Yet another aspect of the invention relates to compounds of the general formula XXXIII or salts thereof:

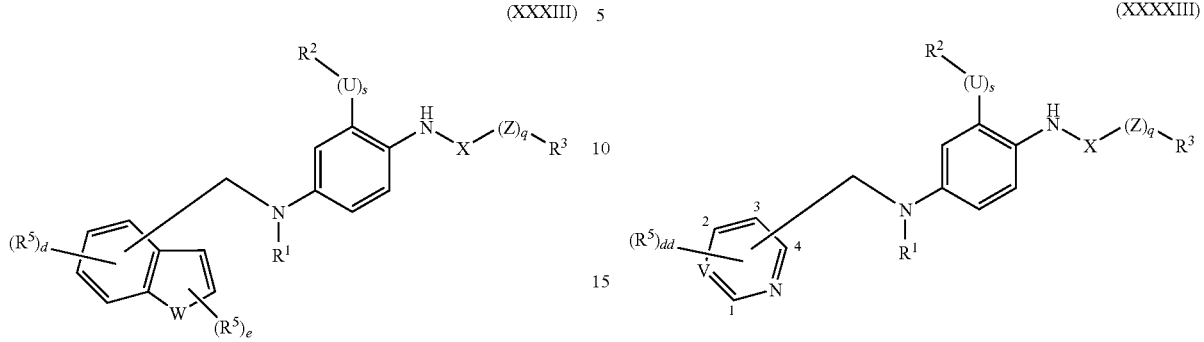

(XXXIII)

wherein d, e, s, q, U, W, X, Z, $R^1$, $R^2$, $R^3$ and $R^5$ are as defined above, accordingly any of d, e, s, q, U, W, X, Z, $R^1$, $R^2$, $R^3$, $R^1$, $R^6$, $R^{6'}$, $R^7$, $R^{7'}$, $R^8$, $R^9$, $R^{9'}$, $R^{10}$, $R^{10'}$, $R^{11}$, $R^{12}$ and $R^{12'}$ are as defined under formula I. Any of the embodiments related to formula I are also embodiments of formula XXXIII.

In an embodiment, the invention relates to compounds of the general formula XXXIII, wherein the nitrogen atom is attached to position 4 of the heteroaromatic group via the methylene group.

In another embodiment, the invention relates to compounds of the general formula XXXIII, wherein the nitrogen atom is attached to position 5 of the heteroaromatic group via the methylene group.

In an embodiment, the invention relates to compounds of the general formula XXXIII, wherein the nitrogen atom is attached to position 6 of the heteroaromatic group via the methylene group.

In another embodiment, the invention relates to compounds of the general formula XXXIII, wherein the nitrogen atom is attached to position 7 of the heteroaromatic group via the methylene group.

In yet another embodiment, the invention relates to compounds of the general formula XXXIII, wherein d is 0, 1 or 2, typically 0 or 1.

In yet another embodiment, the invention relates to compounds of the general formula XXXIII, wherein e is 0, 1 or 2.

In yet another embodiment, the invention relates to compounds of the general formula XXXIII, wherein both d and e are 0.

In yet another embodiment, the invention relates to compounds of the general formula XXXIII being substituted by one substituent $R^5$, in a particular aspect thereof d is 0 and e is 1 and in another particular aspect thereof d is 1 and e is 0.

In yet another embodiment, the invention relates to compounds of the general formula XXXIII being substituted by two independently selected $R^5$ substituents, in a particular aspect thereof d is 0 and e is 2, in another particular aspect thereof d is 1 and e is 1 and in yet another aspect thereof d is 2 and e is 0.

In yet another embodiment, the invention relates to compounds of the general formula XXXIII being substituted by three independently selected $R^5$ substituents, in an aspect thereof d is 1 and e is 2, in another aspect thereof d is 2 and e is 1 and in yet another aspect thereof d is 3 and e is 0.

Yet another aspect of the invention relates to compounds of the general formula XXXXIII or salts thereof:

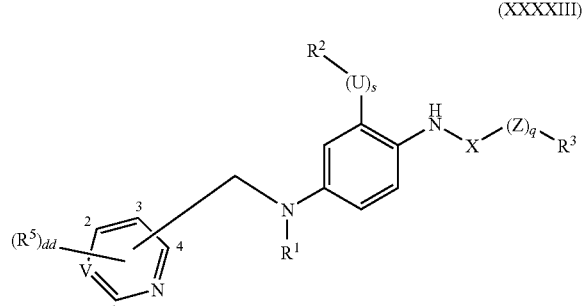

(XXXXIII)

wherein dd, s, q, U, V, X, Z, $R^1$, $R^2$, $R^3$ and $R^5$ are as defined under formula I. Any of the embodiments related to formula I are also embodiments of formula XXXXIII.

In another embodiment, the invention relates to compounds of the general formula XXXIII, wherein V is a carbon atom to which the nitrogen atom is attached via the methylene group.

In an embodiment, the invention relates to compounds of the general formula XXXXIII, wherein the nitrogen atom is attached to the carbon atom, which is indicated with "1", via the methylene group.

In an embodiment, the invention relates to compounds of the general formula XXXXIII, wherein the nitrogen atom is attached to the carbon atom, which is indicated with "2", via the methylene group.

In another embodiment, the invention relates to compounds of the general formula XXXXIII, wherein the nitrogen atom is attached to the carbon atom, which is indicated with "3", via the methylene group.

In another embodiment, the invention relates to compounds of the general formula XXXXIII, wherein the nitrogen atom is attached to the carbon atom, which is indicated with "4", via the methylene group.

In yet another embodiment, the invention relates to compounds of the general formula XXXXIII, wherein dd is 0, 1 or 2, typically 0 or 1. In one aspect of the invention dd is 0. In another aspect of the invention dd is 0.

Yet another aspect of the invention relates to compounds of the general formula XXXXIV or salts thereof:

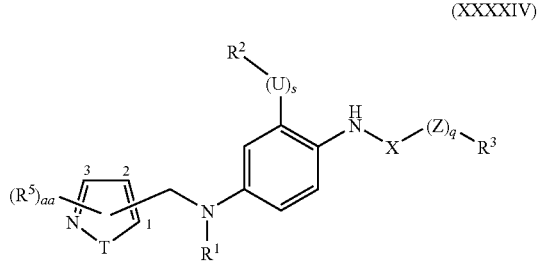

(XXXXIV)

wherein aa, s, q, T, U, X, Z, $R^1$, $R^2$, $R^3$ and $R^5$ are as defined under formula I. Any of the embodiments related to formula I are also embodiments of formula XXXXIV.

In an embodiment, the invention relates to compounds of the general formula XXXXIV, wherein T is a nitrogen atom to which the nitrogen atom is attached via the methylene group.

In an embodiment, the invention relates to compounds of the general formula XXXXIV, wherein the nitrogen atom is attached to the carbon atom, which is indicated with "1", via the methylene group.

In an embodiment, the invention relates to compounds of the general formula XXXXIV, wherein the nitrogen atom is attached to the carbon atom, which is indicated with "2", via the methylene group.

In another embodiment, the invention relates to compounds of the general formula XXXXIV, wherein the nitrogen atom is attached to the carbon atom, which is indicated with "3", via the methylene group.

In yet another embodiment, the invention relates to compounds of the general formula XXXI, wherein aa is 0, 1 or 2. In one embodiment aa is 0. In another embodiment, the general formula XXXXIV are substituted by one substituent $R^5$. In yet another embodiment, the compounds of the general formula XXXI are substituted by two independently selected $R^5$ substituents.

In one particular embodiment, the present invention relates to substituted p-diaminobenzene derivatives of the general formula Ia

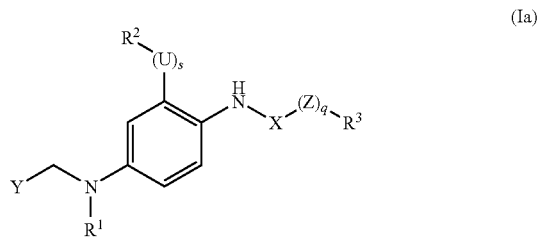

(Ia)

wherein
s is 0 or 1;
U is O, S, $SO_2$, $SO_2NR^{11}$, CO—O or CO—$NR^{11}$; wherein $R^{11}$ is selected from the group consisting of hydrogen, $C_{1-6}$-alk(en/yn)yl, $C_{3-8}$-cycloalk(en)yl, $C_{3-8}$-cycloalk(en)yl-$C_{1-6}$-alk(en/yn)yl; or $R^2$ and $R^{11}$ together with the nitrogen atom form a 5-8 membered saturated or unsaturated ring which optionally contains 1, 2 or 3 further heteroatoms;
q is 0 or 1;
X is CO or $SO_2$; with the proviso that q is 0 when X is $SO_2$;
Z is O or S;
$R^1$ is selected from the group consisting of hydrogen, $C_{1-6}$-alk(en/yn)yl, $C_{3-8}$-cycloalk(en)yl, $C_{3-8}$-cycloalk(en)yl-$C_{1-6}$-alk(en/yn)yl, acyl, hydroxy-$C_{1-6}$-alk(en/yn)yl, hydroxy-$C_{3-8}$-cycloalk(en)yl, hydroxy-$C_{3-8}$-cycloalk(en)yl-$C_{1-6}$-alk(en/yn)yl, halo-$C_{1-6}$-alk(en/yn)yl, halo-$C_{3-8}$-cycloalk(en)yl, halo-$C_{3-8}$-cycloalk(en)yl-$C_{1-6}$-alk(en/yn)yl, cyano-$C_{1-6}$-alk(en/yn)yl, cyano-$C_{3-8}$-cycloalk(en)yl and cyano-$C_{3-8}$-cycloalk(en)yl-$C_{1-6}$-alk(en/yn)yl;
$R^2$ is selected from the group consisting of hydrogen, $C_{1-6}$-alk(en/yn)yl, $C_{3-8}$-cycloalk(en)yl, $C_{3-8}$-cycloalk(en)yl-$C_{1-6}$-alk(en/yn)yl, Ar, Ar—$C_{1-6}$-alk(en/yn)yl, Ar—$C_{3-8}$-cycloalk(en)yl, Ar—$C_{3-8}$-cycloalk(en)yl-$C_{1-6}$-alk(en/yn)yl, acyl, hydroxy-$C_{1-6}$-alk(en/yn)yl, hydroxy-$C_{3-8}$-cycloalk(en)yl, hydroxy-$C_{3-8}$-cycloalk(en)yl-$C_{1-6}$-alk(en/yn)yl, halogen, halo-$C_{1-6}$-alk(en/yn)yl, halo-$C_{3-8}$-cycloalk(en)yl, halo-$C_{3-8}$-cycloalk(en)yl-$C_{1-6}$-alk(en/yn)yl, cyano, cyano-$C_{1-6}$-alk(en/yn)yl, cyano-$C_{3-8}$-cycloalk(en)yl, cyano-$C_{3-8}$-cycloalk(en)yl-$C_{1-6}$-alk(en/yn)yl, $NR^{10}R^{10'}$—$C_{1-6}$-alk(en/yn)yl, $NR^{10}R^{10'}$—$C_{3-8}$-cycloalk(en)yl and $NR^{10}R^{10'}$—$C_{3-8}$-cycloalk(en)yl-$C_{1-6}$-alk(en/yn)yl;
wherein $R^{10}$ and $R^{10'}$ are independently selected from the group consisting of hydrogen, $C_{1-6}$-alk(en/yn)yl, $C_{3-8}$-cycloalk(en)yl, $C_{3-8}$-cycloalk(en)yl-$C_{1-6}$-alk(en/yn)yl, hydroxy-$C_{1-6}$-alk(en/yn)yl, hydroxy-$C_{3-8}$-cycloalk(en)yl, hydroxy-$C_{3-8}$-cycloalk(en)yl-$C_{1-6}$-alk(en/yn)yl, halo-$C_{1-6}$-alk(en/yn)yl, halo-$C_{3-8}$-cycloalk(en)yl, halo-$C_{3-8}$-cycloalk(en)yl-$C_{1-6}$-alk(en/yn)yl, cyano-$C_{1-6}$-alk(en/yn)yl, cyano-$C_{3-8}$-cycloalk(en)yl and cyano-$C_{3-8}$-cycloalk(en)yl-$C_{1-6}$-alk(en/yn)yl, or $R^{10}$ and $R^{10'}$ together with the nitrogen atom form a 5-8 membered saturated or unsaturated ring which optionally contains 1, 2 or 3 further heteroatoms;

provided that when $R^2$ is halogen or cyano then s is 0; and
provided that U is O or S when s is 1 and $R^2$ is a hydrogen atom or acyl;
$R^3$ is selected from the group consisting of $C_{1-6}$-alk(en/yn)yl, $C_{3-8}$-cycloalk(en)yl, heterocycloalk(en)yl, $C_{3-8}$-cycloalk(en)yl-$C_{1-6}$-alk(en/yn)yl, $C_{1-6}$-alk(en/yn)yl-$C_{3-8}$-cycloalk(en)yl, $C_{1-6}$-alk(en/yn)yl-heterocycloalk(en)yl, Ar, Ar—$C_{1-6}$-alk(en/yn)yl, Ar—$C_{3-8}$-cycloalk(en)yl, Ar-heterocycloalk(en)yl, Ar—$C_{3-8}$-cycloalk(en)yl-$C_{1-6}$-alk(en/yn)yl, Ar—$C_{1-6}$-alk(en/yn)yl-$C_{3-8}$-cycloalk(en)yl, Ar—$C_{1-6}$-alk(en/yn)yl-heterocycloalk(en)yl, $C_{1-6}$-alk(en/yn)yloxy-$C_{1-6}$-alk(en/yn)yl, $C_{3-8}$-cycloalk(en)yloxy-$C_{1-6}$-alk(en/yn)yl, $C_{1-6}$-alk(en/yn)yloxy-$C_{3-8}$-cycloalk(en)yl, $C_{1-6}$-alk(en/yn)yloxy-heterocycloalk(en)yl, Ar-oxy-$C_{1-6}$-alk(en/yn)yl, Ar—$C_{1-6}$-alk(en/yn)yloxy-$C_{1-6}$-alk(en/yn)yl, $C_{1-6}$-alk(en/yn)yloxy-carbonyl-$C_{1-6}$ alk(en/yn)yl, $C_{3-8}$-cycloalk(en)yloxy-carbonyl-$C_{1-6}$-alk(en/yn)yl, $C_{3-8}$-cycloalk(en)yl-$C_{1-6}$-alk(en/yn)yloxy-carbonyl-$C_{1-6}$-alk(en/yn)yl, hydroxy-$C_{1-6}$-alk(en/yn)yl, hydroxy-$C_{3-8}$-cycloalk(en)yl, hydroxy-heterocycloalk(en)yl, hydroxy-$C_{3-8}$-cycloalk(en)yl-$C_{1-6}$-alk(en/yn)yl, hydroxy-$C_{1-6}$-alk(en/yn)yl-$C_{3-8}$-cycloalk(en)yl, hydroxy-$C_{1-6}$-alk(en/yn)yl-heterocycloalk(en)yl, halo-$C_{1-6}$-alk(en/yn)yl, halo-$C_{3-8}$-cycloalk(en)yl, halo-heterocycloalk(en)yl, halo-$C_{3-8}$-cycloalk(en)yl-$C_{1-6}$-alk(en/yn)yl, halo-$C_{1-6}$-alk(en/yn)yl-$C_{3-8}$-cycloalk(en)yl, halo-$C_{1-6}$-alk(en/yn)yl-heterocycloalk(en)yl, halo-$C_{1-6}$ alk(en/yn)yl-Ar, halo-$C_{3-8}$-cycloalk(en)yl-Ar, halo-$C_{3-8}$-cycloalk(en)yl-$C_{1-6}$-alk(en/yn)yl-Ar, halo-$C_{1-6}$-alk(en/yn)yl-$C_{3-8}$-cycloalk(en)yl-Ar, cyano-$C_{1-6}$-alk(en/yn)yl, cyano-$C_{3-8}$-cycloalk(en)yl, cyano-heterocycloalk(en)yl, cyano-$C_{3-8}$-cycloalk(en)yl-$C_{1-6}$-alk(en/yn)yl, cyano-$C_{1-6}$-alk(en/yn)yl-$C_{3-8}$-cycloalk(en)yl, cyano-$C_{1-6}$-alk(en/yn)yl-heterocycloalk(en)yl, acyl-$C_{1-6}$-alk(en/yn)yl, acyl-$C_{3-8}$-cycloalk(en)yl, acyl-heterocycloalk(en)yl, acyl-$C_{3-8}$-cycloalk(en)yl-$C_{1-6}$-alk(en/yn)yl, acyl-$C_{1-6}$-alk(en/yn)yl-$C_{3-8}$-cycloalk(en)yl, acyl-$C_{1-6}$-alk(en/yn)yl-heterocycloalk(en)yl, —$NR^{12}R^{12'}$; wherein $R^{12}$ and $R^{12'}$ are independently selected from the group consisting of hydrogen, $C_{1-6}$-alk(en/yn)yl, $C_{3-8}$-cycloalk(en)yl, $C_{3-8}$-cycloalk(en)yl-$C_{1-6}$-alk(en/yn)yl, hydroxy-$C_{1-6}$-alk(en/yn)yl, hydroxy-$C_{3-8}$-cycloalk(en)yl, hydroxy-$C_{3-8}$-cycloalk(en)yl-$C_{1-6}$-alk(en/yn)yl, halo-$C_{1-6}$-alk(en/yn)yl, halo-$C_{3-8}$-cycloalk(en)yl, halo-$C_{3-8}$-cycloalk(en)yl-$C_{1-6}$-alk(en/yn)yl, cyano-$C_{1-6}$-alk(en/yn)yl, cyano-$C_{3-8}$-cycloalk(en)yl and cyano-$C_{3-8}$-cycloalk(en)yl-$C_{1-6}$-alk(en/yn)yl, or $R^{12}$ and $R^{12'}$ together with the nitrogen atom form a 5-8 membered saturated or unsaturated ring which optionally contains 1, 2 or 3 further heteroatoms; and
Y represents a group of formula XXIV, XXV, XXVI, XXVII or XXVIII:

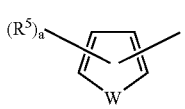

XXIV

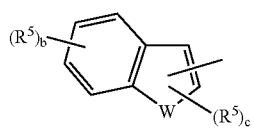

XXV

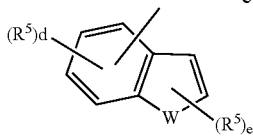

XXVI

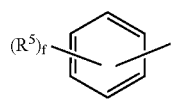

XXVII

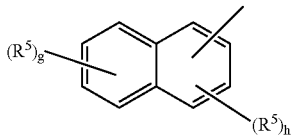

XXVIII wherein
the line represents a bond attaching the group represented by Y to the carbon atom;
W is O or S;
a is 0, 1, 2 or 3;
b is 0, 1, 2, 3 or 4;
c is 0 or 1;
d is 0, 1, 2 or 3;
e is 0, 1 or 2;
f is 0, 1, 2, 3, 4 or 5;
g is 0, 1, 2, 3 or 4;
h is 0, 1, 2 or 3; and
each $R^5$ is independently selected from the group consisting of a $C_{1-6}$-alk(en/yn)yl, $C_{3-8}$-cycloalk(en)yl, $C_{3-8}$-cycloalk(en)yl-$C_{1-6}$-alk(en/yn)yl, Ar, Ar—$C_{1-6}$-alk(en/yn)yl, acyl, $C_{1-6}$-alk(en/yn)yloxy, $C_{3-8}$-cycloalk(en)yloxy, $C_{3-8}$-cycloalk(en)yl-$C_{1-6}$-alk(en/yn)yloxy, halogen, halo-$C_{1-6}$-alk(en/yn)yl, halo-$C_{3-8}$-cycloalk(en)yl, halo-$C_{3-8}$-cycloalk(en)yl-$C_{1-6}$-alk(en/yn)yl, —CO—$NR^6R^{6'}$, cyano, cyano-$C_{1-6}$-alk(en/yn)yl, cyano-$C_{3-8}$-cycloalk(en)yl, cyano-$C_{3-8}$-cycloalk(en)yl-$C_{1-6}$-alk(en/yn)yl, —$NR^7R^{7'}$, —S—$R^8$ and —$SO_2R^8$, or two adjacent $R^5$ together with the aromatic group form a 5-8 membered ring which optionally contains one or two heteroatoms;
$R^6$ and $R^{6'}$ are independently selected from the group consisting of hydrogen, $C_{1-6}$-alk(en/yn)yl, $C_{3-8}$-cycloalk(en)yl, $C_{3-8}$-cycloalk(en)yl-$C_{1-6}$-alk(en/yn)yl and Ar;
$R^7$ and $R^{7'}$ are independently selected from the group consisting of hydrogen, $C_{1-6}$-alk(en/yn)yl, $C_{3-8}$-cycloalk(en)yl, $C_{3-8}$-cycloalk(en)yl-$C_{1-6}$-alk(en/yn)yl, Ar and acyl; and
$R^8$ is selected from the group consisting of hydrogen, $C_{1-6}$-alk(en/yn)yl, $C_{3-8}$-cycloalk(en)yl, $C_{3-8}$-cycloalk(en)yl-$C_{1-6}$-alk(en/yn)yl, Ar and —$NR^9R^{9'}$; wherein $R^9$ and $R^{9'}$ are independently selected from the group consisting of hydrogen, $C_{1-6}$-alk(en/yn)yl, $C_{3-8}$-cycloalk(en)yl and $C_{3-8}$-cycloalk(en)yl-$C_{1-6}$-alk(en/yn)yl;
or salts thereof.

In one embodiment, the compounds of the following list and salts thereof are preferred:
{4-[(Benzofuran-2-ylmethyl)-amino]-2-methylphenyl}-carbamic acid propyl ester;
{4-[(5-Chloro-thiophen-2-ylmethyl)-amino]-2-methylphenyl}-carbamic acid ethyl ester;
{4-[(Benzo[b]thiophen-2-ylmethyl)-amino]-2-methylphenyl}-carbamic acid ethyl ester;
{2-Methyl-4-[(5-phenyl-thiophen-2-ylmethyl)-amino]-phenyl}-carbamic acid propyl ester;
[4-(4-Isopropyl-benzylamino)-2-methylphenyl]-carbamic acid ethyl ester;
[4-(4-Fluoro-benzylamino)-2-methylphenyl]-carbamic acid propyl ester;
(4-{[4-(4-Chloro-benzenesulfonyl)-3-methyl-thiophen-2-ylmethyl]-amino}-2-methylphenyl)-carbamic acid propyl ester;
{4-[(5-Methyl-thiophen-2-ylmethyl)-amino]-2-methylphenyl}-carbamic acid propyl ester;
{4-[(5-Bromo-thiophen-2-ylmethyl)-amino]-2-methylphenyl}-carbamic acid propyl ester;
{4-[(5-Chloro-thiophen-2-ylmethyl)-amino]-2-methylphenyl}-carbamic acid propyl ester;
{4-[(Benzo[b]thiophen-2-ylmethyl)-amino]-2-methylphenyl}-carbamic acid propyl ester;
{2-Methyl-4-[(5-phenyl-thiophen-2-ylmethyl)-amino]-phenyl}-carbamic acid propyl ester;
[4-(4-Isopropyl-benzylamino)-2-methylphenyl]-carbamic acid propyl ester;
{4-[(5-Bromo-thiophen-2-ylmethyl)-amino]-2-chlorophenyl}-carbamic acid ethyl ester;
{4-[(5-Chloro-thiophen-2-ylmethyl)-amino]-2-chlorophenyl}-carbamic acid ethyl ester;
{4-[Benzo[b]thiophen-2-ylmethyl)-amino]-2-chlorophenyl}-carbamic acid ethyl ester;
[2-Chloro-4-(4-isopropyl-benzylamino)-phenyl]-carbamic acid ethyl ester;
[2-Chloro-4-(4-fluoro-benzylamino)-phenyl]-carbamic acid propyl ester;
2-Chloro-4-{[4-(4-chloro-benzenesulfonyl)-3-methyl-thiophen-2-ylmethyl]-amino}-phenyl)-carbamic acid propyl ester;
{4-[(5-Methyl-thiophen-2-ylmethyl)-amino]-2-chlorophenyl}-carbamic acid propyl ester;
{4-[(5-Bromo-thiophen-2-ylmethyl)-amino]-2-chlorophenyl}-carbamic acid propyl ester;
{2-Chloro-4-[(5-chloro-thiophen-2-ylmethyl)-amino]-phenyl}-carbamic acid propyl ester;
{4-[(Benzo[b]thiophen-2-ylmethyl)-amino]-2-chlorophenyl}-carbamic acid propyl ester;
{4-[(Benzofuran-2-yl-4-ethyl)-amino]-2-chlorophenyl}-carbamic acid propyl ester;
{4-[(5-Chloro-thiophen-2-ylmethyl)-amino]-2-cyanophenyl}-carbamic acid ethyl ester;
{4-[(Benzo[b]thiophen-2-ylmethyl)-amino]-2-methoxyphenyl}-carbamic acid methyl ester;
{4-[(5-Bromo-thiophen-2-ylmethyl)-amino]-2-methoxyphenyl}-carbamic acid isopropyl ester;
{4-[(4-Fluoro-benzyl)-(methyl)amino]-2-methoxyphenyl}-carbamic acid propyl ester;
[4-(Benzo[b]thiophen-2-ylmethyl-(methyl)amino)-2-methoxy-phenyl]-carbamic acid propyl ester;
{4-[(5-Chloro-thiophen-2-ylmethyl)-(methyl)amino]-2-methoxy-phenyl}-carbamic acid propyl ester;
{4[(5-Bromo-thiophen-2-ylmethyl)-(methyl)amino]-2-methoxy-phenyl}-carbamic acid propyl ester;
{2-Methoxy-4-[methyl-(5-methyl-thiophen-2-ylmethyl)-amino]-phenyl}-carbamic acid propyl ester;
{4-[(4-Fluorobenzyl)-(methyl)-amino]-2-isopropoxyphenyl}-carbamic acid ethyl ester;
[4-(3-Fluorobenzylamino)-2-methoxyphenyl]-carbamic acid ethyl ester;
[4-(4-Isopropylbenzylamino)-2-methoxyphenyl]-carbamic acid ethyl ester;
{2-Methoxy-4-[(3-methylthiophen-2-ylmethyl)-amino]-phenyl}-carbamic acid ethyl ester;
[4-(2,4-Difluorobenzylamino)-2-methoxyphenyl]-carbamic acid ethyl ester;

[2-Cyclopentyloxy-4-(4-methoxybenzylamino)-phenyl]-carbamic acid ethyl ester;
[2-Cyclopentyloxy-4-(3-fluoro-2-methylbenzylamino)-phenyl]-carbamic acid ethyl ester;
[4-(3-Fluoro-2-methylbenzylamino)-2-phenethyloxyphenyl]-carbamic acid ethyl ester;
[2-Benzyloxy-4-(3-fluoro-2-methylbenzylamino)-phenyl]-carbamic acid ethyl ester;
[2-Benzyloxy-4-(4-methylsulfanylbenzylamino)-phenyl]-carbamic acid ethyl ester;
{4-[Benzo[b]thiophen-3-dimethyl)-amino]-2-cyclopentyloxyphenyl}-carbamic acid ethyl ester;
[4-(3-Fluoro-2-methylbenzylamino)-2-isopropoxyphenyl]-carbamic acid ethyl ester;
[2-Benzyloxy-4-(3-methoxybenzylamino)-phenyl]-carbamic acid ethyl ester;
{4-[(Benzo[1,3]dioxol-5-ylmethyl)-amino]-2-isopropoxyphenyl}-carbamic acid ethyl ester;
{4-[(5-Bromo-thiophen-2-ylmethyl)-amino]-phenyl}-carbamic acid propyl ester;
{4-[(5-Chloro-thiophen-2-ylmethyl)-amino]-phenyl}-carbamic acid propyl ester;
[2-Cyano-4-(4-isopropylbenzylamino)-phenyl]-carbamic acid ethyl ester;
{4-[(5-Bromo-thiophen-2-ylmethyl)-(methyl)amino]-2-methylphenyl}-carbamic acid propyl ester;
{4-[(4-Isopropylbenzyl)-(methyl)amino]-2-methylphenyl}-carbamic acid propyl ester;
{2-Methyl-4-[methyl-(4-trifluoromethyl-benzyl)-amino]-phenyl}-carbamic acid propyl ester;
{2-Methyl-4-[methyl-(4-methylsulfanyl-benzyl)-amino]-phenyl}-carbamic acid propyl ester;
{4-[(4-tert-Butyl-benzyl)-(methyl)amino]-2-chlorophenyl}-carbamic acid ethyl ester;
{2-Chloro-4-[methyl-(4-trifluoromethyl-benzyl)-amino]-phenyl}-carbamic acid ethyl ester;
{2-Chloro-4-[methyl-(4-methylsulfanyl-benzyl)-amino]-phenyl}-carbamic acid ethyl ester;
{4-[(5-Bromo-thiophen-2-ylmethyl)-(methyl)amino]-2-chlorophenyl}-carbamic acid propyl ester;
{2-Chloro-4-[(5-chloro-thiophen-2-ylmethyl)-(methyl)amino]-phenyl}-carbamic acid propyl ester;
{4-[(4-tert-Butyl-benzyl)-(methyl)amino]-2-chlorophenyl}-carbamic acid propyl ester;
{2-Chloro-4-[methyl-(4-trifluoromethyl-benzyl)-amino]-phenyl}-carbamic acid propyl ester;
{4-[(5-Bromo-thiophen-2-ylmethyl)-(methyl)amino]-2-trifluoromethyl-phenyl}-carbamic acid ethyl ester;
{4-[(5-Chloro-thiophen-2-ylmethyl)-(methyl)amino]-2-trifluoromethyl-phenyl}-carbamic acid ethyl ester;
{4[(4-Isopropyl-benzyl)-(methyl)amino]-2-trifluoromethyl-phenyl}-carbamic acid ethyl ester;
{4-[(4-tert-Butyl-benzyl)-(methyl)amino]-2-trifluoromethyl-phenyl}-carbamic acid ethyl ester;
{4-[Methyl-(4-trifluoromethyl-benzyl)-amino]-2-trifluoromethyl-phenyl}-carbamic acid ethyl ester;
{4-[Methyl-(4-methylsulfanyl-benzyl)-amino]-2-trifluoromethyl-phenyl}-carbamic acid ethyl ester;
{4-[(5-Bromo-thiophen-2-ylmethyl)-(methyl)amino]-2-trifluoromethyl-phenyl}-carbamic acid propyl ester;
{4-[(5-Chloro-thiophen-2-ylmethyl)-(methyl)amino]-2-trifluoromethyl-phenyl}carbamic acid propyl ester;
{4-[(4-Isopropyl-benzyl)-(methyl)amino]-2-trifluoromethyl-phenyl}-carbamic acid propyl ester;
{4-[(4-tert-Butyl-benzyl)-(methyl)amino]-2-trifluoromethyl-phenyl}-carbamic acid propyl ester;
{4-[Methyl-(4-trifluoromethyl-benzyl)-amino]-2-trifluoromethyl-phenyl}-carbamic acid propyl ester;
{4-[Methyl-(4-methylsulfanyl-benzyl)-amino]-2-trifluoromethyl-phenyl}-carbamic acid propyl ester;
{4-[(5-Bromo-thiophen-2-ylmethyl)-(methyl)amino]-2-cyanophenyl}-carbamic acid propyl ester;
{4-[(4-tert-Butyl-benzyl)-(methyl)amino]-2-cyanophenyl}-carbamic acid propyl ester;
{2-Cyano-4-[methyl-(4-trifluoromethyl-benzyl)-amino]-phenyl}-carbamic acid propyl ester;
{2-Bromo-4-[(5-bromo-thiophen-2-ylmethyl)-(methyl)amino]-phenyl}-carbamic acid propyl ester;
{2-Bromo-4-[(5-chloro-thiophen-2-ylmethyl)-(methyl)amino]-phenyl}-carbamic acid propyl ester;
{2-Bromo-4-[(4-isopropylbenzyl)-(methyl)amino]-phenyl}-carbamic acid propyl ester;
{2-Bromo-4-[(4-tert-butyl-benzyl)-(methyl)amino]-phenyl}-carbamic acid propyl ester;
{2-Bromo-4-[methyl-(4-trifluoromethyl-benzyl)-amino]-phenyl}-carbamic acid propyl ester;
[2-Iodo-4-(4-isopropyl-benzylamino)-phenyl]-carbamic acid propyl ester;
[4-(4-tert-Butyl-benzylamino)-2-iodophenyl]-carbamic acid propyl ester;
[2-Iodo-4-(4-trifluoromethyl-benzylamino)-phenyl]-carbamic acid propyl ester;
[2-Iodo-4-(4-methylsulfanyl-benzylamino)-phenyl]-carbamic acid propyl ester;
{2-Iodo-4-[4-(4-methylpiperazin-1-yl)-benzylamino]-phenyl}-carbamic acid propyl ester;
{4-[(5-Bromo-thiophen-2-ylmethyl)-amino]-2-trifluoromethyl-phenyl}-carbamic acid ethyl ester;
{4[(5-Chloro-thiophen-2-ylmethyl)-amino]-2-trifluoromethyl-phenyl}-carbamic acid ethyl ester;
[4-(4-tert-Butyl-benzylamino)-2-trifluoromethyl-phenyl]-carbamic acid ethyl ester;
[4-(4-Methylsulfanyl-benzylamino)-2-trifluoromethyl-phenyl]-carbamic acid ethyl ester;
{4-[(5-Bromo-thiophen-2-ylmethyl)-amino]-2-trifluoromethyl-phenyl}-carbamic acid propyl ester;
[4-(4-Isopropylbenzylamino)-2-trifluoromethyl-phenyl]-carbamic acid propyl ester;
[4-(4-tert-Butyl-benzylamino)-2-trifluoromethyl-phenyl]-carbamic acid propyl ester;
[2-Trifluoromethyl-4-(4-trifluoromethyl-benzylamino)-phenyl]-carbamic acid propyl ester;
[4-(4-Dimethylamino-benzylamino)-2-trifluoromethyl-phenyl]-carbamic acid propyl ester;
[4-(4-Methylsulfanyl-benzylamino)-2-trifluoromethyl-phenyl]-carbamic acid propyl ester;
{4-[(5-Bromo-thiophen-2-ylmethyl)-amino]-2-cyanophenyl}-carbamic acid propyl ester;
{4-[(5-Chloro-thiophen-2-ylmethyl)-amino]-2-cyanophenyl}-carbamic acid propyl ester;
[2-Cyano-4-(4-trifluoromethyl-benzylamino)-phenyl]-carbamic acid propyl ester;
{2-Bromo-4-[(5-bromo-thiophen-2-ylmethyl)-amino]-phenyl}-carbamic acid propyl ester;
{2-Bromo-4-[(5-chloro-thiophen-2-ylmethyl)-amino]-phenyl}-carbamic acid propyl ester;
[2-Bromo-4-(4-isopropylbenzylamino)-phenyl]-carbamic acid propyl ester;
[2-Bromo-4-(4-tert-butyl-benzylamino)-phenyl]-carbamic acid propyl ester;
[2-Bromo-4-(4-trifluoromethyl-benzylamino)-phenyl]-carbamic acid propyl ester;

[2-Bromo-4-(4-methylsulfanyl-benzylamino)-phenyl]-carbamic acid propyl ester;
N-{4-[(5-Bromo-thiophen-2-ylmethyl)-amino]-2-methoxyphenyl}-butyramide;
N-{4-[(5-Chloro-thiophen-2-ylmethyl)-amino]-2-methoxyphenyl}-butyramide;
N-[4-(4-Isopropylbenzylamino)-2-methoxyphenyl]-butyramide;
N-[4-(4-tert-Butyl-benzylamino)-2-methoxyphenyl]-butyramide;
N-[2-Methoxy-4-(4-trifluoromethyl-benzylamino)-phenyl]-butyramide;
{4-[(5-Chloro-thiophen-2-ylmethyl)-amino]-2-furan-2-yl-phenyl}-carbamic acid propyl ester;
[2-Furan-2-yl-4-(4-isopropylbenzylamino)-phenyl]-carbamic acid propyl ester;
[5-(4-Fluorobenzylamino)-biphenyl-2-yl]-carbamic acid propyl ester;
{5-[(5-Chloro-thiophen-2-ylmethyl)-amino]-biphenyl-2-yl}-carbamic acid propyl ester;
[5-(4-Isopropylbenzylamino)-biphenyl-2-yl]-carbamic acid propyl ester;
N-{2-Chloro-4-[(5-chloro-thiophen-2-ylmethyl)-(methyl)amino]-phenyl}-2-phenylacetamide;
N-{2-Chloro-4-[(5-chloro-thiophen-2-ylmethyl)-(methyl)amino]-phenyl}-3,3-dimethylbutyramide;
N-{2-Chloro-4-[(5-chloro-thiophen-2-ylmethyl)-(methyl)amino]-phenyl}-3-phenylpropionamide;
N-{2-Chloro-4-[(5-chloro-thiophen-2-ylmethyl)-(methyl)amino]-phenyl}-butyramide;
Pentanoic acid {2-chloro-4-[(5-chloro-thiophen-2-ylmethyl)-(methyl)amino]-phenyl}-amide;
Cyclopropanecarboxylic acid {2-chloro-4-[(5-chloro-thiophen-2-ylmethyl)-(methyl)amino]-phenyl}-amide;
Cyclobutanecarboxylic acid {2-chloro-4-[(5-chloro-thiophen-2-ylmethyl)-(methyl)amino]-phenyl}-amide;
Cyclopentanecarboxylic acid {2-chloro-4-[(5-chloro-thiophen-2-ylmethyl)-(methyl)amino]-phenyl}-amide;
Cyclohexanecarboxylic acid {2-chloro-4-[(5-chloro-thiophen-2-ylmethyl)-(methyl)amino]-phenyl}-amide;
N-{2-Chloro-4-[(5-chloro-thiophen-2-ylmethyl)-(methyl)amino]-phenyl}-2-thiophen-2-yl-acetamide;
N-{2-Chloro-4-[(5-chloro-thiophen-2-ylmethyl)-(methyl)amino]-phenyl}-2-(3-methoxy)-phenyl)-acetamide;
N-{2-Chloro-4-[(5-chloro-thiophen-2-ylmethyl)-(methyl)amino]-phenyl}-2-(4-chloro-phenyl)-acetamide;
N-{2-Chloro-4-[(5-chloro-thiophen-2-ylmethyl)-(methyl)amino]-phenyl}-2-(4-methoxy-phenyl)-acetamide;
N-{2-Chloro-4-[(5-chloro-thiophen-2-ylmethyl)-(methyl)amino]-phenyl}-2-(4-fluoro-phenyl)-acetamide;
N-{2-Chloro-4-[(5-chloro-thiophen-2-ylmethyl)-(methyl)amino]-phenyl}-3-cyclohexylpropionamide;
N-{2-Chloro-4[(5-chloro-thiophen-2-ylmethyl)-amino]-phenyl}-2,2-dimethylpropionamide;
N-{2-Chloro-4-[(5-chloro-thiophen-2-ylmethyl)-amino]-phenyl}-2-phenoxyacetamide;
N-{2-Chloro-4-[(5-chloro-thiophen-2-ylmethyl)-amino]-phenyl}-2-phenylacetamide;
N-{2-Chloro-4-[(5-chloro-thiophen-2-ylmethyl)-amino]-phenyl}-3,3-dimethylbutyramide;
N-{2-Chloro-4-[(5-chloro-thiophen-2-ylmethyl)-amino]-phenyl}-butyramide;
Pentanoic acid {2-chloro-4-[(5-chloro-thiophen-2-ylmethyl)-amino]-phenyl}-amide;
Cyclopropanecarboxylic acid {2-chloro-4-[(5-chloro-thiophen-2-ylmethyl)-amino]-phenyl}-amide;
Cyclobutanecarboxylic acid {2-chloro-4-[(5-chloro-thiophen-2-ylmethyl)-amino]-phenyl}-amide;
Cyclopentanecarboxylic acid {2-chloro-4-[(5-chloro-thiophen-2-ylmethyl)-amino]-phenyl}-amide;
Cyclohexanecarboxylic acid {2-chloro-4-[(5-chloro-thiophen-2-ylmethyl)-amino]-phenyl}-amide;
N-{2-Chloro-4-[(5-chloro-thiophen-2-ylmethyl)-amino]-phenyl}-2-thiophen-2-yl-acetamide;
N-{2-Chloro-4-[(5-chloro-thiophen-2-ylmethyl)-amino]-phenyl}-2-(3-methoxyphenyl)-acetamide;
N-{2-Chloro-4-[(5-chloro-thiophen-2-ylmethyl)-amino]-phenyl}-2-(4-chlorophenyl)-acetamide;
N-{2-Chloro-4-[(5-chloro-thiophen-2-ylmethyl)-amino]-phenyl}-2-(4-methoxyphenyl)-acetamide;
N-{2-Chloro-4-[(5-chloro-thiophen-2-ylmethyl)-amino]-phenyl}-2-(4-fluorophenyl)-acetamide;
2,3-Dihydro-benzo[1,4]dioxine-6-carboxylic acid {2-chloro-4-[(5-chloro-thiophen-2-ylmethyl)-amino]-phenyl}-amide;
2,3-Dihydro-benzofuran-5-carboxylic acid {2-chloro-4-[(5-chloro-thiophen-2-ylmethyl)-amino]-phenyl}-amide;
N-{2-Chloro-4-[(5-chloro-thiophen-2-ylmethyl)-amino]-phenyl}-3-cyclohexylpropionamide;
N-{4-[(5-Chloro-thiophen-2-ylmethyl)-(methyl)amino]-2-methyl-phenyl}-2,2-dimethylpropionamide;
N-{4-[(5-Chloro-thiophen-2-ylmethyl)-(methyl)amino]-2-methyl-phenyl}-2-phenylacetamide;
N-{4-[(5-Chloro-thiophen-2-ylmethyl)-(methyl)amino]-2-methyl-phenyl}-3,3-dimethylbutyramide;
N-{4-[(5-Chloro-thiophen-2-ylmethyl)-(methyl)amino]-2-methyl-phenyl}-3-phenylpropionamide;
N-{4-[(5-Chloro-thiophen-2-ylmethyl)-(methyl)amino]-2-ylmethyl-phenyl}-butyramide;
2,2,2-Trichloro-N-{4-[(5-chloro-thiophen-2-ylmethyl)-(methyl)amino]-2-methyl-phenyl}-acetamide;
Cyclopropanecarboxylic acid {4-[(5-chloro-thiophen-2-ylmethyl)-(methyl)amino]-2-methyl-phenyl}-amide;
Cyclobutanecarboxylic acid {4-[(5-chloro-thiophen-2-ylmethyl)-(methyl)amino]-2-methylphenyl}-amide;
Cyclopentanecarboxylic acid {4-[(5-chloro-thiophen-2-ylmethyl)-(methyl)amino]-2-methylphenyl}-amide;
Cyclohexanecarboxylic acid {4-[(5-chloro-thiophen-2-ylmethyl)-(methyl)amino]-2-methylphenyl}-amide;
N-{4-[(5-Chloro-thiophen-2-ylmethyl)-(methyl)amino]-2-methylphenyl}-2-thiophen-2-yl-acetamide;
N-{4-[(5-Chloro-thiophen-2-ylmethyl)-(methyl)amino]-2-methylphenyl}-2-(3-methoxyphenyl)-acetamide;
N-{4-[(5-Chloro-thiophen-2-ylmethyl)-(methyl)amino]-2-methylphenyl}-malonamic acid methyl ester;
2-(4-Chlorophenyl)-N-{4-[(5-chloro-thiophen-2-ylmethyl)-(methyl)amino]-2-methylphenyl}-acetamide;
N-{4-[(5-Chloro-thiophen-2-ylmethyl)-(methyl)amino]-2-methylphenyl}-2-(4-methoxyphenyl)-acetamide;
N-{4-[(5-Chloro-thiophen-2-ylmethyl)-(methyl)amino]-2-methylphenyl}-2-(4-fluorophenyl)-acetamide;
N-{4[(5-Chloro-thiophen-2-ylmethyl)-(methyl)amino]-2-methylphenyl}-3-cyclohexylpropionamide;
{2-Chloro-4-[(5-chloro-thiophen-2-ylmethyl)-(methyl)amino]-phenyl}-carbamic acid phenyl ester;
{2-Chloro-4-[(5-chloro-thiophen-2-ylmethyl)-(methyl)amino]-phenyl}-carbamic acid benzyl ester;
{2-Chloro-4-[(5-chloro-thiophen-2-ylmethyl)-(methyl)amino]-phenyl}-carbamic acid isobutyl ester;
{2-Chloro-4-[(5-chloro-thiophen-2-ylmethyl)-(methyl)amino]-phenyl}-carbamic acid butyl ester;
{2-Chloro-4-[(5-chloro-thiophen-2-ylmethyl)-(methyl)amino]-phenyl}-carbamic acid hexyl ester;

{2-Chloro-4-[(5-chloro-thiophen-2-ylmethyl)-(methyl)amino]-phenyl}-carbamic acid 4-nitrobenzyl ester;
{2-Chloro-4-[(5-chloro-thiophen-2-ylmethyl)-(methyl)amino]-phenyl}-carbamic acid but-3-enyl ester;
{2-Chloro-4[(5-chloro-thiophen-2-ylmethyl)-(methyl)amino]-phenyl}-carbamic acid but-2-ynyl ester;
{2-Chloro-4-[(5-chloro-thiophen-2-ylmethyl)-(methyl)amino]-phenyl}-carbamic acid 2,2-dimethylpropyl ester;
{2,2-Chloro-4-[(5-chloro-thiophen-2-ylmethyl)-(methyl)amino]-phenyl}-carbamic acid 2-chlorobenzyl ester;
{2-Chloro-4-[(5-chloro-thiophen-2-ylmethyl)-(methyl)amino]-phenyl}-carbamic acid 3-chloropropyl ester;
{2-Chloro-4-[(5-chloro-thiophen-2-ylmethyl)-(methyl)amino]-phenyl}-carbamic acid 2-benzyloxyethyl ester;
3-{2-Chloro-4-[(5-chloro-thiophen-2-ylmethyl)-(methyl)amino]-phenyl}-1-methyl-1-propyl-urea;
1-{2-Chloro-4-[(5-chloro-thiophen-2-ylmethyl)-(methyl)amino]-phenyl}-3-(2-fluorophenyl)-urea;
N-{2-Chloro-4-[(5-chloro-thiophen-2-ylmethyl)-(methyl)amino]-phenyl}-2,2,2-trifluoroacetamide; and
N-{2-Chloro-4-[(5-chloro-thiophen-2-ylmethyl)-amino]-phenyl}-2,2,2-trifluoroacetamide.

In another embodiment, the compounds of the following list and salts thereof are preferred:
{4-[(Benzofuran-2-ylmethyl)-amino]-2-methylphenyl}-carbamic acid propyl ester;
{4-[(5-Chloro-thiophen-2-ylmethyl)-amino]-2-methylphenyl}-carbamic acid ethyl ester;
{4-[(Benzo[b]thiophen-2-ylmethyl)-amino]-2-methylphenyl}-carbamic acid ethyl ester;
{2-Methyl-4-[(5-phenyl-thiophen-2-ylmethyl)-amino]-phenyl}-carbamic acid ethyl ester;
[4-(4-Isopropyl-benzylamino)-2-methylphenyl]-carbamic acid ethyl ester;
[4-(4-Fluoro-benzylamino)-2-methylphenyl]-carbamic acid propyl ester;
(4-{[4-(4-Chloro-benzenesulfonyl)-3-methyl-thiophen-2-ylmethyl]-amino}-2-methylphenyl)-carbamic acid propyl ester;
{4-[(5-Methyl-thiophen-2-ylmethyl)-amino]-2-methylphenyl}-carbamic acid propyl ester;
{4-[(5-Bromo-thiophen-2-ylmethyl)-amino]-2-methylphenyl}-carbamic propyl ester;
{4-[(5-Chloro-thiophen-2-ylmethyl)-amino]-2-methylphenyl}-carbamic acid propyl ester;
{4-[(Benzo[b]thiophen-2-ylmethyl)-amino]-2-methylphenyl}-carbamic acid propyl ester;
{2-Methyl-4-[(5-phenyl-thiophen-2-ylmethyl)-amino]-phenyl}-carbamic acid propyl ester;
[4-(4-Isopropyl-benzylamino)-2-methylphenyl]-carbamic acid propyl ester;
{4-[(5-Bromo-thiophen-2-ylmethyl)-amino]-2-chlorophenyl}-carbamic acid ethyl ester;
{4-[(5-Chloro-thiophen-2-ylmethyl)-amino]-2-chlorophenyl}-carbamic acid ethyl ester;
{4-[(Benzo[b]thiophen-2-ylmethyl)-amino]-2-chlorophenyl}-carbamic acid ethyl ester;
[2-Chloro-4-(4-isopropyl-benzylamino)-phenyl]-carbamic acid ethyl ester;
[2-Chloro-4-(4-fluoro-benzylamino)-phenyl]-carbamic acid propyl ester;
2-Chloro-4-{[4-(4-chloro-benzenesulfonyl)-3-methyl-thiophen-2-ylmethyl]-amino}-phenyl)-carbamic acid propyl ester;
{4[(5-Methyl-thiophen-2-ylmethyl)-amino]-2-chlorophenyl}-carbamic acid propyl ester;
{4[(5-Bromo-thiophen-2-ylmethyl)-amino]-2-chlorophenyl}-carbamic acid propyl ester;
{2-Chloro-4-[(5-chloro-thiophen-2-ylmethyl)-amino]-phenyl}-carbamic acid propyl ester;
{4-[(Benzo[b]thiophen-2-ylmethyl)-amino]-2-chlorophenyl}-carbamic acid propyl ester;
{4-[(Benzofuran-2-ylmethyl)-amino]-2-chlorophenyl}-carbamic acid propyl ester;
{4-[(5-Chloro-thiophen-2-ylmethyl)-amino]-2-cyanophenyl}-carbamic acid ethyl ester;
{4-[(Benzo[b]thiophen-2-ylmethyl)-amino]-2-methoxyphenyl}-carbamic acid methyl ester;
{4-[(5-Bromo-thiophen-2-ylmethyl)-amino]-2-methoxyphenyl}-carbamic acid isopropyl ester;
{4-[(4-Fluoro-benzyl)-(methyl)amino]-2-methoxyphenyl}-carbamic acid propyl ester;
[4-(Benzo[b]thiophen-2-ylmethyl-(methyl)amino)-2-methoxy-phenyl]-carbamic acid propyl ester;
{4-[(5-Chloro-thiophen-2-ylmethyl)-(methyl)amino]-2-methoxy-phenyl}-carbamic acid propyl ester;
{4-[(5-Bromo-thiophen-2-ylmethyl)-(methyl)amino]-2-methoxy-phenyl}-carbamic acid propyl ester;
{2-Methoxy-4-[methyl-(5-methyl-thiophen-2-ylmethyl)-amino]-phenyl}-carbamic acid propyl ester;
{4-[(4-Fluorobenzyl)-(methyl)-amino]-2-isopropoxyphenyl}-carbamic acid ethyl ester;
[4-(3-Fluorobenzylamino)-2-methoxyphenyl]-carbamic acid ethyl ester;
[4-(4-Isopropylbenzylamino)-2-methoxyphenyl]-carbamic acid ethyl ester;
{2-Methoxy-4-[(3-methylthiophen-2-ylmethyl)-amino]-phenyl}-carbamic acid ethyl ester;
[4-(2,4-Difluorobenzylamino)-2-methoxyphenyl]-carbamic acid ethyl ester;
[2-Cyclopentyloxy-4-(4-methoxybenzylamino)-phenyl]-carbamic acid ethyl ester;
[2-Cyclopentyloxy-4-(3-fluoro-2-methylbenzylamino)-phenyl]-carbamic acid ethyl ester;
[4-(3-Fluoro-2-methylbenzylamino)-2-phenethyloxyphenyl]-carbamic acid ethyl ester;
[2-Benzyloxy-4-(3-fluoro-2-methylbenzylamino)-phenyl]-carbamic acid ethyl ester;
[2-Benzyloxy-4-(4-methylsulfanylbenzylamino)-phenyl]-carbamic acid ethyl ester;
{4-[(Benzo[b]thiophen-3-ylmethyl)-amino]-2-cyclopentyloxyphenyl}-carbamic acid ethyl ester;
[4-(3-Fluoro-2-methylbenzylamino)-2-isopropoxyphenyl]-carbamic acid ethyl ester;
[2-Benzyloxy-4-(3-methoxybenzylamino)-phenyl]-carbamic acid ethyl ester;
{4-[(Benzo[1,3]dioxol-5-ylmethyl)-amino]-2-isopropoxyphenyl}-carbamic acid ethyl ester;
{4-[(5-Bromo-thiophen-2-ylmethyl)-amino]-phenyl}-carbamic acid propyl ester;
{4-[(5-Chloro-thiophen-2-ylmethyl)-amino]-phenyl}-carbamic acid propyl ester;
[2-Cyano-4-(4-isopropylbenzylamino)-phenyl]-carbamic acid ethyl ester;
{4-[(5-Bromo-thiophen-2-ylmethyl)-(methyl)amino]-2-methylphenyl}-carbamic acid propyl ester;
{4-[(4-Isopropylbenzyl)-(methyl)amino]-2-methylphenyl}-carbamic acid propyl ester;
{2-Methyl-4-[methyl-(4-trifluorophenyl-benzyl)-amino]-phenyl}-carbamic acid propyl ester;
{2-Methyl-4-[methyl-(4-methylsulfanyl-benzyl)-amino]-phenyl}-carbamic acid propyl ester;

{4-[(4-tert-Butyl-benzyl)-(methyl)amino]-2-chlorophenyl}-carbamic acid ethyl ester;
{2-Chloro-4[c ethyl-(4-trifluoromethyl-benzyl)-amino]-phenyl}-carbamic acid ethyl ester;
{2-Chloro-4[methyl-(4-methylsulfanyl-benzyl)-amino]-phenyl}-carbamic acid ethyl ester:
{4-[(5-Bromo-thiophen-2-ylmethyl)-(methyl)amino]-2-chlorophenyl}-carbamic acid propyl ester;
{2-Chloro-4-[(5-chloro-thiophen-2-ylmethyl)-(methyl)amino]-phenyl}-carbamic acid propyl ester;
{4-[(4-tert-Butyl-benzyl)-(methyl)amino]-2-chlorophenyl}-carbamic acid propyl ester;
{2-Chloro-4-[methyl-(4-trifluoromethyl-benzyl)-amino]-phenyl}-carbamic acid propyl ester;
{4-[(5-Bromo-thiophen-2-ylmethyl)-(methyl)amino]-2-trifluoromethyl-phenyl}-carbamic acid ethyl ester;
{4-[(5-Chloro-thiophen-2-ylmethyl)-(methyl)amino]-2-trifluoromethyl-phenyl}-carbamic acid ethyl ester;
{4-[(4-Isopropyl-benzyl)-(methyl)amino]-2-trifluoromethyl-phenyl}-carbamic acid ethyl ester;
{4-[(4-tert-Butyl-benzyl)-(methyl)amino]-2-trifluoromethyl-phenyl}-carbamic acid ethyl ester;
{4-[Methyl-(4-trifluoromethyl-benzyl)-amino]-2-trifluoromethyl-phenyl}-carbamic acid ethyl ester;
{4-[Methyl-(4-methylsulfanyl-benzyl)-amino]-2-trifluoromethyl-phenyl}-carbamic acid ethyl ester;
{4-[(5-Bromo-thiophen-2-ylmethyl)-(methyl)amino]-2-trifluoromethyl-phenyl}-carbamic acid propyl ester;
{4-[(5-Chloro-thiophen-2-ylmethyl)-(methyl)amino]-2-trifluoromethyl-phenyl}-carbamic acid propyl ester;
{4-[(4-Isopropyl-benzyl)-(methyl)amino]-2-trifluoromethyl-phenyl}-carbamic acid propyl ester;
{4-[(4-tert-Butyl-benzyl)-(methyl)amino]-2-trifluoromethyl-phenyl}carbamic acid propyl ester;
{4-[Methyl-(4-trifluoromethyl-benzyl)-amino]-2-trifluoromethyl-phenyl}-carbamic acid propyl ester;
{4-[Methyl-(4-methylsulfanyl-benzyl)-amino]-2-trifluoromethyl-phenyl}-carbamic acid propyl ester;
{4-[(5-Bromo-thiophen-2-ylmethyl)-(methyl)amino]-2-cyanophenyl}-carbamic acid propyl ester;
{4-[(4-tert-Butyl-benzyl)-(methyl)amino]-2-cyanophenyl}-carbamic acid propyl ester;
{2-Cyano-4-[methyl-(4-trifluoromethyl-benzyl)-amino]-phenyl}-carbamic acid propyl ester;
{2-Bromo-4-[(5-bromo-thiophen-2-ylmethyl)-(methyl)amino]-phenyl}-carbamic acid propyl ester;
{2-Bromo-4-[(5-chloro-thiophen-2-ylmethyl)-(methyl)amino]-phenyl}-carbamic acid propyl ester;
{2-Bromo-4-[(4-isopropylbenzyl)-(methyl)amino]-phenyl}-carbamic acid propyl ester;
{2-Bromo-4-[(4-tert-butyl-benzyl)-(methyl)amino]-phenyl}-carbamic acid propyl ester;
{2-Bromo-4-[methyl-(4-trifluoromethyl-benzyl)-amino]-phenyl}-carbamic acid propyl ester;
[2-Iodo-4-(4-isopropyl-benzylamino)-phenyl]-carbamic acid propyl ester;
[4-(4-tert-Butyl-benzylamino)-2-iodophenyl]-carbamic acid propyl ester;
[2-Iodo-4-(4-trifluoromethyl-benzylamino)-phenyl]-carbamic acid propyl ester;
[2-Iodo-4-(4-methylsulfanyl-benzylamino)-phenyl]-carbamic acid propyl ester;
{2-Iodo-4-[4-(4-methylpiperazin-1-yl)-benzylamino]-phenyl}-carbamic acid propyl ester;
{4-[(5-Bromo-thiophen-2-ylmethyl)-amino]-2-trifluoromethyl-phenyl}-carbamic acid ethyl ester;
{4-[(5-Chloro-thiophen-2-ylmethyl)-amino]-2-trifluoromethyl-phenyl}-carbamic acid ethyl ester;
[4-(4-tert-Butyl-benzylamino)-2-trifluoromethyl-phenyl]-carbamic acid ethyl ester;
[4-(4-Methylsulfanyl-benzylamino)-2-trifluoromethyl-phenyl]-carbamic acid ethyl ester;
{4-[(5-Bromo-thiophen-2-ylmethyl)-amino]-2-trifluoromethyl-phenyl}-carbamic acid propyl ester;
[4-(4-Isopropylbenzylamino)-2-trifluoromethyl-phenyl]-carbamic acid propyl ester;
[4-(4-tert-Butyl-benzylamino)-2-trifluoromethyl-phenyl]-carbamic acid propyl ester;
[2-Trifluoromethyl-4-(4-trifluoromethyl-benzylamino)-phenyl]-carbamic acid propyl ester;
[4-(4-Dimethylamino-benzylamino)-2-trifluoromethyl-phenyl]-carbamic acid propyl ester;
[4-(4-Methylsulfanyl-benzylamino)-2-trifluoromethyl-phenyl]-carbamic acid propyl ester;
{4-[(5-Bromo-thiophen-2-ylmethyl)-amino]-2-cyanophenyl}-carbamic acid propyl ester;
{4-[(5-Chloro-thiophen-2-ylmethyl)-amino]-2-cyanophenyl}-carbamic acid propyl ester;
[2-Cyano-4-(4-trifluoromethyl-benzylamino)-phenyl]-carbamic acid propyl ester;
{2-Bromo-4-[(5-bromo-thiophen-2-ylmethyl)-amino]-phenyl}-carbamic acid propyl ester;
{2-Bromo-4-[(5-chloro-thiophen-2-ylmethyl)-amino]-phenyl}-carbamic acid propyl ester;
[2-Bromo-4-(4-isopropylbenzylamino)-phenyl]-carbamic acid propyl ester;
[2-Bromo-4-(4-tert-butyl-benzylamino)-phenyl]-carbamic acid propyl ester;
[2-Bromo-4-(4-trifluoromethyl-benzylamino)-phenyl]-carbamic acid propyl ester;
[2-Bromo-4-(4-methylsulfanyl-benzylamino)-phenyl]-carbamic acid propyl ester;
N-{4-[(5-Bromo-thiophen-2-ylmethyl)-amino]-2-methoxyphenyl}-butyramide;
N-{4-[(5-Chloro-thiophen-2-ylmethyl)-amino]-2-methoxyphenyl}-butyramide;
N-[4-(4-Isopropylbenzylamino)-2-methoxyphenyl]-butyramide;
N-[4-(4-tert-Butyl-benzylamino)-2-methoxyphenyl]-butyramide;
N-[2-Methoxy-4-(4-trifluoromethyl-benzylamino)-phenyl]-butyramide;
{4-[(5-Chloro-thiophen-2-ylmethyl)-amino]-2-furan-2-yl-phenyl}-carbamic acid propyl ester;
[2-Furan-2-yl-4-(4-isopropylbenzylamino)-phenyl]-carbamic acid propyl ester;
[5-(4-Fluorobenzylamino)-biphenyl-2-yl]-carbamic acid propyl ester;
{5-[(5-Chloro-thiophen-2-ylmethyl)-amino]-biphenyl-2-yl}-carbamic acid propyl ester;
[5-(4-Isopropylbenzylamino)-biphenyl-2-yl]-carbamic acid propyl ester;
N-{2-Chloro-4-[(5-chloro-thiophen-2-ylmethyl)-(methyl)amino]-phenyl}-2-phenylacetamide;
N-{2-Chloro-4-[(5-chloro-thiophen-2-yl-ethyl)-(methyl)amino]-phenyl}-3,3-dimethylbutyramide;
N-{2-Chloro-4-[(5-chloro-thiophen-2-ylmethyl-(methyl)amino]-phenyl}-3-phenylpropionamide;
N-{2-Chloro-4-[(5-chloro-thiophen-2-ylmethyl)-(methyl)amino]-phenyl}-butyramide;
Pentanoic acid {2-chloro-4-[(5-chloro-thiophen-2-ylmethyl)-(methyl)amino]-phenyl}-amide;

Cyclopropanecarboxylic acid {2-chloro-4-[(5-chloro-thiophen-2-ylmethyl)-(methyl)amino]-phenyl}-amide;
Cyclobutanecarboxylic acid {2-chloro-4-[(5-chloro-thiophen-2-ylmethyl)-(methyl)amino]-phenyl}-amide;
Cyclopentanecarboxylic acid {2-chloro-4-[(5-chloro-thiophen-2-ylmethyl)-(methyl)amino]-phenyl}-amide;
Cyclohexanecarboxylic acid {2-chloro-4-[(5-chloro-thiophen-2-ylmethyl)-(methyl)amino]-phenyl}-amide;
N-{2-Chloro-4-[(5-chloro-thiophen-2-ylmethyl)-(methyl)amino]-phenyl}-2-thiophen-2-yl-acetamide;
N-{2-Chloro-4-[(5-chloro-thiophen-2-yl ethyl)-(ethyl)amino]-phenyl}-2-(3-methoxy-phenyl)-acetamide;
N-{2-Chloro-4-[(5-chloro-thiophen-2-ylmethyl)-(methyl)amino]-phenyl}-2-(4-chloro-phenyl)-acetamide;
N-{2-Chloro-4-[(5-chloro-thiophen-2-ylmethyl)-(methyl)amino]-phenyl}-2-(4-methoxy-phenyl)-acetamide;
N-{2-Chloro-4-[(5-chloro-thiophen-2-ylmethyl)-(methyl)amino]-phenyl}-2-(4-fluoro-phenyl)-acetamide;
N-{2-Chloro-4-[(5-chloro-thiophen-2-ylmethyl)-(methyl)amino]-phenyl}-3-cyclohexylpropionamide;
N-{2-Chloro-4-[(5-chloro-thiophen-2-ylmethyl)-amino]-phenyl}-2,2-dimethylpropionamide;
N-{2-Chloro-4-[(5-chloro-thiophen-2-ylmethyl)-amino]-phenyl}-2-phenoxyacetamide;
N-{2-Chloro-4-[(5-chloro-thiophen-2-ylmethyl)-amino]-phenyl}-2-phenylacetamide;
N-{2-Chloro-4-[(5-chloro-thiophen-2-ylmethyl)-amino]-phenyl}-3,3-dimethylbutyramide;
N-{2-Chloro-4-[(5-chloro-thiophen-2-ylmethyl)-amino]-phenyl}-butyramide;
Pentanoic acid {2-chloro-4-[(5-chloro-thiophen-2-ylmethyl)-amino]-phenyl}-amide;
Cyclopropanecarboxylic acid {2-chloro-4-[(5-chloro-thiophen-2-ylmethyl)-amino]-phenyl}-amide;
Cyclobutanecarboxylic acid {2-chloro-4-[(5-chloro-thiophen-2-ylmethyl)-amino]-phenyl}-amide;
Cyclopentanecarboxylic acid {2-chloro-4-[(5-chloro-thiophen-2-ylmethyl)-amino]-phenyl}-amide;
Cyclohexanecarboxylic acid {2-chloro-4-[(5-chloro-thiophen-2-ylmethyl)-amino]-phenyl}-amide;
N-{2-Chloro-4-[(5-chloro-thiophen-2-ylmethyl)-amino]-phenyl}-2-thiophen-2-yl-acetamide;
N-{2-Chloro-4-[(5-chloro-thiophen-2-ylmethyl)-amino]-phenyl}-2-(3-methoxyphenyl)-acetamide;
N-{2-Chloro-4-[(5-chloro-thiophen-2-ylmethyl)-amino]-phenyl}-2-(4-chlorophenyl)-acetamide;
N-{2-Chloro-4-[(5-chloro-thiophen-2-ylmethyl)-amino]-phenyl}-2-(4-methoxyphenyl)-acetamide;
N-{2-Chloro-4-[(5-chloro-thiophen-2-ylmethyl)-amino]-phenyl}-2-(4-fluorophenyl)-acetamide;
2,3-Dihydro-benzo[1,4]dioxine-6-carboxylic acid {2-chloro-4-[(5-chloro-thiophen-2-ylmethyl)-amino]-phenyl}-amide;
2,3-Dihydro-benzofuran-5-carboxylic acid {2-chloro-4-[(5-chloro-thiophen-2-ylmethyl)-amino]-phenyl}-amide;
N-{2-Chloro-4-[(5-chloro-thiophen-2-ylmethyl)-amino]-phenyl}-3-cyclohexylpropionamide;
N-{4-[(5-Chloro-thiophen-2-ylmethyl)-(methyl)amino]-2-methyl-phenyl}-2,2-dimethylpropionamide;
N-{4-[(5-Chloro-thiophen-2-ylmethyl)-(methyl)amino]-2-methyl-phenyl}-2-phenylacetamide;
N-{4-[(5-Chloro-thiophen-2-ylmethyl)-(methyl)amino]-2-methyl-phenyl}-3,3-dimethylbutyramide;
N-{4-[(5-Chloro-thiophen-2-ylmethyl)-(methyl)amino]-2-methyl-phenyl}-3-phenylpropionamide;
N-{4-[(5-Chloro-thiophen-2-ylmethyl)-(methyl)amino]-2-methyl-phenyl}-butyramide;
2,2,2-Trichloro-N-{4-[(5-chloro-thiophen-2-ylmethyl)-(ethyl)amino]-2-methyl-phenyl}-acetamide;
Cyclopropanecarboxylic acid {4-[(5-chloro-thiophen-2-yl-methyl)-(methyl)amino]-2-methyl-phenyl}-amide;
Cyclobutanecarboxylic acid {4-[(5-chloro-thiophen-2-ylmethyl)-(methyl)amino]-2-methylphenyl}-amide;
Cyclopentanecarboxylic acid {4-[(5-chloro-thiophen-2-ylmethyl)-(methyl)amino]-2-methylphenyl}-amide;
Cyclohexanecarboxylic acid {4-[(5-chloro-thiophen-2-ylmethyl)-(methyl)amino]-2-methylphenyl}-amide;
N-{4-[(5-Chloro-thiophen-2-ylmethyl)-(methyl)amino]-2-methylphenyl}-2-thiophen-2-yl-acetamide;
N-{4-[(5-Chloro-thiophen-2-ylmethyl)-(methyl)amino]-2-methylphenyl}-2-(3-methoxyphenyl)-acetamide;
N-{4-[(5-Chloro-thiophen-2-ylmethyl)-(methyl)amino]-2-methylphenyl}-malonamic acid methyl ester;
2-(4-Chlorophenyl)-N-{4-[(5-chloro-thiophen-2-ylmethyl)-(ethyl)amino]-2-methylphenyl}-acetamide;
N-{4-[(5-Chloro-thiophen-2-ylmethyl)-(methyl)amino]-2-methylphenyl}-2-(4-methoxyphenyl)-acetamide;
N-{4-[(5-Chloro-thiophen-2-ylmethyl)-(methyl)amino]-2-methylphenyl}-2-(4-fluorophenyl)-acetamide;
N-{4-[(5-Chloro-thiophen-2-ylmethyl)-(methyl)amino]-2-methylphenyl}-3-cyclohexylpropionamide;
{2-Chloro-4-[(5-chloro-thiophen-2-ylmethyl)-(methyl)amino]-phenyl}-carbamic acid phenyl ester;
{2-Chloro-4-[(5-chloro-thiophen-2-ylmethyl)-(methyl)amino]-phenyl}-carbamic acid benzyl ester;
{2-Chloro-4-[(5-chloro-thiophen-2-ylmethyl)-(methyl)amino]-phenyl}-carbamic acid isobutyl ester;
{2-Chloro-4[(5-chloro-thiophen-2-ylmethyl)-(methyl)amino]-phenyl}-carbamic acid butyl ester;
{2-Chloro-4-[(5-chloro-thiophen-2-ylmethyl)-(methyl)amino]-phenyl}-carbamic acid hexyl ester;
{2-Chloro-4-[(5-chloro-thiophen-2-ylmethyl)-ylmethyl)-(methyl)amino]-phenyl}carbamic acid 4-nitrobenzyl ester;
{2-Chloro-4-[(5-chloro-thiophen-2-ylmethyl)-(methyl)amino]-phenyl}-carbamic acid but-3-enyl ester;
{2-Chloro-4-[(5-chloro-thiophen-2-ylmethyl)-(methyl)amino]-phenyl}-carbamic acid but-2-ynyl ester;
{2-Chloro-4-[(5-chloro-thiophen-2-ylmethyl)-(methyl)amino]-phenyl}-carbamic acid 2,2-dimethylpropyl ester;
{2-Chloro-4-[(5-chloro-thiophen-2-ylmethyl)-(methyl)amino]-phenyl}-carbamic acid 2-chlorobenzyl ester;
{2-Chloro-4-[(5-chloro-thiophen-2-ylmethyl)-(methyl)amino]-phenyl}-carbamic acid 3-chloropropyl ester;
{2-Chloro-4-[(5-chloro-thiophen-2-ylmethyl)-(methyl)amino]-phenyl}-carbamic acid 2-benzyloxyethyl ester;
3-{2-Chloro-4-[(5-chloro-thiophen-2-ylmethyl)-(methyl)amino]-phenyl}-1-methyl-1-propyl-urea;
1-{2-Chloro-4-[(5-chloro-thiophen-2-ylmethyl)-(methyl)amino]-phenyl}-3-(2-fluorophenyl)-urea;
N-{2-Chloro-4-[(5-chloro-thiophen-2-ylmethyl)-(methyl)amino]-phenyl}-2,2,2-trifluoroacetamide;
N-{2-Chloro-4-[(5-chloro-thiophen-2-ylmethyl)-amino]-phenyl}-2,2,2-trifluoroacetamide;
N-{5-[(5-Chloro-thiophen-2-ylmethyl)-amino]-4'-dimethylamino-biphenyl-2-yl}-2-(4-fluorophenyl)-acetamide;
N-{2-Chloro-4-[(5-chloro-thiophen-2-ylmethyl)-(methyl)amino]-phenyl}-2-(4-chlorophenyl)-acetamide;
[4-(3-Fluoro-4-trifluoromethyl-benzylamino)-2-methylphenyl]-carbamic acid ethyl ester;
2-(4-Fluorophenyl)-N-{2-methyl-4-[(6-p-tolyloxypyridin-3-ylmethyl); amino]-phenyl}-acetamide;
N-[2-Methyl-4-(4-trifluoromethyl-benzylamino)-phenyl]-butyramide;

2-(4-Fluorophenyl)-N-{2-methyl-4[(6-trifluoromethylpyridin-3-ylmethyl)-amino]-phenyl}-acetamide;
Pentanoic acid {4-[(5-chloro-thiophen-2-ylmethyl)-(methyl)amino]-2-methylphenyl}-amide;
3,3-Dimethyl-N-{2-methyl-4-[(6-p-tolyloxypyridin-3-ylmethyl)-amino]-phenyl}-butyramide;
[2-Methyl-4-(4-trifluoromethyl-benzylamino)-phenyl]-carbamic acid ethyl ester;
N-{2-Chloro-4-[(5-chloro-thiophen-2-ylmethyl)-(methyl)amino]-phenyl}-2-(4-chlorophenyl)-propionamide;
[4-(4-Chloro-benzylamino)-2-methylphenyl]-carbamic acid ethyl ester;
{4[(6-Methoxy-benzo[b]thiophen-2-ylmethyl)-amino]-2-methylphenyl}-carbamic acid propyl ester;
{4-[(5-Chloro-thiophen-2-ylmethyl)-amino]-2-quinolin-3-yl-phenyl}-carbamic acid ethyl ester;
{4-[5-Dimethylamino-3-methyl-benzo[b]thiophen-2-ylmethyl)-amino]-2-methylphenyl}-carbamic acid propyl ester;
3,3-Dimethyl-N-{2-methyl-4-[(6-trifluoromethylpyridin-3-ylmethyl)-amino]-phenyl}-butyramide;
N-(4-{[6-(4-Cyanophenoxy)-pyridin-3-ylmethyl]-amino}-2-methylphenyl)-2-(4-fluorophenyl)-acetamide;
{2-Benzyloxy-4-[(4-fluorobenzyl)-(ylmethyl)amino]-phenyl}-thiocarbamic acid S-ethyl ester;
{2-Cyclopentyloxy-4[(4-fluorobenzyl)-(methyl)amino]-phenyl}-thiocarbamic acid S-ethyl ester;
N-{4-[(6-Chloropyridin-3-ylmethyl)-amino]-2-methylphenyl}-2-(4-fluorophenyl)-acetamide;
{4-[(7-Dimethylamino-benzo[b]thiophen-2-ylmethyl)-amino]-2-methylphenyl}-carbamic acid propyl ester;
1-{2-Cyclopentyloxy-4-[(4-fluorobenzyl)-(ylmethyl)amino]-phenyl}-3-ethyl-urea;
2-Amino-4-methyl-pentanoic acid [2-methyl-4-(4-trifluoromethyl-benzylamino)-phenyl]-amide;
{4-[(6-Methoxy-benzo[b]thiophen-2-ylmethyl)-amino]-2-methylphenyl}-carbamic acid ethyl ester;
2-Amino-4-methyl-pentanoic acid [2-methyl-4-(4-trifluoromethyl-benzylamino)-phenyl]-amide;
2-(4-Fluorophenyl)-N-{2-methyl-4-[(4-methyl-2-phenylpyridin-5-ylmethyl)-amino]-phenyl}-acetamide;
3,3-Dimethyl-N-{2-methyl-4-[(2-phenylpyrimidin-5-ylmethyl-amino]-phenyl}-butyramide;
{4-[(5-Chloro-thiophen-2-ylmethyl)-amino]-2-pyridin-3-yl-phenyl}-carbamic acid ethyl ester;
1-Amino-cyclopropanecarboxylic acid [2-methyl-4-(4-trifluoromethyl-benzylamino)-phenyl]-amide;
{4-[(5-Chloro-thiophen-2-ylmethyl)-amino]-2-pyridin-4-yl-phenyl}-carbamic acid ethyl ester;
N-[2-Methyl-4-(4-trifluoromethyl-benzylamino)-phenyl]-2-piperidin-1-yl-acetamide;
N-(4-{[5-(4-Chlorophenoxy)-1,3-dimethyl-1H-pyrazol-4-ylmethyl]-amino}-2-methylphenyl)-2,2-dimethylpropionamide;
2,2-Dimethyl-N-{2-methyl-4-[(6-phenoxypyridin-3-ylmethyl)-amino]-phenyl}-propionamide;
N-[2-Methyl-4-(4-trifluoromethyl-benzylamino)-phenyl]-2-pyrrolidin-1-yl-acetamide;
[4-[(5-Chloro-thiophen-2-ylmethyl)-amino]-2-(6-methoxy-pyridin-3-yl)-phenyl]-carbamic acid ethyl ester;
4-[(3-Methyl-4-propoxycarbonylamino-phenylamino)-methyl]-benzoic acid methyl ester;
N-[2-Methyl-4-(4-trifluoromethyl-benzylamino)-phenyl]-2-morpholin-4-yl-acetamide;
2,2-Dimethyl-N-{2-methyl-4-[(3-methyl-5-phenylisoxazol-4-ylmethyl)-amino]-phenyl}-propionamide;
{4-[(5-Chloro-thiophen-2-ylmethyl)-amino]-2-iodophenyl}-carbamic acid ethyl ester;
N-{4-[(5-Chloro-thiophen-2-ylmethyl)-amino]-2-iodophenyl}-2-(4-fluorophenyl)-acetamide; and
{4[(5-Chloro-thiophen-2-ylmethyl)-amino]-2-quinolin-5-yl-phenyl}-carbamic acid ethyl ester.

According to one embodiment, the invention relates to a pharmaceutical composition comprising one or more pharmaceutically acceptable carriers or diluents and a compound of formula I wherein s, q, U, X, Z, Y, $R^1$, $R^2$ and $R^3$ are as defined above, accordingly any of a, b, c, d, e, f, g, h, s, q, U, X, Z, Y W, $R^1$, $R^2$, $R^3$, $R^5$, $R^6$, $R^{6'}$, $R^7$, $R^{7'}$, $R^8$, $R^9$, $R^{9'}$, $R^{10}$, $R^{10'}$, $R^{11}$, $R^{12}$ and $R^{12'}$ are as defined under formula I, or salts thereof. Pharmaceutical compositions of the invention may thus comprise one or more compounds of formula I or salts thereof, such as one compound of formula I or a salt thereof; or two compounds of formula I or salts thereof; or three compounds of formula I or salts thereof.

According to one embodiment, the invention relates to a pharmaceutical composition comprising one or more pharmaceutically acceptable carriers or diluents and a compound of formula XXIX wherein f, s, q, U, X, Z, $R^1$, $R^2$, $R^3$ and $R^5$ are as defined above, accordingly any of f, s, q, U, X, Z, $R^1$, $R^2$, $R^3$, $R^5$, $R^6$, $R^{6'}$, $R^7$, $R^{7'}$, $R^8$, $R^9$, $R^{9'}$, $R^{10}$, $R^{10'}$, $R^{11}$, $R^{12}$ and $R^{12'}$ are as defined under formula XXIX. Pharmaceutical compositions of the invention may thus comprise one or more compounds of formula XXIX or salts thereof, such as one compound of formula XXIX or a salt thereof; or two compounds of formula XXIX or salts thereof; or three compounds of formula XXIX or salts thereof.

According to one embodiment, the invention relates to a pharmaceutical composition comprising one or more pharmaceutically acceptable carriers or diluents and a compound of formula XXX wherein g, h, s, q, U, X, Z, $R^1$, $R^2$, $R^3$ and $R^5$ are as defined above, accordingly any of g, h, s, q, U, X, Z, $R^1$, $R^2$, $R^3$, $R^5$, $R^6$, $R^{6'}$, $R^7$, $R^{7'}$, $R^8$, $R^9$, $R^{9'}$, $R^{10}$, $R^{10'}$, $R^{11}$, $R^{12}$ and $R^{12'}$ are as defined under formula XXX. Pharmaceutical compositions of the invention may thus comprise one or more compounds of formula XXX or salts thereof, such as one compound of formula XXX or a salt thereof; or two compounds of formula XXX or salts thereof; or three compounds of formula XXX or salts thereof.

According to one embodiment, the invention relates to a pharmaceutical composition comprising one or more pharmaceutically acceptable carriers or diluents and a compound of formula XXXI wherein a, s, q, U, W, X, Z, $R^1$, $R^2$, $R^3$ and $R^5$ are as defined above, accordingly any of a, s, q, U, W, X, Z, $R^1$, $R^2$, $R^3$, $R^5$, $R^6$, $R^{6'}$, $R^7$, $R^{7'}$, $R^8$, $R^9$, $R^{9'}$, $R^{10}$, $R^{10'}$, $R^{11}$, $R^{12}$ and $R^{12'}$ are as defined under formula XI. Pharmaceutical compositions of the invention may thus comprise one or more compounds of formula XXXI or salts thereof, such as one compound of formula XXXI or a salt thereof; or two compounds of formula XXXI or salts thereof; or three compounds of formula XXXI or salts thereof.

According to one embodiment, the invention relates to a pharmaceutical composition comprising one or more pharmaceutically acceptable carriers or diluents and a compound of formula XXXII wherein b, c, s, q, U, W, X, Z, $R^1$, $R^2$, $R^3$ and $R^5$ are as defined above, accordingly any of b, c, s, q, U, W, X, Z, $R^1$, $R^2$, $R^3$, $R^5$, $R^6$, $R^{6'}$, $R^7$, $R^{7'}$, $R^8$, $R^9$, $R^{9'}$, $R^{10}$, $R^{10'}$, $R^{11}$, $R^{12}$ and $R^{12'}$ areas defined under formula XXXII. Pharmaceutical compositions of the invention may thus comprise one or more compounds of formula XXXII or salts thereof, such as one compound of formula XXXII or a salt thereof; or two compounds of formula XXXII or salts thereof; or three compounds of formula XXXII or salts thereof.

According to one embodiment, the invention relates to a pharmaceutical composition comprising one or more pharmaceutically acceptable carriers or diluents and a compound of formula XXXIII wherein d, e, s, q, U, W, X, Z, $R^1$, $R^2$, $R^3$ and $R^5$ are as defined above, accordingly any of d, e, s, q, U, W, X, Z, $R^1$, $R^2$, $R^3$, $R^5$, $R^6$, $R^{6'}$, $R^7$, $R^{7'}$, $R^8$, $R^9$, $R^{9'}$, $R^{10}$, $R^{10'}$, $R^{11}$, $R^{12}$ and $R^{12'}$ are as defined under formula XXXIII. Pharmaceutical compositions of the invention may thus comprise one or more compounds of formula XXXIII or salts thereof, such as one compound of formula XXXIII or a salt thereof; or two compounds of formula XXXIII or salts thereof; or three compounds of formula XXXIII or salts thereof.

The invention thus provides a pharmaceutical composition for oral or parenteral administration, said pharmaceutical composition comprising at least one compound of formula I or XXIX or XXX or XXXI or XXXII or XXXIII or a salt thereof in a therapeutically effective amount together with one or more pharmaceutically acceptable carriers or diluents.

In one aspect, the compounds of the invention may be administered as the only therapeutically effective compound.

In another aspect the compounds of the invention may be administered as a part of a combination therapy, i.e. the compounds of the invention may be administered in combination with other therapeutically effective compounds having e.g. anti-convulsive properties. The effects of such other compounds having anti-convulsive properties may include but not be limited to activities on:
  ion channels such as sodium, potassium, or calcium channels
  the excitatory amino acid systems e.g. blockade or modulation of NMDA receptors
  the inhibitory neurotransmitter systems e.g. enhancement of GABA release, or blockade of GABA-uptake or
  membrane stabilisation effects.

Current anti-convulsive medications include, but are not limited to, tiagabine, carbamazepine, sodium valproate, lamotrigine, gabapentin, pregabalin, ethosuximide, levetiracetam, phenytoin, topiramate, zonisamide as well as members of the benzodiazepine and barbiturate class.

In one aspect, the compounds of the invention have been found to have effect on potassium channels of the KCNQ family, in particular the KCNQ2 subunit.

In one embodiment, the invention relates to the use of one or more compounds according to the invention in a method of treatment. The disorder or condition to be prevented, treated or inhibited is responsive to an increased ion flow in a potassium channel such as the KCNQ family potassium ion channels. Such disorder or condition is preferably a disorder or condition of the central nervous system.

The compounds of the invention are considered useful for increasing ion flow in a voltage-dependent potassium channel in a mammal such as a human.

The compounds of the invention are considered useful for the prevention, treatment or inhibition of a disorder or condition being responsive to an increased ion flow in a potassium channel such as the KCNQ family potassium ion channels. Such disorder or condition is preferably a disorder or condition of the central nervous system.

The compounds of the invention are thus considered useful for preventing, treating or inhibiting disorders or diseases such as seizure disorders, neuropathic and migraine pain disorders, anxiety disorders and neurodegenerative disorders.

Accordingly, the compounds of the invention are considered useful for the prevention, treatment or inhibition of disorders or conditions such as convulsions, epilepsy, anxiety disorders, neuropathic pain and neurodegenerative disorders.

According to one particular embodiment, the compounds of the invention are thus considered to be useful for preventing, treating or inhibiting seizure disorders such as convulsions, epilepsy and status epilepticus.

In one embodiment, the compounds of the invention are considered useful in the prevention, treatment and inhibition of convulsions.

In another embodiment, the compounds of the invention are considered useful in the prevention, treatment and inhibition of epilepsy, epileptic syndromes and epileptic seizures.

In yet another embodiment, the compounds of the invention are considered useful in the prevention, treatment and inhibition of anxiety disorders such as anxiety and conditions and diseases related to panic attack, agoraphobia, panic disorder with agoraphobia, panic disorder without agoraphobia, agoraphobia without history of panic disorder, specific phobia, social phobia and other specific phobias, obsessive-compulsive disorder, posttraumatic stress disorder, acute stress disorders, generalized anxiety disorder, anxiety disorder due to general medical condition, substance-induced anxiety disorder, separation anxiety disorder, adjustment disorders, performance anxiety, hypochondriacal disorders, anxiety disorder due to general medical condition and substance-induced anxiety disorder and anxiety disorder not otherwise specified.

In yet another embodiment, the compounds of the invention are considered useful in the prevention, treatment and inhibition of neuropathic pain and migraine pain disorders such as allodynia, hyperalgesic pain, phantom pain, neuropathic pain related to diabetic neuropathy and neupathic pain related to migraine.

In yet another embodiment, t the compounds of the invention are considered useful in the prevention, treatment and inhibition of neurodegenerative disorders such as Alzheimer's disease; Huntington's chorea; multiple sclerosis; amyotrophic lateral sclerosis; Creutzfeld-Jakob disease; Parkinson's disease; encephalopathies induced by AIDS or infection by rubella viruses, herpes viruses, borrelia and unknown pathogens; trauma-induced neurodegenerations; neuronal hyperexcitation states such as in medicament withdrawal or intoxication; and neurodegenerative diseases of the peripheral nervous system such as polyneuropathies and polyneuritides.

In yet another embodiment, the compounds of the invention are considered useful in the prevention, treatment and inhibition of neurodegenerative disorders such as Alzheimer's disease; Huntington's chorea; multiple sclerosis; amyotrophic lateral sclerosis; Creutzfeld-Jakob disease; Parkinson's disease; encephalopathies induced by AIDS or infection by rubella viruses, herpes viruses, borrelia and unknown pathogens; and trauma-induced neurodegenerations.

In yet another embodiment, the compounds of the invention are considered useful in the prevention, treatment and inhibition of neuronal hyperexcitation states such as in medicament withdrawal or intoxication.

The invention provides compounds showing effect in one or more of the following tests:
  "Relative efflux through the KCNQ2 channel"
  Which is a measure of the potency of the compound at the target channel
  "Maximum electroshock"
  Which is a measure of seizures induced by non-specific CNS stimulation by electrical means
  "Tilocarpine induced seizures"
  Seizures induced by pilocarpine are often difficult to treat with many existing antiseizure medications and so reflect a model of "drug resistant seizures"

"Electrical seizure-threshold tests" and "Chemical seizure-threshold tests"

These models measure the threshold at which seizures are initiated, thus being models that detect whether compounds could delay seizure initiation.

"Amygdala kindling"

Which is used as a measure of disease progression, as in normal animals the seizures in this model get more severe as the animal receives further stimulations.

According to one particular aspect of the invention, the compounds are KCNQ2 active with an $EC_{50}$ of less than 15000 nM such as less than 10000 nM as measured by the test "Relative efflux through the KCNQ2 channel" which is described below.

According to one particular aspect of the invention, the compounds are KCNQ2 active with an $EC_{50}$ of less than 2000 nM such as less than 1500 nM as measured by the test "Relative efflux through the KCNQ2 channel" which is described below.

According to another particular aspect of the invention, the compounds are KCNQ2 active with an $EC_{50}$ of less than 200 nM such as less than 150 nM as measured by the test "Relative efflux through the KCNQ2 channel" which is described below.

According to another particular aspect of the invention, the compounds have an $ED_{50}$ of less than 15 mg/kg in the test "Maximum electroshock" which is described below.

According to yet another particular aspect of the invention, the compounds have an $ED_{50}$ of less than 5 mg/kg in the test "Maximum electroshock" which is described below.

According to one particular aspect of the invention, the compounds have an $ED_{50}$ of less than 5 mg/kg in the "Electrical seizure-threshold test" and "Chemical seizure-threshold test" which is described below.

Some compounds have few or clinically insignificant side effects. Some of the compounds are thus tested in models of the unwanted sedative, hypothermic and ataxic actions of the compounds.

Some of the compounds have a large therapeutic index between anticonvulsant efficacy and side-effects such as impairment of locomotor activity or ataxic effects as measured by performance on a rotating rod. This means that the compounds will expectedly be well tolerated in patients permitting high doses to be used before side effects are seen. Thereby compliance with the therapy will expectedly be good and administration of high doses may be permitted making the treatment more efficacious in patients who would otherwise have side effects with other medications.

Definitions

The term heteroatom refers to a nitrogen, oxygen or sulphur atom.

Halogen means fluoro, chloro, bromo or iodo.

The expressions $C_{1-6}$-alk(en/yn)yl and $C_{1-6}$-alk(an/en/yn)yl mean a $C_{1-6}$-alkyl, $C_{2-6}$-alkenyl or a $C_{2-6}$-alynyl group.

The term $C_{1-6}$-alkyl refers to a branched or un-branched alkyl group having from one to six carbon atoms inclusive, including but not limited to methyl, ethyl, 1-propyl, 2-propyl, 1-butyl, 2-butyl, 2-methyl-2-propyl and 2-methyl-1-propyl.

Similarly, $C_{2-6}$-alkenyl and $C_{2-6}$-alkynyl, respectively, designate such groups having from two to six carbon atoms, including one double bond and one triple bond respectively, including but not limited to ethenyl, propenyl, butenyl, ethynyl, propynyl and butynyl.

The expression $C_{1-3}$-alk(en/yn)yl means a $C_{1-3}$-alkyl, $C_{2-3}$-alkenyl or a $C_{2-3}$-alkynyl group.

The term $C_{1-3}$-alkyl refers to a branched or un-branched alkyl group having from one to three carbon atoms inclusive, including but not limited to methyl, ethyl, 1-propyl and 2-propyl.

Similarly, $C_{2-3}$-alkenyl and $C_{2-3}$-alkynyl, respectively, designate such groups having from two to three carbon atoms, including one double bond and one triple bond respectively, including but not limited to ethenyl, propenyl, ethynyl and propynyl.

The expressions $C_{3-8}$-cycloalk(en)yl and $C_{3-8}$-cycloalk(an/en)yl mean a $C_{3-8}$-cycloalkyl- or cycloalkenyl group.

The term $C_{3-8}$-cycloalkyl designates a monocyclic or bicyclic carbocycle having three to eight C-atoms, including but not limited to cyclopropyl, cyclopentyl, cyclohexyl, etc.

The expressions $C_{3-6}$-cycloalk(en)yl and $C_{3-6}$-cycloalk(an/en)yl mean a $C_{3-6}$-cycloalkyl- or cycloalkenyl group.

The term $C_{3-6}$-cycloalkyl designates a monocyclic or bicyclic carbocycle having three to six C-atoms, including but not limited to cyclopropyl, cyclopentyl, cyclohexyl, etc.

The term $C_{3-8}$-cycloalkenyl designates a monocyclic or bicyclic carbocycle having three to eight C-atoms and including one double bond.

The term heterocycloalk(en)yl designates monocyclic or bicyclic ring systems wherein the ring is formed by 5 to 8 atoms being selected from the group consisting of carbon atoms and heteroatoms; with the proviso that one or two of the ring forming atoms are independently selected heteroatoms. The term heterocycloalk(en)yl may thus designate a monocyclic or bicyclic ring system wherein the ring is formed by 5 to 8 atoms selected from 3-7 carbon atoms and 1 or 2 heteroatoms selected from N, S, or O. Examples of such ring systems are morpholine, pyrrolidine, piperidine and piperazine.

The term halo-$C_{1-6}$-alk(en/yn)yl designates $C_{1-6}$-alk(en/yn)yl being substituted with one or more halogen atoms, including but not limited to trifluoromethyl. Similarly, halo-$C_{3-8}$-cycloalk(en)yl designates $C_{3-8}$-cycloalk(en)yl being substituted with one or more halogen atoms and halo-heterocycloalk(en)yl designates heterocycloalk(en)yl being substituted with one or more halogen atoms.

The term $NR^{10}R^{10'}$—$C_{1-6}$alk(en/yn)yl designates $C_{1-6}$-alk(en/yn)yl being substituted with $NR^{10}R^{10'}$; $NR^{12}R^{12'}$—$C_{1-6}$-alk(en/yn)yl designates $C_{1-6}$-alk(en/yn)yl being substituted with $NR^{12}R^{12'}$; and $NR^{7}R^{7'}$—$C_{1-6}$-alk(en/yn)yl designates $C_{1-6}$-alk(en/yn)yl being substituted with $NR^{7}R^{7'}$. 2-amino-4-methyl-pentane is an example of such group, the example is not intended to be construed as limiting.

The term $NR^{10}R^{10'}$—$C_{3-8}$-cycloalk(en)yl designates $C_{3-8}$-cycloalk(en)yl being substituted with $NR^{10}R^{10'}$; $NR^{12}R^{12'}$—$C_{3-8}$-cycloalk(en)yl designates $C_{3-8}$-cycloalk(en)yl being substituted with $NR^{12}R^{12'}$; and $NR^{7}R^{7'}$—$C_{3-8}$-cycloalk(en)yl designates $C_{3-8}$-cycloalk(en)yl being substituted with $NR^{7}R^{7'}$. 1-amino-cyclopropane is an example of such group, the example is not intended to be construed as limiting.

The term $NR^{10}R^{10'}$—$C_{3-8}$-cycloalk(en)yl-$C_{1-6}$-alk(en/yn)yl designates $C_{3-8}$-cycloalk(en)yl-$C_{1-6}$-alk(en/yn)yl being substituted with $NR^{10}R^{10'}$; $NR^{12}R^{12'}$—$C_{3-8}$-cycloalk(en)yl-$C_{1-6}$-alk(en/yn)yl designates $C_{3-8}$-cycloalk(en)yl-$C_{1-6}$-alk(en/yn)yl being substituted with $NR^{12}R^{12'}$; and $NR^{7}R^{7'}$—$C_{3-8}$-cycloalk(en)yl-$C_{1-6}$-alk(en/yn)yl designates $C_{3-8}$-cycloalk(en)yl-$C_{1-6}$-alk(en/yn)yl being substituted with $NR^{7}R^{7'}$.

When any of $NR^{12}R^{12'}$—$C_{1-6}$-alk(en/yn)yl, $NR^{12}R^{12'}$—$C_{3-8}$-cycloalk(en)yl, $NR^{12}R^{12'}$—$C_{3-8}$-cycloalk(en)yl-$C_{1-6}$-alk(en/yn)yl is optionally substituted, then any of $C_{1-6}$-alk(en/yn)yl, $C_{3-8}$-cycloalk(en)yl, $C_{3-8}$-cycloalk(en)yl-$C_{1-6}$-alk(en/yn)yl is optionally substituted with one or more substituents independently being $C_{1-6}$-alk(en/yn)yl, $C_{3-8}$-cycloalk(en)yl, $C_{3-8}$-cycloalk(en)yl-$C_{1-6}$-alk(en/yn)yl or Ar.

As used herein, the term acyl refers to formyl, $C_{1-6}$-alk(en/yn)ylcarbonyl, $C_{3-8}$-cycloalk(en)ylcarbonyl, Ar-carbonyl, Ar—$C_{1-6}$-alk(en/yn)ylcarbonyl or a $C_{3-8}$-cycloalk(en)yl-$C_{1-6}$-alk(en/yn)yl-carbonyl group, wherein $C_{1-6}$-alk(en/yn)yl, $C_{3-8}$-cycloalk(en)yl and Ar are as defined above.

When two substituents together with a nitrogen atom form a 5-8 membered saturated or unsaturated ring which optionally contains one further heteroatom, then a monocyclic ring system is formed by 5 to 8 atoms, one or two of said atoms are heteroatoms selected from N, S, or O. Examples of such ring systems are pyrrolidine, piperidine, piperazine, morpholine, pyrrole, oxazolidine, thiazolidine, imidazolidine, azetidine, beta-lactame, tetrazole and pyrazole.

When two adjacent substituents together with an aromatic group to which they are attached form a 5-8 membered ring, which optionally contains one or two heteroatoms, then a ring is formed by 5-8 atoms selected from 3-8 carbon atoms and 0-2 heteroatoms selected from N, S, or O. Such two adjacent substituents may together form:
—$(CH_2)_{n''}$—$CH_2$—, —CH=CH—$(CH_2)_{m''}$—, —$CH_2$—CH=CH—$(CH_2)_{p''}$—, —CH=CH—CH=CH—, —$(CH_2)_{n''}$—O—, —O—$(CH_2)_{m''}$—O—, —$CH_2$—O—$(CH_2)_{p''}$—O—, —$CH_2$—O—$CH_2$—O—$CH_2$—, —$(CH_2)_{n''}$—S—, —S$(CH_2)_{m''}$—S—, —$CH_2$—S—$(CH_2)_{p''}$—S—, —$CH_2$—S—$CH_2$—S—$CH_2$—, —$(CH_2)_{n''}$—NH—, —NH—$(CH_2)_{m''}$—NH—, —$CH_2$—NH—$(CH_2)_{p''}$—NH—, —CH=CH—NH—, —O—$(CH_2)_{m''}$—NH—, —$CH_2$—O—$(CH_2)_{p''}$—NH— or —O—$(CH_2)_{p''}$—NH—$CH_2$—, —S—$(CH_2)_{m''}$—NH—, —N=CH—NH—, —N=CH—O— or —N=CH—S—,
wherein m″ is 1, 2 or 3, n″ is 2, 3 or 4 and p″ is 1 or 2.

The term Ar refers to optionally substituted aromatic systems of 5-10 carbon atoms, wherein 0, 1, 2, 3 or 4 carbon atoms may be replaced by heteroatoms independently selected from N, S, or O. Examples of such Ar groups are optionally substituted phenyl, optionally substituted naphtyl, optionally substituted quinoline, optionally substituted indol, optionally substituted pyridine, optionally substituted pyrimidine, optionally substituted thiophene, optionally substituted furan, optionally substituted thiazole and optionally substituted oxazole. Such optionally substituted Ar groups may be substituted with one or more substituents independently being hydroxy, halogen, $C_{1-6}$-alk(en/yn)yl, $C_{3-8}$-cycloalk(en)yl, $C_{3-8}$-cycloalk(en)yl-$C_{1-6}$-alk(en/yn)yl, halo-$C_{1-6}$-alk(en/yn)yl, $C_{1-6}$-alk(en/yn)yloxy, $C_{3-8}$-alk(en/yn)yloxy, acyl, nitro, cyano, —CO—NH—$C_{1-6}$-alk(en/yn)yl, —CO—N($C_{1-6}$-alk(en/yn)yl)$_2$, —NH$_2$, —NH—$C_{1-6}$-alk(en/yn)yl, —N($C_{1-6}$-alk(en/yn)yl)$_2$, S—$C_{1-6}$-alk(en/yn)yl, —SO$_2$N($C_{1-6}$-alk(en/yn)yl)$_2$ and —SO$_2$NH—$C_{1-6}$-alk(en/yn)yl, SO$_2$—$C_{1-6}$-alk(en/yn)yl and SO$_2$O—$C_{1-6}$-alk(en/yn)yl; or two adjacent substituents may together with the aromatic group form a 5-8 membered ring, which optionally contains one or two heteroatoms and which may be saturated or unsaturated.

The terms $C_{3-8}$-cycloalk(en)yl-$C_{1-6}$-alk(en/yn)yl, $C_{1-6}$-alk(en/yn)yl-$C_{3-8}$-cycloalk(en)yl, $C_{1-6}$-alk(en/yn)yl-heterocycloalk(en)yl, Ar, Ar—$C_{1-6}$-alk(en/yn)yl, Ar—$C_{3-8}$-cycloalk(en)yl, Ar-heterocycloalk(en)yl, Ar—$C_{3-8}$-cycloalk(en)yl-$C_{1-6}$-alk(en/yn)yl, Ar—$C_{1-6}$-alk(en/yn)yl-$C_{3-8}$-cycloalk(en)yl, Ar—$C_{1-6}$-alk(en/yn)yl-heterocycloalk(en)yl, $C_{1-6}$-alk(en/yn)yloxy, $C_{2-6}$-alkenyloxy, $C_{2-6}$-alkynyloxy, $C_{3-8}$-cycloalk(en)yloxy, $C_{1-6}$-alk(en/yn)yloxy-$C_{1-6}$-alk(en/yn)yl, $C_{3-8}$-cycloalk(en)yloxy-$C_{1-6}$-alk(en/yn)yl, $C_{1-6}$-alk(en/yn)yloxy-$C_{3-8}$-cycloalk(en)yl, $C_{1-6}$-alk(en/yn)yloxy-heterocycloalk(en)yl, Ar-oxy-$C_{1-6}$-alk(en/yn)yl, Ar—$C_{1-6}$-alk(en/yn)yloxy-$C_{1-6}$-alk(en/yn)yl, $C_{1-6}$-alk(en/yn)ylcarbonyl, $C_{3-8}$-alk(en/yn)ylcarbonyl, Ar-carbonyl, Ar—$C_{1-6}$-alk(en/yn)ylcarbonyl, $C_{3-8}$-cycloalk(en)yl-$C_{1-6}$-alk(en/yn)ylcarbonyl, —CO—$C_{1-6}$-alk(en/yn)yl, S—$C_{1-6}$-alk(en/yn)yl, SO$_2$—$C_{1-6}$-alk(en/yn)yl and SO$_2$O—$C_{1-6}$-alk(en/yn)yl, $C_{1-6}$-alk(en/yn)yloxy-carbonyl-$C_{1-6}$-alk(en/yn)yl, $C_{3-8}$-cycloalk(en)yloxy-carbonyl-$C_{1-6}$-alk(en/yn)yl, $C_{3-8}$-cycloalk(en)yl-$C_{1-6}$-alk(en/yn)yloxy-carbonyl-$C_{1-6}$-alk(en/yn)yl, acyl, acyl-$C_{1-6}$-alk(en/yn)yl, acyl-$C_{3-8}$-cycloalk(en)yl, acyl-heterocycloalk(en)yl, acyl-$C_{3-8}$-cycloalk(en)yl-$C_{1-6}$-alk(en/yn)yl, acyl-$C_{1-6}$-alk(en/yn)yl-$C_{3-8}$-cycloalk(en)yl, acyl-$C_{1-6}$-alk(en/yn)yl-heterocycloalk(en)yl, hydroxy-$C_{1-6}$-alk(en/yn)yl, hydroxy-$C_{3-8}$-cycloalk(en)yl, hydroxy-heterocycloalk(en)yl, hydroxy-$C_{3-8}$-cycloalk(en)yl-$C_{1-6}$-alk(en/yn)yl, hydroxy-$C_{1-6}$-alk(en/yn)yl-$C_{3-8}$-cycloalk(en)yl, hydroxy-$C_{1-6}$-alk(en/yn)yl-heterocycloalk(en)yl, halo-$C_{1-6}$-alk(en/yn)yl, halo-$C_{3-8}$-cycloalk(en)yl, halo-heterocycloalk(en)yl, halo-$C_{3-8}$-cycloalk(en)yl-$C_{1-6}$-alk(en/yn)yl, halo-$C_{1-6}$-alk(en/yn)yl-$C_{3-8}$-cycloalk(en)yl, halo-$C_{1-6}$-alk(en/yn)yl-heterocycloalk(en)yl, halo-$C_{1-6}$-alk(en/yn)yl-Ar, halo-$C_{3-8}$-cycloalk(en)yl-Ar, halo-$C_{3-8}$-cycloalk(en)yl-$C_{1-6}$ alk(en/yn)yl-Ar, halo-$C_{1-6}$-alk(en/yn)yl-$C_{3-8}$-cycloalk(en)yl-Ar, halo-heterocycloalk(en)yl-Ar, cyano-$C_{1-6}$-alk(en/yn)yl, cyano-$C_{3-8}$-cycloalk(en)yl, cyano-heterocycloalk(en)yl, cyano-$C_{3-8}$-cycloalk(en)yl-$C_{1-6}$-alk(en/yn)yl, cyano-$C_{1-6}$-alk(en/yn)yl-$C_{3-8}$-cycloalk(en)yl, cyano-$C_{1-6}$-alk(en/yn)yl-heterocycloalk(en)yl etc. designate such groups in which the $C_{1-6}$-alk(en/yn)yl, $C_{2-6}$-alkenyl, $C_{2-6}$-alkynyl, $C_{3-8}$-cycloalk(en)yl, heterocycloalk(en)yl, Ar, cyano, halo-$C_{1-6}$-alk(en/yn)yl, halo-$C_{3-8}$-cycloalk(en)yl, halo-heterocycloalk(en)yl and acyl are as defined above.

The salts of the invention are preferably pharmaceutically acceptable salts. Such salts include pharmaceutically acceptable acid addition salts, pharmaceutically acceptable metal salts, ammonium and alkylated ammonium salts.

The pharmaceutically acceptable salts of the invention are preferably acid addition salts. The acid addition salts of the invention are preferably pharmaceutically acceptable salts of the compounds of the invention formed with non-toxic acids. Acid addition salts include salts of inorganic acids as well as organic acids.

Representative examples of suitable inorganic acids include hydrochloric, hydrobromic, hydroiodic, sulfuric, sulfamic, phosphoric and nitric acids and the like. Such acid addition salts can be formed by methods known to the person skilled in the art. Further examples of pharmaceutically acceptable inorganic or organic acid addition salts include the pharmaceutically acceptable salts listed in *J. Pharm. Sci.* 1977, 66, 2, which is incorporated herein by reference.

Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, ethanesulfonic, tartaric, ascorbic, pamoic, gluconic, citraconic, aspartic, stearic, palmitic, EDTA, glycolic, p-aminobenzoic, glutamic, bis-methylenesalicylic, methanesulfonic, ethanedisulfonic, itaconic, benzenesulfonic, p-toluenesulfonic acids, theophylline acetic acids, as well as the 8-halotheophyllines, for example 8-bromotheophylline and the like. Further examples of pharmaceutical acceptable inorganic or organic acid addition salts include the pharmaceutically acceptable salts listed in J. Pharm. Sci. 1977, 66, 2, which is incorporated herein by reference.

Examples of metal salts include lithium, sodium, potassium, magnesium salts and the like.

Examples of ammonium and alkylated ammonium salts include ammonium, methyl-, dimethyl-, trimethyl-, ethyl-, hydroxyethyl-, diethyl-, n-butyl-, sec-butyl-, tert-butyl-, tetramethylammonium salts and the like.

Also intended as pharmaceutically acceptable acid addition salts are the hydrates, which the present compounds are able to form.

The compounds of the present invention may have one or more asymmetric centres and it is intended that any optical isomers, as separated, pure or partially purified optical isomers or racemic mixtures thereof are included within the scope of the invention.

Furthermore, when a double bond or a fully or partially saturated ring system is present in the molecule geometric isomers may be formed. It is intended that any geometric isomers, as separated, pure or partially purified geometric isomers or mixtures thereof are included within the scope of the invention. Likewise, molecules having a bond with restricted rotation may form geometric isomers. These are also intended to be included within the scope of the present invention.

Furthermore, some of the compounds of the present invention may exist in different tautomeric forms and it is intended that any tautomeric forms that the compounds are able to form are included within the scope of the present invention.

The compounds of this invention may exist in unsolvated as well as in solvated forms with solvents such as water, ethanol and the like. In general, the solvated forms are considered equivalent to the unsolvated forms for the purposes of this invention.

Some of the compounds of the present invention contain chiral centres and such compounds exist in the form of isomers (i.e. enantiomers). The invention includes all such isomers and any mixtures thereof including racemic mixtures.

Racemic forms can be resolved into the optical antipodes by known methods, for example, by separation of diastereomeric salts thereof with an optically active acid, and liberating the optically active amine compound by treatment with a base. Another method for resolving racemates into the optical antipodes is based upon chromatography on an optically active matrix. Racemic compounds of the present invention can also be resolved into their optical antipodes, e.g. by fractional crystallization of d- or l- (tartrates, mandelates or camphorsulphonate) salts. The compounds of the present invention may also be resolved by the formation of diastereomeric derivatives.

Additional methods for the resolution of optical isomers, known to those skilled in the art, may be used. Such methods include those discussed by J. Jaques, A. Collet and S. Wilen in "Enantiomers, Racemates, and Resolutions", John Wiley and Sons, New York (1981).

Optically active compounds can also be prepared from optically active starting materials.

The invention also encompasses prodrugs of the present compounds, which on administration undergo chemical conversion by metabolic processes before becoming pharmacologically active substances. In general, such prodrugs will be functional derivatives of the compounds of the general formulas I, XXIX, XXX, XXXI, XXXII or XXXIII, which are readily convertible in vivo into the required compound of the formulas I, XXIX, XXX, XXXI, XXXII or XXXIII. Conventional procedures for the selection and preparation of suitable prodrug derivatives are described, for example, in "Design of Prodrugs", ed. H. Bundgaard, Elsevier, 1985.

The invention also encompasses active metabolites of the present compounds.

Whenever mentioned in relation to the compounds of the formulas I, XXIX, XXX, XXXI, XXXII or XXXIII, the terms epilepsy and epilepsies embrace any of the epilepsies, epileptic syndromes and epileptic seizures referred to in International League Against Epilepsy: Proposal for revised clinical and electroencephalographic classification of epileptic seizures. Commission on Classification and Terminology of the International League Against Epilepsy. *Epilepsia* 1981 22: 489-501 and in International League Against Epilepsy: Proposal for revised classification of epilepsies and epileptic syndromes. Commission on Classification and Terminology of the International League Against Epilepsy. *Epilepsia* 1939 30(4): 389-399.

Whenever mentioned in relation to the compounds of the formulas I, XXIX, XXX, XXXI, XXXII or XXXIII, the term anxiety disorders embraces conditions and diseases related to panic attack, agoraphobia, panic disorder with agoraphobia, panic disorder without agoraphobia, agoraphobia without history of panic disorder, specific phobia, social phobia, obsessive-compulsive disorder, posttraumatic stress disorder, acute stress disorders, generalized anxiety disorder, anxiety disorder due to general medical condition, substance-induced anxiety disorder, separation anxiety disorder, adjustment disorders and anxiety disorder not otherwise specified as defined by American Psychiatric Association *Diagnostic and statistical manual of mental disorders*, 4ed 1994: 110-113, 393-444 and 623-627.

Pharmaceutical Compositions

The compounds of this invention are generally utilized as the free base or as a pharmaceutically acceptable salt thereof. Representative examples are mentioned above.

If desired, the pharmaceutical composition of the invention may comprise the compound of formula I in combination with further pharmacologically active substances such as those described in the foregoing.

The compounds of the invention may be administered alone or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19 Edition, Gennaro, Ed., Mack Publishing Co., Easton, Pa., 1995.

The pharmaceutical compositions may be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route, the oral route being preferred. It will be appreciated that the preferred route will depend on the general condition and age of the subject to be treated, the nature of the condition to be treated and the active ingredient chosen.

Pharmaceutical compositions for oral administration include solid dosage forms such as capsules, tablets, dragees, pills, lozenges, powders and granules. Where appropriate, they can be prepared with coatings such as enteric coatings or they can be formulated so as to provide controlled release of the active ingredient such as sustained or prolonged release according to methods well known in the art.

Liquid dosage forms for oral administration include solutions, emulsions, suspensions, syrups and elixirs.

Pharmaceutical compositions for parenteral administration include sterile aqueous and nonaqueous injectable solutions, dispersions, suspensions or emulsions as well as sterile powders to be reconstituted in sterile injectable solutions or dispersions prior to use. Depot injectable formulations are also contemplated as being within the scope of the present invention.

Other suitable administration forms include suppositories, sprays, ointments, cremes, gels, inhalants, dermal patches, implants etc.

The pharmaceutical compositions of this invention or those which are manufactured in accordance with this invention may be administered by any suitable route, for example orally in the form of tablets, capsules, powders, syrups, etc., or parenterally in the form of solutions for injection. For preparing such compositions, methods well known in the art may be used, and any pharmaceutically acceptable carriers, diluents, excipients or other additives normally used in the art may be used.

A typical oral dosage is in the range of from about 0.001 to about 100 mg/kg body weight per day, preferably from about 0.01 to about 50 mg/kg body weight per day, and more preferred from about 0.05 to about 10 mg/kg body weight per day administered in one or more dosages such as 1 to 3 dosages. The exact dosage will depend upon the frequency and mode of administration, the sex, age, weight and general condition of the subject treated, the nature and severity of the condition treated and any concomitant diseases to be treated and other factors evident to those skilled in the art.

The formulations may conveniently be presented in unit dosage form by methods known to those skilled in the art. A typical unit dosage form for oral administration one or more times per day such as 1 to 3 times per day may contain from 0.05 to about 1000 mg, preferably from about 0.1 to about 500 mg, and more preferred from about 0.5 mg to about 200 mg.

For parenteral routes such as intravenous, intrathecal, intramuscular and similar administration, typically doses are in the order of about half the dose employed for oral administration.

The compounds of this invention are generally utilized as the free substance or as a pharmaceutically acceptable salt thereof. One example is a base addition salt of a compound having the utility of a free acid. When a compound of the invention contains a free acid such salts may be prepared in a conventional manner by treating a solution or suspension of a free acid of the compound of the invention with a chemical equivalent of a pharmaceutically acceptable base. Representative examples are mentioned above.

For parenteral administration, solutions of the novel compounds of the invention in sterile aqueous solution, aqueous propylene glycol, aqueous vitamin E or sesame or peanut oil may be employed. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Solutions for injections may be prepared by dissolving the active ingredient and possible additives in a part of the solvent for injection, preferably sterile water, adjusting the solution to a desired volume, sterilising the solution and filling it in suitable ampules or vials. Any suitable additive conventionally used in the art may be added, such as tonicity agents, preservatives, antioxidants, etc.

Suitable pharmaceutical carriers include inert solid diluents or fillers, sterile aqueous solution and various organic solvents.

Examples of solid carriers are lactose, terra alba, sucrose, cyclodextrin, talc, agar, pectin, acacia, stearic acid and lower alkyl ethers of cellulose corn starch, potato starch, talcum, magnesium stearate, gelatine, lactose, gums, and the like.

Any other adjuvants or additives usually used for such purposes such as colourings, flavourings, preservatives etc. may be used provided that they are compatible with the active ingredients.

Examples of liquid carriers are syrup, peanut oil, olive oil, phospho lipids, fatty acids, fatty acid amines, polyoxyethylene and water. Similarly, the carrier or diluent may include any sustained release material known in the art, such as glyceryl monostearate or glyceryl distearate, alone or mixed with a wax.

The pharmaceutical compositions formed by combining the novel compounds of the invention and the pharmaceutical acceptable carriers are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units such as capsules or tablets, each containing a predetermined amount of the active ingredient, and which may include one or more suitable excipients. Furthermore, the orally available formulations may be in the form of a powder or granules, a solution or suspension in an aqueous or non-aqueous liquid, or an oil-in-water or water-in-oil liquid emulsion.

If a solid carrier is used for oral administration, the preparation may be tablette, placed in a hard gelatine capsule in powder or pellet form or it can be in the form of a troche or lozenge.

The amount of solid carrier will vary widely but will usually be from about 25 mg to about 1 g.

If a liquid carrier is used, the preparation may be in the form of a syrup, emulsion, soft gelatine capsule or sterile injectable liquid such as an aqueous or non-aqueous liquid suspension or solution.

If desired, the pharmaceutical composition of the invention may comprise the compound of the formulae I, XXIX, XXX, XXXI, XXXII or XXXIII in combination with further pharmacologically active substances such as those described in the foregoing.

Typical examples of recipes for the formulation of the invention are as follows:

1) Tablets containing 5.0 mg of a compound of the invention calculated as the free base:

| | |
|---|---|
| Compound of formula I, XXIX, XXX, XXXI, XXXII or XXXIII | 5.0 mg |
| Lactose | 60 mg |
| Maize starch | 30 mg |
| Hydroxypropylcellulose | 2.4 mg |
| Microcrystalline cellulose | 19.2 mg |
| Croscarmellose Sodium Type A | 2.4 mg |
| Magnesium stearate | 0.84 mg |

2) Tablets containing 0.5 mg of a compound of the invention calculated as the free base:

| | |
|---|---|
| Compound of formula I, XXIX, XXX, XXXI, XXXII or XXXIII | 0.5 mg |
| Lactose | 46.9 mg |
| Maize starch | 23.5 mg |
| Povidone | 1.8 mg |
| Microcrystalline cellulose | 14.4 mg |
| Croscarmellose Sodium Type A | 1.8 mg |
| Magnesium stearate | 0.63 mg |

3) Syrup containing per milliliter:

| | |
|---|---|
| Compound of formula I, XXIX, XXX, XXXI, XXXII or XXXIII | 25 mg |
| Sorbitol | 500 mg |
| Hydroxypropylcellulose | 15 mg |
| Glycerol | 50 mg |
| Methyl-paraben | 1 mg |
| Propyl-paraben | 0.1 mg |
| Ethanol | 0.005 mL |
| Flavour | 0.05 mg |
| Saccharin sodium | 0.5 mg |
| Water | ad 1 mL |

4) Solution for injection containing per milliliter:

| | |
|---|---|
| Compound of formula I, XXIX, XXX, XXXI, XXXII or XXXIII | 0.5 mg |
| Sorbitol | 5.1 mg |
| Acetic Acid | 0.05 mg |
| Saccharin sodium | 0.5 mg |
| Water | ad 1 mL |

Preparation of the Compounds of the Invention

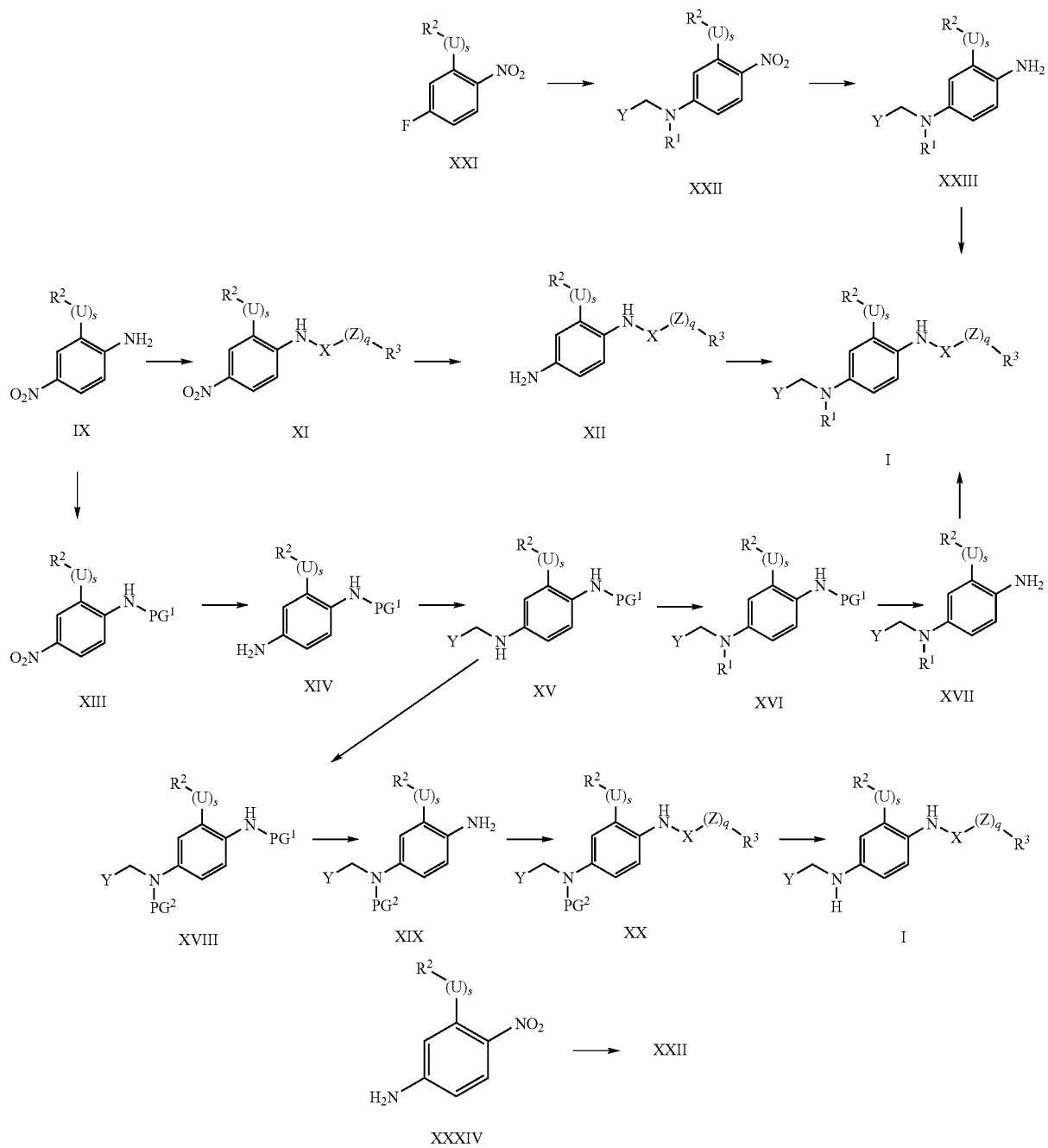

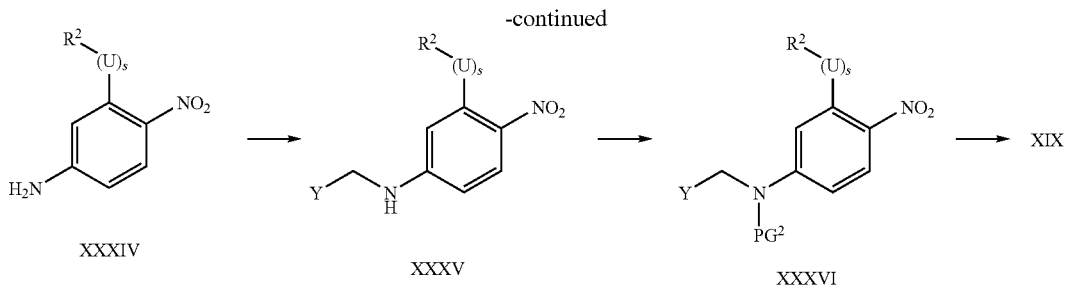

The compounds of the invention of the general formula I, wherein a, b, c, d, e, f, g, h, s, q, U, W, Z, $R^1$, $R^2$, $R^3$, $R^5$, $R^6$, $R^{6'}$, $R^7$, $R^{7'}$, $R^8$, $R^9$, $R^{9'}$, $R^{10}$, $R^{11}$, $R^{12}$ and $R^{12'}$ are defined under formula I may be prepared by the methods as described below and as represented in the scheme.

Substituted 4-nitroanilines of the general formula IX or XI are commercially available, described in the literature or prepared according to methods known to chemists skilled in the art. In particular, compounds of the general formula IX or XI with s being 0 and $R^2$ being substituted aryl or substituted heteroaryl as defined above such as furanyl, thienyl, phenyl, pyridinyl can be prepared from corresponding compounds with $R^2$ being I or Br by means of cross-coupling reactions known to chemists skilled in the art, such as Suzuki coupling, Stille coupling, or other transition metal catalyzed cross-coupling reactions [D. W. Knight "Coupling Reactions Between sp2 Carbon Centers" in *Comprehensive Organic Synthesis*, v. 3, pp. 481-520, Pergamon Press 1991]. Alternatively, 4-nitroanilines with the general formula IX or XI can be prepared from the corresponding 2-substituted aniline in the protected or unprotected form by nitration known to chemists skilled in the art [R. Behnisch "Aromatische Nitro-Verbindungen" in *Methoden der Organische Chemie/(Houben-Weyl)* p. 255, v. E16d, Thieme: 1992]. In particular, this method can be applied for compounds with the general formula IX or XI where U is S, $SO_2$, or $SO_2NR^{11}$. Also, compounds of the general formula IX or XI where U is S can be converted into compounds of the general formula IX or XI where U is $SO_2$ by oxidation according to methods known to the chemist skilled in the art, for example by oxidation with 3-chloroperoxybenzoic acid or $NaIO_4$ in the presence of $RuCl_3$ as a catalyst.

Compounds of the general formula XI are also prepared from compounds of general formula IX by the reaction with suitable electrophilic reagents forming an $R^3$-$(Z)_q$-X group, such as, but not limited to, alkyl, aryl, or heteroaryl chloroformiates or carbamoyl chlorides, carbonic acid anhydrides, acid fluorides, acid chlorides, acid bromides, acid iodides, activated esters, activated carbonic acids with activating reagents such as carbodiimides, sulfonyl chlorides, or isocyanates in suitable solvents, such as acetonitrile, tetrahydrofuran, 1,2-dichloroethane, or methylene chloride, at a suitable temperature, such as room temperature or reflux, achieved by conventional heating or under microwave irradiation, with or without addition of bases, such magnesium oxide, potassium carbonate, sodium hydride, trialkylamines, sodium- or potassium alcoholates, sodium or potassium carbonate, sodium or potassium bicarbonate, or pyridine, reactions well known to the chemist skilled in the art.

Additionally, for further variation of $R^2$, compounds of the general formula XI, wherein $R^2$ is methyl, U is oxygen, and s is 1, can be demethylated by methods known to chemists skilled in the art, such as treatment with boron tribromide in a suitable solvent, such as dichloromethane, at a suitable temperature, such as 0° C. or room temperature. The resulting phenols can then be transformed into compounds of the general formula XI, wherein U is oxygen, and s is 1, by methods known to chemists skilled in the art. Such methods include: (a) the reaction with electrophiles, such as alkyl chlorides, alkyl bromides, alkyl iodides, benzyl chlorides, benzyl bromides, benzyl iodides, carbonic acid chlorides, carbonic acid bromides, or carbonic acid anhydrides in the presence of suitable bases, such as potassium carbonate, in a suitable solvent, such as tetrahydrofuran, N,N-dimethylformamide, or 1,2-dichloroethane, at suitable temperatures, such as room temperature or reflux temperature; (b) the reaction with alkyl, benzylic, or heteroarylalkyl alcohols under conditions known as the Mitsunobu reaction (O. Mitsunobu *Synthesis* 1981, 1).

The nitro group in compounds of the general formula XI can be reduced with suitable reducing agents such as zinc or iron powder in the presence of acid such as acetic acid or aqueous hydrochloric acid, or hydrogen gas or ammonium formiate in the presence of suitable hydrogenation catalyst such as palladium on activated carbon in suitable solvents such as methanol, ethanol, or tetrahydrofuran, at suitable temperatures or under ultrasonic irradiation, to obtain anilines with the general formula XII. Alternatively, tin (R) chloride or sodium dithionite can be used as reducing agents under conditions well known to the chemist skilled in the art.

Obtained anilines with the general formula XII are subjected to reductive alkylation reactions, known to chemists skilled in the art, with aldehydes of the general formula YCHO where Y is defined as above in suitable solvents such as methanol, ethanol, xylene, tetrahydrofuran, acetonitrile, or mixtures thereof, at suitable temperatures with the formation of intermediate imines which can be reduced in situ or can be separated by evaporation of the solvent or crystallisation. They are reduced to the compounds of the invention of the general formula I, where $R^1$ is hydrogen, with reducing agents, such as sodium borohydrate or sodium cyanoborohydrate, in a suitable solvent, such as ethanol, methanol or acetonitrile with or without addition of catalytic amounts of acid, such as acetic acid, at suitable temperatures.

Optionally, for variation of $R^1$, the obtained compounds of the general formula I where $R^1$ is hydrogen can be further derivatized by the second reductive alkylation procedure using suitable aldehydes and reducing agents such as sodium cyanoborohydrate, as described above. This procedure can be performed in situ after the first reductive alkylation with aldehydes of the general formula YCHO. Alternatively, $R^1$ can be introduced by the electrophilic substitution reaction with the appropriate electrophiles of the general formula $R^1$-LG, where LG is a suitable leaving group such as iodide, bromide, or sulphonate under conditions known to the chemist skilled in the art.

For the further variation of $R^3$, Z and X, the compounds of the invention with the general formula I can be obtained by an alternative route:

Compounds with the general formula XIII may be prepared by protection of the aniline nitrogen in the substituted 4-nitro anilines with the general formula IX with an appropriate protecting group (PG$^1$) [*Protective Groups in Organic Synthesis*, 3rd Edition T. W. Greene, P. G. M. Wuts, Wiley Interscience 1999], such as a trifloroacetyl group known to chemists skilled in the art as TFA group, by reaction with the reagent forming the protective group such as trifluoroacetic acid anhydride in a suitable solvent, such as 1,2-dichloroethane at appropriate temperatures.

Anilines with the general formula XIV are obtained by reduction of the nitro group according to methods known to chemists skilled in the art, as described above. Then they are subjected to the reductive alkylation reactions as described above, with the aldehydes of the general formula YCHO to furnish compounds with the general formula XV.

Compounds with the general formula XV are subjected to the second reductive alkylation step, as described above, to furnish compounds with the general formula XVI, where PG$^1$ is TFA. Then the TFA group can be removed by methods known to chemists skilled in the art, such as hydrolysis with aqueous potassium carbonate in an appropriate solvent, such as methanol, at a suitable temperature, furnishing compounds of the general formula XVII.

The compounds of the invention with the general formula I where $R^1$ is not hydrogen are obtained from anilines with the general formula XVII by the reaction with suitable electrophilic reagents forming a $R^3$-(Z)$_q$-X group such as alkyl, aryl or heteroaryl chloroformiates or carbamoyl chlorides, acid chlorides, acid bromides, acid iodides, sulfonyl chlorides, isocyanates, carbonic acid anhydrides, activated carbonic acids with activating reagents such as carbodiimides or others as known to chemists skilled in the art, in the suitable solvents, such as acetonitrile, tetrahydrofuran, 1,2-dichloroethane, or methylene chloride at a suitable temperature, such as room temperature or reflux, with or without addition of bases, such as magnesium oxide, potassium carbonate, trialkylamines, or pyridine, or other methods as described above.

For the compounds of the invention with general formula I wherein $R^1$ is hydrogen, compounds with the general formula XV are subjected to the protection with appropriate protective group (PG$^2$), known to chemists skilled in the art [*Protective Groups in Organic Synthesis*, 3rd Edition T. W. Greene, P. G. M. Wuts, Wiley Interscience 1999], to furnish compounds with the general formula XVIII. In particular, compounds of the general formula XVIII where PG$^2$ is tert-butylcarbonyl group, known to chemists skilled in the art as Boc group, can be prepared with the appropriate reagent forming protective group such as tert-butyl carbonic acid anhydride in an appropriate solvent such as acetonitrile and at appropriate temperature such as +80° C., to furnish compounds of the general formula XVIII where PG$^2$ is Boc. Then the TFA protective group (PG$^1$) is removed, as described above, to furnish compounds with the general formula XIX, followed by derivatisation with appropriate electrophiles forming $R^3$-(Z)$_q$-X group to furnish compounds with the general formula XX, as described above.

Alternatively, compounds of the general formula XIX can be prepared from 4-nitroanilines in three steps as follows: reductive alkylation of compounds of the general formula XXXIV as described above will furnish compounds of the general formula XXXV, which can then be protected e.g. using di-tert-butyldicarbonate and dimethylaminopyridine in a suitable solvent such as tetrahydrofuran, thus yielding compounds of the general formula XXXVI, which can then be reduced to compounds of the general formula XIX by an appropriate reducing agent such as Na$_2$S$_2$O$_4$ as described above.

Finally, the compounds of the invention with general formula I wherein $R^1$ is hydrogen are obtained from the compounds with the general formula X by means of deprotection of PG$^2$ by the methods known to chemists skilled in the art. In particular, the Boc protective group can be cleaved by the methods known to chemists skilled in the art such as deprotection with an appropriate acid, for example trifluoroacetic acid, in the absence or presence of solvent such as methylene chloride or toluene at appropriate temperatures.

Alternatively, compounds of the general formula I can be prepared by a route as follows:

Compounds of the general formula XXI, wherein $R^2$, U, and s are as defined above, are commercially available or prepared by methods known to the chemist skilled in the art. These include the reactions of 5-fluoro-2-nitrophenol under Mitsunobu-, alkylation- or acylation conditions as described above for the synthesis of compounds of the general formula XI from phenols. Nucleophilic aromatic substitution with amines of the type Y—CH$_2$—NH—R$^1$, a reaction well known to chemists skilled in the art, furnishes compounds with the general formula XXII. Alternatively, compounds with the general formula XXII can be prepared by reductive alkylation as described above of 4-nitroanilines of the general formula XXXIV. Compounds with the general formula XXIII may be prepared by the reduction of the nitro group, carried out under the conditions as described above for the synthesis of compounds of the general structures XII. The reaction of compounds with the the general formula XXIII with suitable electrophilic reagents forming an $R^3$-(Z)$_q$-X group, as described above for compounds of the general formula XI, furnishes the compounds of the invention with the general formula I.

Alternatively, compounds of the general formula I with s being 0 and $R^2$ being substituted aryl or substituted heteroaryl as defined above such as furanyl, thienyl, phenyl, pyridinyl can be prepared from the corresponding compounds with $R^2$ being I or Br by means of cross-coupling reactions, as described above.

EXAMPLES

Analytical LC-MSdata (LC-MS=LC/MS) were obtained on a PE Sciex API 150EX instrument equipped with an APPI (atmospheric pressure photo ionisation) ion source and Shimadzu LC-8A/SLC-10A LC system. Column: 30×4.6 mm Waters Symmmetry C18 column with 3.5 μm particle size; Solventsystem: A=water/trifluoroacetic acid (100:0.05) and B=water/acetonitrile/trifluoroacetic acid (5:95:0.03); Method: Linear gradient elution with 90% A to 100% B in 4 minutes and with a flow rate of 2 mL/minute. LC/MS-TOF (time-of-flight) data were obtained on a micromass LCT 4-ways MUX equipped with a Waters 2488/Sedex 754 detector system. Column: 30×4.6 mm Waters Symmetry C18 column with 3.5 m particle size; Solventsystem: A=water/trifluoroacetic acid (100:0.05) and B=water/acetonitrile/ trifluoroacetic acid (5:95:0.03); Method: Linear gradient elution with 90% A to 100% B in 4 minutes and with a flow rate of 2 mL/minute. The values for the found molecular ions (m/z, wherein m is the molecular ion mass and z is the charge) are assigned to the molecular mass (M), composed of the most abundant isotopes, optionally plus or minus fragments. In the examples with [M+3]$^+$ or [M+2]$^+$ assignments, the reported m/z values correspond to the highest peak selected from several molecular ion peaks with different isotope composition and the molecular mass M is calculated based on the most abundant isotope distribution. Purity was determined by integration of the UV (254 nm) and ELSD trace. The retention times (RT) are expressed in minutes.

Preparative LC-MS-purification was performed on the same PE Sciex API 150EX instrument. Column: 50×20 mm YMC ODS-A with 5 μm particle size; Method: Linear gradient elution with 80% A to 100% B in 7 minutes and with a flow rate of 22.7 mL/minute. Fraction collection was performed by split-flow MS detection.

$^1$H NMR spectra were recorded at 500.13 MHz or at 250.13 MHz, both on a Bruker Avance DRX500 or on a Bruker AC 250 instrument, respectively. Deuterated chloroform (99.8% D) or dimethyl sulfoxide (99.8% D) were used as solvents. TMS was used as internal reference standard. Chemical shift values are expressed in ppm-values. The following abbreviations are used for multiplicity of NMR signals: s=singlet, d=doublet, t=triplet, q=quartet, qui=quintet, h=heptet, dd=double doublet, dt=double triplet, dq=double quartet, tt=triplet of triplets, m=multiplet and br. s=broad singlet, br. d=broad doublet, br. t=broad triplet.

Preparation of Intermediates

N-(p-Fluorobenzyl)-methylamine was synthesised according to the procedure described by G. M. Singer and A. W. Andrews *J. Med. Chem.* 1983, 26, 309. 2-Iodo-4-nitroaniline was prepared according to the procedure described by J. J. Pak, T. J. R. Weakley, and M. M Haley *J. Amer. Chem. Soc.* 1999, 121, 8182.

Preparation of Intermediates of the General Formula XI (2-Chloro-4-nitrophenyl)-carbamic acid ethyl ester A suspension of MgO (2.0 g), 2-chloro-4-nitroaniline (3.768 g, 21.83 mmol) and ethyl chloroformate (5 mL) in acetonitrile (25 mL) was heated to reflux temperature for 4 hours followed by addition of more ethyl chloroformate (4 mL). The heating was continued until full conversion (20 hours) then the reaction mixture was filtered via a plug of $SiO_2$ (5 g) with ethyl acetate as an eluent. Evaporation in vacuo (50° C.) gave 5.8 g (100% yield) of crude title compound which was used in the next step without further purification. LC/MS (m/z) 245 ([M+H]$^+$); RT=2.95, (UV, ELSD) 96%, 98.5%. $^1$H NMR (DMSO-d$_6$): 1.27 (t, 3H), 4.19 (q, 2H), 8.06 (d, 1H), 8.19 (dd, 1H), 8.30 (d, 1H), 9.49 (s, NH).

The following compounds were prepared analogously using appropriate chloroformates:

(2-Chloro-4-nitrophenyl)-carbamic acid propyl ester

Propyl chloroformate and tetrahydrofuran were used instead. The title compound was crystallized by addition of diisopropyl ether to the crude product and separated by filtration. Yield 3.3 g (62%), colorless solid. $^1$H NMR (DMSO-d$_6$): 0.94 (t, 3H), 1.67 (m, 2H), 4.10 (t, 2H), 8.06 (d, 1H), 8.20 (dd, 1H), 8.31 (d, 1H), 9.52 (s, NH).

(4-Nitrophenyl)-carbamic acid propyl ester

Reaction was performed at room temperature in acetone as a solvent. The product was used in the next step without purification.

(4-Nitrophenyl)-carbamic acid ethyl ester

Reaction was performed at room temperature in acetone as a solvent. The product was used in the next step without purification.

(2-Methoxy-4-nitrophenyl)-carbamic acid methyl ester

Reaction was performed at room temperature in acetone as a solvent. The product was used in the next step without purification.

(2-Methoxy-4-nitrophenyl)-carbamic acid isopropyl ester

Reaction was performed at room temperature in acetone as a solvent. The product was used in the next step without purification.

(2-Methoxy-4-nitrophenyl)-carbamic acid propyl ester

Reaction was performed at room temperature in acetone as a solvent. The product was used in the next step without purification.

(2-Methoxy-4-nitrophenyl)-carbamic acid 4-fluorophenyl ester

Reaction was performed at room temperature in acetone as a solvent. The product was used in the next step without purification.

(2-Methyl-4-nitrophenyl)-carbamic acid ethyl ester

The crude product was used in the next step without further purification.
LC/MS (m/z) 207.9 ([M−16]$^+$); RT=2.69, (UV, ELSD) 75%, 99.7%.

(2-Methyl-4-nitrophenyl)-carbamic acid propyl ester

The crude product was used in the next step without further purification.
LC/MS (m/z) 223.1 ([M−15]$^+$); RT=2.97, (UV, ELSD) 62%, 99.7%.

(2-Bromo-4-nitrophenyl)-carbamic acid propyl ester

The crude product was purified by crystallisation from ethyl acetate-hexane. $^1$H NMR (DMSO-d$_6$): 0.94 (t, 3H), 1.66 (m, 2H), 4.10 (t, 2H), 7.97 (d, 1H), 8.23 (dd, 1H), 8.44 (d, 1H), 9.28 (br, s, NH).

(2-Iodo-4-nitrophenyl)-carbamic acid propyl ester

The crude product was purified by crystallisation from ethyl acetate-hexane. Pale yellow needles. $^1$H NMR (DMSO-d$_6$): 0.94 (t, 3H), 1.66 (m, 2H), 4.09 (t, 2H), 7.79 (d, 1H), 8.24 (dd, 1H), 8.60 (d, 1H), 9.07 (br. s, NH). LC/MS (m/z) 335.0 ([M-O]$^+$); RT=3.40, (UV, ELSD) 99%, 100%.

(4-Nitro-2-cyanophenyl)-carbamic acid propyl ester

Sodium hydride was used instead as a base prior to addition of propyl chloroformate at room temperature. The crude product contaminated with double acylation product was treated with saturated aqueous sodium bicarbonate (NaHCO$_3$) in methanol for 16 hours and purified by flash chromatography. $^1$H NMR (CDCl$_3$): 1.01 (t, 3H), 1.76 (m, 2H), 4.22 (t, 2H), 7.47 (br. s, 1H, NH), 8.43 (dd, 1H), 8.47 (d, 1H), 8.57 (d, 1H).

The following compounds were prepared analogously:

(4-Nitro-2-cyanophenyl)-carbamic acid ethyl ester $^1$H NMR (DMSO-$d_6$): 1.28 (t, 3H), 4.21 (q, 2H), 7.88 (d, 1H), 8.47(dd, 1H), 8.68 (d, 1H), 10.34 (s, 1H, NH). LC/MS (m/z) 220.1 ([M+H]$^+$), RT=2.46, (UV, ELSD) 97%, 98%.

(2-Trifluoromethyl-4-nitrophenyl)-carbamic acid propyl ester $^1$H NMR (CDCl$_3$): 1.00 (t, 3H), 1.75 (m, 2H), 4.20 (t, 2H), 7.26 (br. s, 1H, NH), 8.41 (dd, 1H), 8.50 (d, 1H), 8.57 (d, 1H).

(2-Trifluoromethyl-4-nitrophenyl)-carbamic acid ethyl ester $^1$H NMR (CDCl$_3$): 1.37 (t, 3H), 4.31 (q, 2H), 7.25 (br. s, 1H, NH), 8.41 (dd, 1H), 8.50 (d, 1H), 8.57 (d, 1H).

N-(b 2-Methoxy-4-nitrophenyl)-butyramide

To a cold (ice/water bath) solution of 2-methoxy-4-nitroaniline (4.00 g, 23.8 mmol) in acetonitrile (40 mL) and triethylamine (5 mL) butyryl chloride (2.66 g, 25 mmol) was added. After 30 minutes the obtained suspension was poured into saturated aqueous sodium bicarbonate (NaHCO$_3$) (300 mL). After sonication for 10 minutes the title compound was separated by filtration as a yellow-brown solid, washed with water and dried in vacuo. Yield 5.34 g, 94%. LC/MS (m/z) 238.9 ([M+H]$^+$); RT=2.69, (UV, ELSD) 98%, 99%. $^1$H NMR DMSO-$d_6$): 0.91 (t, 3H), 1.60 (m, 2H), 2.47 (t, 2H), 3.98 (s, 3H, OMe), 7.79 (s, 1H), 7.88 (dd, 1H), 8.39 (d, 1H), 9.50 (s, 1H, NH).

The following compound was prepared analagously using the appropriate acid chloride:

N-(2-Methoxy-4-nitrophenyl)-3,4-dichlorobenzamide

LC/MS (m/z) 313.0 ([M+H—NO]$^+$; RT=3.72, (UV, ELSD) 99%, 100%. $^1$H NMR (DMSO-$d_6$): 4.00 (s, 3H, OMe), 7.82 (d, 1H), 7.88 (d, 1H), 7.93 (m, 2H), 8.17 (d, 1H), 8.20 (s, 1H), 10.01 (s, 1H, NH).

3,3-Dimethyl-N-(2-methyl-4-nitrophenyl)-butyramide

To a solution of 2-methyl-4-nitroaniline (5 g, 32.9 mmol) in acetonitrile (75 mL) tert-butylacetyl chloride (5.3 g, 1.2 eq.) was added. The obtained mixture was distributed into 15 Smith Process Vials and sealed. Each vial was heated and stirred at 150° C. under microwave irradiation for 10 minutes. The combined reaction mixture was evaporated in vacuo to give 9.27 g of solid (100%) which was used in the next step without further purification. LC/MS (m/z) 251.1 ([M+H]$^+$); RT=3.01, (UV, ELSD) 89%, 99.6%. $^1$H NMR (DMSO-$d_6$): 1.05 (s, 9H), 2.33 (s, 2H), 2.36 (s, 3H), 7.91 (d, 1H), 8.05 (dd, 1H), 8.12 (d, 1H), 9.41 (s, 1H, NH).

The following compounds have been prepared analogously:

2,2-Dimethyl-N-(2-methyl-4-nitrophenyl)-propionamide

LC/MS (m/z) 237.1 ([M+H]$^+$); RT=2.72, (UV, ELSD) 96.7%, 98.6%. $^1$H NMR (DMSO-$d_6$): 1.26 (s, 9H), 2.31 (s, 3H), 7.61 (d, 1H), 8.05 (dd, 1H), 8.14 (d, 1H), 9.06 (s, 1H, NH).

2-(4-Fluorophenyl)-N-(2-methyl-4-nitrophenyl)-acetamide

LC/MS (m/z) 288.9 ([M+H]$^+$); RT=2.90, (UV, ELSD) 99.6%, 99.4%. $^1$H NMR (DMSO-$d_6$): 2.34 (s, 3H), 3.79 (s, 2H), 7.18 (t, 2H), 7.39 (dd, 2H), 7.91 (d, 1H), 8.06 (dd, 1H), 8.13 (d, 1H), 9.72 (s, 1H, NH).

2-(4-Fluorophenyl)-N-(2-iodo-4-nitrophenyl)-acetamide

The product was washed with ice-cold acetonitrile.
$^1$H NMR (DMSO-$d_6$): 3.81 (s, 2H), 7.16-7.19 (m, 2H), 7.41-7.44 (m, 2H), 7.87 (d, 1H), 8.23 (dd, 1H), 8.62 (d, 1H), 9.66 (bs, 1H).

(2-Iodo-4-nitrophenyl)-carbamic acid ethyl ester

The product was purified by flash chromatography (silica, heptane/ethyl acetate).
$^1$H NMR (DMSO-$d_6$): 1.27 (t, 3H), 4.18 (q, 2H), 7.80 (d, 1H), 8.24 (dd, 1H), 8.60 (d, 1H), 9.05 (s, 1H).

(2-(Furan-2-yl)-4-nitrophenyl)-carbamic acid propyl ester

The mixture of (2-iodo-4-nitrophenyl)-carbamic acid propyl ester (30 mg, 0.086 mmol), 0.9 M aqueous potassium carbonate (K$_2$CO$_3$) (0.285 mL, 0.257 mmol), palladium (II) acetate (5 mg) and 2-furanboronic acid (48 mg, 0.428 mmol) in acetone (2 mL) was heated to +125° C. for 3 minutes in the sealed vial under microwave irradiation. The obtained reaction mixture was evaporated and the title compound was purified by flash chromatography on SiO$_2$ (5 g, gradient heptane-ethyl acetate). Yield 21 mg, 84%. $^1$H NMR (CDCl$_3$): 1.00 (t, 3H), 1.75 (m, 2H), 4.18 (t, 2H), 6.62 (dd, 1H, furan), 6.79 (d, 1H, furan), 7.64 (d, 1H, furan), 8.16 (dd, 1H), 8.36 (br. s, 1H, NH), 8.39 (d, 1H), 8.48 (d, 1H). LC/MS (m/z) 261.0 ([M+H]$^+$); RT=1.57.

The following compound was prepared analogously with the appropriated boronic acid:

(2-Phenyl-4-nitrophenyl)-carbamic acid propyl ester

The compound was used in the next step without purification.

(2-Methoxy-4-nitrophenylamine)-carbamic acid ethyl ester

2-Methoxy-4-nitrophenylamine (5.0 g) was dissolved in dry dioxane (30 mL) and N,N-diisopropylethylamine (7.8 mL) was added at 0° C. Ethyl chloroformate (4.25 mL) in dioxane (35 mL) was added dropwise, and the resulting mixture was allowed to warm to room temperature and stirred over night. Water (200 mL) was added and the mixture was extracted with ethyl acetate (3×150 mL). The combined organic phase was washed with water (2×200 mL) and brine (200 mL), dried over sodium sulfate, filtered, and evaporated in vacuo. The crude product was recrystallised from ethanol to yield the title compound as colourless solid (4.45 g, 62%).
$^1$H NMR (DMSO-$d_6$): 1.26 (t, 3H), 3.94 (s, 3H), 4.18 (q, 2H), 7.78 (d, 1H), 7.90 (dd, 1H), 8.09 (d, 1H), 8.99 (s, 1H).

(2-Hydroxy-4-nitrophenyl)-carbamic acid ethyl ester (2-Methoxy-4-nitrophenyl)-carbamic acid ethyl ester (2.15 g) was dispensed in 1,2-dichloroethane (20 mL) and cooled to 0° C. Boron tribromide (2.0 mL) in 1,2-dichloroethane (10 mL) was added dropwise. The reaction mixture was stirred 10 minutes at 0° C. and 30 minutes at room temperature. The mixture was again cooled to 0° C., and water (10 mL) was added carefully. The reaction mixture was neutralised with saturated aqueous sodium bicarbonate and aqueous hydrochloric acid (5M). The resulting mixture was extracted with ethyl acetate (3×100 mL). The combined organic phase was washed with water (2×100 mL) and brine (100 mL), dried over magnesium sulfate, filtered, and evaporated in vacuo to yield the title compound as brownish solid (1.96 g, 97%).

$^1$H NMR (DMSO-$d_6$): 1.25 (t, 3H), 4.17 (q, 2H), 7.64 (d, 1H), 7.74 (dd, 1H), 8.01 (d, 1H), 8.69 (s, 1H), 10.96 (br. s, 1H).

(2-Cyclopentyloxy-4-nitrophenyl)-carbamic acid ethyl ester

Cyclopentanol (7.24 mL, 376 mM in dry tetrahydrofuran) was added to triphenylphosphine (1.44 g, polystyrene bound, 1.89 mMol/g) under argon, followed by the addition of a solution of (2-Hydroxy-4-nitrophenyl)-carbamic acid ethyl ester (25.6 mL, 62 mM in dry tetrahydrofuran) and a solution of diethylazodicarboxylate (7.24 mL, 376 mM in dry tetrahydrofuran). The reaction mixture was shaken at room temperature over night. The resin was filtered and washed with tetrahydrofuran (THF) (35 mL) and methanol (35 mL). The combined organic phase was evaporated in vacuo. The crude product was purified by flash chromatography (silica gel, heptane/ethyl acetate, gradient) to yield the title compound as slightly yellow solid (294 mg, 64%).

$^1$H NMR (DMSO-$d_6$): 1.27 (t, 3H), 1.59 (m, 2H), 1.76 (m, 2H), 1.87 (m, 2H), 1.94 (m, 2H), 4.19 (q, 2H), 5.01 (h, 1H), 7.72 (d, 1H), 7.86 (dd, 1H), 8.11 (d, 1H), 8.82 (s, 1H).

The following compounds were prepared in an analogous fashion:

(4-Nitro-2-phenethyloxyphenyl)-carbamic acid ethyl ester $^1$H NMR (DMSO-$d_6$): 1.28 (t, 3H), 3.15 (t, 2H), 4.19 (q, 2H), 4.38 (t, 2H), 7.23 (t, 1H), 7.32 (t, 2H), 7.36 (d, 2H), 7.80 (d, 1H), 7.88 (dd, 1H), 8.08 (d, 1H), 8.66 (s, 1H).

(2-Benzyloxy-4-nitrophenyl)-carbamic acid ethyl ester $^1$H NMR (DMSO-$d_6$): 1.26 (t, 3H), 4.18 (q, 2H), 5.33 (s, 2H), 7.35 (t, 1H), 7.41 (t, 2H), 7.55 (d, 2H), 7.86 (d, 1H), 7.89 (dd, 1H), 8.06 (d, 1H), 8.95 (s, 1H).

(2-Isopropyloxy-4-nitrophenyl)-carbamic acid ethyl ester $^1$H NMR (DMSO-$d_6$): 1.27 (t, 3H), 1.33 (d, 6H), 4.19 (q, 2H), 4.84 (h, 1H), 7.78 (d, 1H), 7.86 (dd, 1H), 8.12 (d, 1H), 8.77 (s, 1H).

Preparation of Intermediates of the General Formula XII (4-Amino-2-methyloxyphenyl)-carbamic acid ethyl ester (2-Methoxy-4-nitrophenyl)-carbamic acid ethyl ester (2.20 g) was dissolved in ethanol (220 mL). Aqueous hydrochloric acid (26 mL, 6 M) and iron powder (4.74 g) were added, and the mixture was stirred at 65° C. for 15 minutes. After cooling to room temperature, the mixture was neutralised with saturated aqueous sodium bicarbonate and extracted with ethyl acetate (3×200 mL). The organic phase was washed with water (2×100 mL) and brine (100 mL), dried over magnesium sulfate, filtered, and evaporated in vacuo. The crude product was dissolved in ethanol (100 mL), and the above procedure was repeated using aqueous hydrochloric acid (26 mL, 6M) and iron powder (3.7 g), to yield the title compound as a dark oil (1.80 g, 93%). $^1$H NMR (DMSO-$d_6$): 1.19 (t, 3H), 3.67 (s, 3H), 4.01 (q, 2H), 4.97 (s, 2H), 6.08 (dd, 1H), 6.23 (d, 1H), 6.97 (br. s, 1H), 7.92 (br. s, 1H).

(4-Amino-2-iodophenyl)-carbamic acid ethyl ester $^1$H NMR (CDCl$_3$): 1.31 (t, 3H), 3.58 (br. s, 2H), 4.21 (q, 2H), 6.52 (br. s, 1H), 6.67 (dd, 1H), 7.12 (d, 1H), 7.60 (br. d, 1H).

The following compound was prepared analogously:

N-(4-Amino-2-iodophenyl)-2-(4-fluorophenyl)-acetamide $^1$H NMR (DMSO-$d_6$): 3.59 (br. s, 2H), 3.73 (s, 2H), 6.65 (dd, 1H), 7.05 (d, 1H), 7.09-7.12 (m, 3H), 7.34-7.37 (m, 2H), 7.82 (d, 1H).

(4-Amino-2-chlorophenyl)-carbamic acid ethyl ester

To a cold (ice/water bath) vigorously stirred solution of crude (2-Chloro-4-nitrophenyl)-carbamic acid ethyl ester (5.8 g, 21.8 mmol) in tetrahydrofuran (THF) (100 mL) and acetic acid (12 mL) zinc powder (20 g) was added by small portions maintaining the temperature below 40° C. The mixture was allowed to warm slowly to room temperature and after reaction completion (1 hour) it was filtered via a plug of SiO$_2$ (20 g) with ethyl acetate as an eluent. The obtained solution was evaporated in vacuo and the crude yellow solid residue (4.9 g) was purified by precipitation from tetrahydrofuran (THF)/heptane to give 3.00 g of the title compound as pale yellow solid, yield 56%. LC/MS (m/z) 214, 216 (M$^+$); RT=1.18, (UV, ELSD) 86%, 97%. $^1$H NMR (DMSO-$d_6$): 1.18 (br. t, 3H), 4.02 (q, 2H), 5.29 (s, 2H, NH$_2$), 6.45 (dd, 1H), 6.61 (d, 1H), 6.98 (br. d, 1H), 8.52 (br. s, NHCO).

The following compounds were prepared analogously:

(4-Amino-2-chlorophenyl)-carbamic acid propyl ester

Yield 84.6% (2.44 g, colorless solid). LC/MS (m/z) 228.1 (M$^+$); RT=1.53, (UV, ELSD) 97.3%, 99%.

(4-Aminophenyl)-carbamic acid propyl ester

Purified by flash chromatography on SiO$_2$ (gradient heptane-ethyl acetate). Dark purple crystalline solid, yield 3.066 g, 63.3%. LC/MS (m/z) 195 ([M+H]$^+$); RT=1.18, (UV, ELSD) 87%, 98.3%.

(4-Aminophenyl)-carbamic acid ethyl ester

LC/MS (m/z) 180.8 ([M+H]$^+$); RT=0.48, (UV, ELSD) 71%, 97%.

(4-Amino-2-methoxyphenyl)-carbamic acid methyl ester

LC/MS (m/z) 197.0 ([M+H]$^+$); RT=0.49, (UV, ELSD) 71%, 98%.

(4-Amino-2-methoxyphenyl)-carbamic acid ethyl ester

LC/MS (m/z) 210.9 ([M+H]⁺); RT=0.98, (UV, ELSD) 69%, 97%.

(4-Amino-2-methoxyphenyl)-carbamic acid isopropyl ester

LC/MS (m/z) 224.0 (M⁺); RT=1.33, (UV, ELSD) 63%, 99%.

(4-Amino-2-methoxyphenyl)-carbamic acid propyl ester

LC/MS (m/z) 224.9 ([M+H]⁺); RT=1.36, (UV, ELSD) 70%, 98%.

(4-Amino-2-methoxyphenyl)-carbamic acid 4-fluorophenyl ester

LC/MS (m/z) 277.0 ([M+H]⁺); RT=1.64, (UV, ELSD) 44%, 93%.

(4-Amino-2-methylphenyl)-carbamic acid propyl ester

LC/MS (m/z) 208.1 (M⁺); RT=1.16, (UV, ELSD) 95%, 100%. $^1$H NMR (CDCl$_3$): 0.96 (t, 3H), 1.68 (m, 2H), 2.17 (s, 3H, Me), 3.59 (br. s, 2H, NH$_2$), 4.09 (t, 2H), 6.14 (br. s, 1H, ArH), 6.51 (m, 2H), 7.32 (br. s, 1H, NH).

(4-Amino-2-methylphenyl)-carbamic acid ethyl ester $^1$H NMR (CDCl$_3$): 1.28 (t, 3H), 2.16 (s, 3H, Me), 3.62 (br. s, 2H, NH$_2$), 4.19 (q, 2H), 6.16 (br. s, 1H, ArH), 6.5 (m, 2H), 7.31 (br. s, 1H, NH). LC/MS (m/z) 195.1 ([M+H]⁺); RT=0.75, (UV, ELSD) 70%, 95%.

(4-Amino-2-trifluoromethylphenyl)-carbamic acid ethyl ester $^1$H NMR (CDCl$_3$): 1.30 (t, 3H), 3.77 (br. s, 2H, NH$_2$), 4.20 (q, 2H), 6.52 (br. s, 1H, ArH), 6.82 (dd, 1H), 6.87 (unres. d, 1H), 7.65 (br. s, 1H, NH).). LC/MS (m/z) 248.1 (M⁺); RT=1.65, (UV, ELSD) 94%, 90%.

(4-Amino-2-trifluoromethylphenyl)-carbamic acid propyl ester $^1$H NMR (CDCl$_3$): 0.96 (t, 3H), 1.69 (m, 2H), 3.76 (br. s, 2H, NH$_2$), 4.11 (t, 2H), 6.51 (br. s, 1H, ArH), 6.81 (dd, 1H), 6.87 (d, 1H), 7.61 (br. s, 1H, NH). LC/MS (m/z) 261.9 (M⁺); RT=2.06, (UV, ELSD) 92%, 98%.

(4-Amino-2-cyanophenyl)-carbamic acid ethyl ester $^1$H NMR (DMSO-d$_6$): 1.21 (t, 3H), 4.07 (q, 2H), 5.49 (br. s, 2H, NH$_2$), 6.81 (m, 2H, ArH), 7.04 (d, 1H), 9.09 (br. s, 1H, NH). LC/MS (m/z) 204.9 (M⁺); RT 1.05, (UV, ELSD) 98%, 99%.

(4-Amino-2-cyanophenyl)-carbamic acid propyl ester $^1$H NMR (CDCl$_3$): 0.98 (t, 3H), 1.71 (m, 2H), 3.72 (br. s, 2H, NH$_2$), 4.13 (t, 2H), 6.81 (br. s, ArH), 6.82 (d, 1H), 6.89 (dd, 1H), 7.83 (br. s, 1H, NH). LC/MS (m/z) 220.1 ([M+H]⁺); RT=1.52, (UV, ELSD) 98%, 100%.

N-(4-Amino-2-methoxyphenyl)-butyramide

LC/MS (m/z) 208.9 ([M+H]⁺); RT=0.77, (UV, ELSD) 81%, 95%. $^1$H NMR (DMSO-d$_6$): 0.89 (t, 3H), 1.56 (m, 2H), 2.22 (t, 2H), 3.4 (very br. s, NH$_2$), 3.69 (s, 3H, OMe), 6.08 (dd, 1H), 6.25 (d, 1H), 7.27 (d, 1H), 8.62 (s, 1H, NH).

N-(4-Amino-2-methoxyphenyl)-3,4-dichlorobenzamide

LC/MS (m/z) 311.2 (M⁺); RT=1.93, (UV, ELSD) 100%, 100%. $^1$H NMR (DMSO-d$_6$): 3.70 (s, 3H, OMe), 5.12 (br. s, 2H, NH$_2$), 6.15 (dd, 1H), 6.30 (d, 1H), 7.09 (d, 1H), 7.77 (d, 1H), 7.91 (dd, 1H), 8.17 (d, 1H), 9.46 (s, 1H, NH).

N-(4-Amino-2-methylphenyl)-3,3-dimethylbutyramide

LC/MS (m/z) 221.1 ([M+H]⁺); RT=1.22, (UV, ELSD) 53.7%, 92.3%. $^1$H NMR (DMSO-d$_6$): 1.02 (s, 9H), 2.02 (s, 3H), 2.11 (s, 2H), 4.89 (br. s, 2H, NH$_2$), 6.33 (dd, 1H), 6.38 (d, 1H), 6.82 (d, 1H), 8.83 (s, 1H, NH).

N-(4-Amino-2-methylphenyl)-2-(4-fluorophenyl)-acetamide

LC/MS (m/z) 259.1 ([M+H]⁺); RT=1.36, (UV, ELSD) 48.1%, 91.4%. $^1$H NMR (DMSO-d$_6$): 1.95 (s, 3H), 3.56 (s, 2H), 4.88 (br. s, 2H, NH$_2$), 6.31 (dd, 1H), 6.38 (d, 1H), 6.83 (d, 1H), 7.14 (t, 2H), 7.35 (dd, 2H), 9.16 (s, 1H, NH).

N-(4-Amino-2-methylphenyl)-2,2-dimethylpropionamide

LC/MS (m/z) 206.9 ([M+H]⁺); RT=0.59, (UV, ELSD) 93%, 95%. $^1$H NMR (DMSO-d$_6$): 1.19 (s, 9H), 1.98 (s, 2H), 4.87 (br. s, 2H, NH$_2$), 6.33 (dd, 1H), 6.39 (d, 1H), 6.71 (d, 1H), 8.55 (s, 1H, NH).

[4-Amino-2-furan-2-yl)-phenyl]-carbamic acid propyl ester $^1$H NMR (CDCl$_3$): 0.96 (t, 3H), 1.68 (m, 2H), 3.65 (br. s, 2H, NH$_2$), 4.10 (t, 2H), 6.50 (dd, 1H, furan), 6.58 (d, 1H, furan), 6.66 (dd, 1H), 6.91 (br. s (unresolved d), 1H), 7.26 (br. s, ArH), 7.52 (d, 1H), 7.72 (br. s, 1H, NH). LC/MS (m/z) 261.0 ([M+H]⁺); RT=1.57.

(2-Phenyl-4-aminophenyl)-carbamic acid propyl ester

LC/MS (m/z) 271.1 ([M+H]⁺); RT=1.75, (UV, ELSD) 57%, 99%.

(4-Amino-2-bromophenyl)-carbamic acid propyl ester

A suspension of iron powder (20 g, excess) and (2-Bromo-4-nitrophenyl)-carbamic acid propyl ester (2.183 g, 7.20 mmol) in ethanol (80 mL) and 6 M aqueous hydrochloric acid (20 mL) was sonicated at room temperature for 10 minutes. The mixture was slowly poured into saturated aqueous sodium bicarbonate (NaHCO$_3$) solution, filtered and extracted with ethyl acetate. The combined organic solution was washed 3 times with saturated aqueous NaHCO$_3$, dried over sodium sulfate (Na$_2$SO$_4$) and evaporated in vacuo to give 1.67 g of the title compound as pale yellow oil which solidified. Yield 85%. LC/MS (m/z) 271.9, 273.8 (M⁺); RT=1.30, (UV, ELSD) 99%, 100%. ¹H NMR (DMSO-d₆): 0.90 (br. s (unresolved t), 3H), 1.59 (br. s (unresolved m), 2H), 3.94 (t, 2H), 5.31 (s, 2H, NH₂), 6.50 (dd, 1H), 6.80 (unresolved d, 1H), 6.96 (br. d, 1H), 8.51 (br. s, NHCO).

The following compound was prepared analogously:

(4-Amino-2-iodophenyl)-carbamic acid propyl ester

¹H NMR (CDCl₃): 0.97 (t, 3H), 1.69 (m, 2H), 3.59 (br. s, 2H, NH₂), 4.11 (t, 2H), 6.53 (br. s, 1H, ArH), 6.66 (dd, 1H), 7.11 (d, 1H), 7.61 (br. s, 1H, NH). LC/MS (m/z) 320.7 ([M+H]⁺); RT=1.71, (UV, ELSD) 98%, 99%.

Synthesis of Intermediates of the General Formulas XIII-XXIII:

N-(4-Amino-2-chlorophenyl)-2,2,2-trifluoroacetamide

To a suspension of 4-nitro-2-chloroaniline (17.2 g, 0.1 mol) in 1,2-dichloroethane (100 mL) trifluoroacetic anhydride (16 mL, 0.113 mol) was added. Obtained yellow solution was evaporated in vacuo after 5 minutes. The obtained yellow solid of N-(4-nitro-2-chlorophenyl)-2,2,2-trifluoroacetamide was reduced with the Zn-powder in tetrahydrofuran (THF)-acetic acid as described above. The obtained crude product was treated with 2 M hydrochloric acid (150 mL) and diethyl ether. The obtained white precipitate was filtered to give 14.7 g of the title product as hydrochloride salt. The aqueous solution was neutralized with saturated aqueous sodium bicarbonate (NaHCO₃) and filtered to give 4.58 g of the pure title compound as a pale grey solid. ¹H NMR (DMSO-d₆): 5.54 (br. s, 2H, NH₂), 6.53 (dd, 1H), 6.70 (d, 1H), 7.02 (d, 1H), 10.79 (br. s, 1H, NHCO). LC/MS (m/z) 239.8 ([M+H]⁺); RT=1.67, (UV) 100%.

N-{2-Chloro-4-[(5-chloro-thiophen-2-ylmethyl)-amino]-phenyl}-2,2,2-trifluoroacetamide A solution of N-(4-Amino-2-chlorophenyl)-2,2,2-trifluoroacetamide (4.567 g, 19.14 mmol) and 5-chloro-thiophene-2-carboxaldehyde (3.97 g, 27.1 mmol) in anhydrous ethanol (50 mL) was heated to reflux for 15 minutes and evaporated in vacuo at 70° C. (0.1 mbar, 30 min). The obtained crude imine as a crystalline solid was dissolved in methanol followed by addition of sodium cyanoborohydride (NaBH₃CN) in methanol (50 mL) and acetic acid (9 mL) by portions. The obtained reaction mixture was stirred at room temperature for 60 minutes and evaporated in vacuo to small volume. The concentrated solution was quenched with water and filtered after 30 minutes to give 6.98 g (99% yield) of the title compound as a brown-yellow solid. ¹H NMR (DMSO-d₆): 4.43 (d, 2H), 6.63 (dd, 1H), 6.77 (d, 1H), 6.79 (t, 1H, NH), 6.94 (d, 1H), 6.97 (d, 1H), 7.10 (d, 1H), 10.85 (br. s, 1H, NHCO). LC/MS (m/z) 367.9 (M⁺); RT=3.36, (UV, ELSD) 99%, 100%.

N-{2-Chloro-4-[(5-chloro-thiophen-2-ylmethyl)-(methyl)amino]phenyl}-2,2,2-trifluoroacetamide To a mixture of N-{2-Chloro-4-[(5-chloro-thiophen-2-ylmethyl)-amino]-phenyl}-2,2,2-trifluoroacetamide (3.28 g, 8.88 mmol), 37% aqueous formaldehyde (5 mL), and acetic acid (3 mL), sodium cyanoborohydride (NaBH₃CN) (1.1 g) in methanol (10 mL) was added dropwise with stirring during 30 minutes. The reaction mixture was allowed to stand at room temperature for 2 hours and poured into water. After the oil solidified, it was filtered, washed with water and dried in vacuo to give 3.26 g of pale yellow-brown solid. Yield 95%. ¹H NMR (DMSO-d₆): 2.97 (s, 3H, NMe), 4.72 (s, 2H), 6.82 (m, 1H), 6.91 (m, 2H), 6.97 (d, 1H), 7.21 (d, 1H), 10.92 (br. s, 1H, NHCO). LC/MS (m/z) 382.0 (M⁺); RT=3.66, (UV, ELSD) 85%, 98%.

(5-Chloro-thiophen-2-ylmethyl)-[3-chloro-4-(2,2,2-trifluoro-acetylamino)-phenyl]-carbamic acid tert-butyl ester A mixture of N-{2-Chloro-4-[(5-chloro-thiophen-2-ylmethyl)-amino]-phenyl}-2,2,2-trifluoroacetamide (2.219 g, 6.01 mmol), di-tert-butyl dicarbonate (2 g), and acetonitrile (3 mL) was heated to +80° C. until reaction completion (36 hours). During this time additional amount of di-tert-butyl dicarbonate was added (2×1.5 g). The obtained reaction mixture was evaporated in vacuo (80° C., 0.1 mbar) to give the crude title compound which was used in the next step without further purification. ¹H NMR DMSO-d₆): 1.44 (s, 9H), 4.94 (s, 2H), 6.81 (d, 1H), 6.93 (d, 1H), 7.25 (dd, 1H), 7.43 (d, 1H), 7.50 (d, 1H), 11.24 (br. s, 1H, NHCO). LC/MS (m/z) 366.9 ([M-Boc]⁺); RT=3.99, (UV, ELSD) 87%, 96%.

2-Chloro-N(4)-(5-chloro-thiophen-2-ylmethyl)-N(4)-methyl-benzene-1,4-diamine

To a solution of N-{2-Chloro-4-[(5-chloro-thiophen-2-ylmethyl)-(methyl)amino]-phenyl}-2,2,2-trifluoroacetamide (3.118 g) in methanol (MeOH) (50 mL) solution of potassium carbonate (K₂CO₃) (6.4 g) in water (25 mL) was added and the reaction mixture was stirred until reaction completion (24 hours) at room temperature. The obtained reaction mixture was extracted with ethyl acetate, washed with saturated aqueous sodium bicarbonate (NaHCO₃) and evaporated to give 2.26 g of dark brown oil which was used in the next step without further purification. ¹H NMR (DMSO-d₆): 2.71 (s, 3H, NMe), 4.47 (s, 2H), 4.71 (br. s, 2H, NH₂), 6.67-6.75 (m, 3H), 6.82 (d, 1H), 6.93 (d, 1H). LC/MS (m/z) 288.0 ([M+H]⁺); RT=2.07, (UV, ELSD) 85%, 98%.

The following compound was prepared analogously:

(4-Amino-3-chlorophenyl)-(5-chloro-thiophen-2-ylmethyl)-carbamic acid tert-butyl ester ¹H NMR (DMSO-d₆): 1.39 (br. s, 9H, tert-Bu), 4.74 (s, 2H), 5.35 (br. s, 2H, NH₂), 6.67-6.74 (m, 2H), 6.77 (br. d, 1H), 6.90 (d, 1H), 6.97 (d, 1H). LC/MS (m/z) 271.9 ([M-Boc]⁺); RT=3.73, (UV, ELSD) 77%, 97%.

4-Fluoro-2-isopropoxy-1-nitrobenzene

5-Fluoro-2-nitrophenol (48 g) was dissolved in dry tetrahydrofuran (THF) (300 mL). Triphenylphosphine (88 g) and 2-propanol (47 mL) were added, and the resulting mixture was cooled to 0° C. Diisopropylazodicarboxylate (66 mL) was added dropwise. The resulting mixture was allowed to warm to room temperature and stirred over night. The solvent was evaporated in vacuo and the resulting mixture was filtered through silica (heptane/ethyl acetate 1:1). The solvent was evaporated in vacuo and the resulting mixture was recrystallised from heptane/ethyl acetate (1:1). The organic phase was separated from the crystalline solid by filtration, the solvent was evaporated in vacuo, and the remaining product was purified by flash chromatography (silica gel, heptane/ethyl acetate 9:1), yielding the title compound as colourless oil (47.2 g, 78%).

¹H NMR (DMSO-d₆): 1.30 (d, 6H), 4.85 (h, 1H), 6.93 (m, 1H), 7.34 (dd, 1H), 7.96 (dd, 1H).

The following compounds were prepared analogously:

2-Cyclopentyloxy-4-fluoro-1-nitrobenzene $^1$H NMR (DMSO-d$_6$): 1.57-1.78 (m, 6H), 1.86-1.94 (m, 2H), 6.90-6.97 (m, 1H), 7.27-7.32 (m, 1H), 7.98 (dd, 1H).

2-Benzyloxy-4-fluoro-1-nitrobenzene $^1$H NMR (DMSO-d$_6$): 5.33 (s, 2H), 6.96-7.04 (m, 1H), 7.32-7.49 (m, 6H), 8.04 (dd, 1H).

(4-Fluorobenzyl)-(3-isopropoxy-4-nitrophenyl)-(methyl)-amine

4-Fluoro-2-isopropoxy-1-nitrobenzene (1.0 g) was dissolved in dry dimethylsulfoxide (25 mL). Potassium carbonate (1.4 g) and (4-fluorobenzyl)-(methyl)-amine (0.84 g) were added. The resulting mixture was heated to 90° C. over night. After cooling to room temperature, water (75 mL) was added, and the resulting mixture was extracted with ethyl acetate (3×75 mL). The organic phase was dried over sodium sulfate, filtered, and evaporated in vacuo to yield the title compound as slightly yellow solid (1.6 g, 100%).

LC-MS (m/z) 319.1 ([M+H]$^+$); RT=3.43, (UV, ELSD) 85%, 96%.

$^1$H NMR (DMSO-d$_6$): 1.21 (d, 6H), 3.18 (s, 3H), 4.71 (m, 1H), 4.73 (s, 2H), 6.26 (d, 1H), 6.41 (dd, 1H), 7.17 (m, 2H), 7.25 (m, 2H), 7.84 (d, 1H).

The following compounds were prepared analogously:

(3-Benzyloxy-4-nitrophenyl)(4-fluorobenzyl)methylamine

LC-MS (m/z) 320.9 ([M+H-NO$_2$]$^+$); RT=3.54, (UV, ELSD) 96%, 100%.

(3-Cyclopentyloxy-4-nitrophenyl)(4-fluorobenzyl)methylamine

LC-MS (m/z) 299.2 ([M+H-NO$_2$]$^+$); RT=3.64, (UV, ELSD) 96%, 100%.

4-(4-Fluorobenzyl)-(methyl)-amino-2-isopropoxyaniline (4-Fluorobenzyl)-(3-isopropoxy-4-nitrophenyl)-(methyl)-amine (1.60 g) was dissolved in methanol (50 mL). Ammonium formiate (1.91 g) and palladium (10% on charcoal, 0.21 g) were added, and the mixture was stirred for 1.5 hours at room temperature. The reaction mixture was filtered and the solvent was evaporated in vacuo. The residue was dissolved in a small amount of methanol, and concentrated aqueous sodium hydroxide (2 mL) was added. The resulting mixture was filtered through a column of silica gel (ethyl acetate as eluent). The resulting solution was evaporated in vacuo to yield crude title compound as a black oil (0.76 g), which was directly used in the next step.

LC-MS (m/z) 288.9 ([M+H]$^+$); RT=1.91, (UV, ELSD) 80%, 72%.

(5-Chloro-thiophen-2-ylmethyl)-(methyl)-(3-methyl-4-nitrophenyl)-anine

A suspension of 5-chloro-thiophene-2-carbaldehyde (1.61 g, 11.0 mmol), 3-methyl-4-nitroaniline (1.52 g, 10.0 mmol), and Amberlite IRC-84 (100 mg, H$^+$ form) in o-xylene (40 mL) was heated under nitrogen at 140° C. for 5 hour. After cooling to room temperature, the resin was removed by filtration, and volatiles were evaporated. The residue was dissolved in acetonitrile (40 mL) and sodium cyanoborohydride (1.26 g, 20.0 mmol) was added in one portion, followed by acetic acid (1 mL) in several portions over 15 minutes. Formaldehyde solution (37% in water, 2.23 mL, 30.0 mmol) was then added and the mixture was stirred for a further 30 minutes. Volatiles were evaporated and the residue partitioned between saturated aqueous sodium bicarbonate (100 mL) and ethyl acetate (100 mL), and the aqueous phase was extracted with ethyl acetate (50 mL). The organic layers were dried over sodium sulfate, the solvent was evaporated, and the residue analyzed by NMR. Incomplete N-methylation mandated the reductive amination step to be repeated three times (using formaldehyde solution, 7.4 mL, 100 mmol, and sodium cyanoborohydride, 2.07 g, 33 mmol) before complete conversion was attained. After this, the crude product was purified on a FlashMaster system (silica, eluted with heptane/ethyl acetate mixtures) to yield the title compound as a yellow oil (1.85 g, 62%).

$^1$H NMR (CDCl$_3$): 2.64 (s, 3H), 3.11 (s, 3H), 4.66 (s, 3H), 6.52 (d, 1H), 6.60 (dd, 1H), 6.69 (d, 1H), 6.77 (d, 1H), 8.10 (d, 1H).

N(4)-(5-Chloro-thiophen-2-ylmethyl)-2,N(4)-dimethyl-benzene-1,4-diamine

To a suspension of (5-chloro-thiophen-2-ylmethyl)-(methyl)-(3-methyl-4-nitrophenyl)-amine (1.85 g, 6.23 mmol) and iron powder (2.09 g, 37.4 mmol) in ethanol (60 mL) was added 6 N HCl (12.5 mL, 75 mmol), and the mixture was stirred vigorously at +60° C. for 50 minutes. It was then poured into saturated aqueous sodium bicarbonate (200 mL) to which enough sodium carbonate was added to attain a pH>10. The resulting mixture was extracted with ethyl acetate (200 mL, then 2×100 mL), the extract was dried over sodium sulfate and volatiles were evaporated. The residue was purified on a FlashMaster system (silica, eluted with heptane/ethyl acetate mixtures) to yield the title compound as a brown oil (1.51 g, 91%).

$^1$H NMR (CDCl$_3$): 2.16 (s, 3H), 2.79 (s, 3H), 3.32 (br. s, 2H), 4.39 (s, 3H), 6.58-6.65 (m, 4H), 6.72 (d, 1H).

Synthesis of Intermediates of the General Formulas XXXV, XXXVI, and XIX from XXXIV:

(3-Methyl-4-nitrophenyl)-(4-trifluoromethylbenzyl)-amine

A suspension of 4-trifluoromethylbenzaldehyde (819 µL, 6.00 mmol), 3-methyl-4-nitroaniline (609 mg, 4.00 mmol), and Amberlite IRC-84 (200 mg, H$^+$ form) in o-xylene (4 mL) was heated under nitrogen at 140° C. for 6 hours. It was then cooled to room temperature, diluted with ethyl acetate (5 mL), dried over sodium sulfate, filtered, and volatiles were evaporated. The residue was dissolved in acetonitrile (20 mL) and sodium cyanoborohydride (503 mg, 8.00 mmol) was added in one portion, followed by acetic acid (1 mL) in several portions over 15 minutes. After a further 30 minutes solvents were evaporated and the residue was partitioned between ethyl acetate (50 mL), brine (25 mL), and 10% aqueous potassium carbonate (25 mL). The organic layer was dried over sodium sulfate, solvents were evaporated, and the residue was purified on a FlashMaster system (silica, eluted with heptane/ethyl acetate mixtures) to yield the title compound as a yellow powder (1.02 g, 82%).

¹H NMR (CDCl₃): 2.59 (s, 3H), 4.50 (d, 2H), 4.76 (br. t, 1H), 6.40 (d, 1H), 6.43 (dd, 1H), 7.45 (d, 2H), 7.63 (d, 2H), 8.05 (d, 1H).

(3-Methyl-4-nitrophenyl)-(4-trifluoromethylbenzyl)-carbamic acid tert-butyl ester A solution of (3-methyl-4-nitrophenyl)-(4-trifluoromethylbenzyl)-amine (1.02 g, 3.29 mmol), di-tert-butyl dicarbonate (1.08 g, 4.93 mmol), dimethylaminopyridine (201 mg, 1.64 mmol), and triethylamine (687 µL, 4.93 mmol) in acetonitrile (20 mL) was stirred at room temperature for 18 hours in an open flask (to allow carbon dioxide to escape). Volatiles were evaporated and the residue was dissolved in ethyl acetate (50 mL). This solution was washed with sat. ammonium chloride (2×50 mL), dried over sodium sulfate, volatiles were evaporated, and the residue was purified on a FlashMaster system (silica, eluted with heptane/ethyl acetate mixtures) to yield the title compound as a pale yellow, viscous oil (1.17 g, 86%), which retained traces of heptane.

¹H NMR (CDCl₃): 1.44 (s, 9H), 2.58 (s, 3H), 4.95 (s, 2H), 7.16 (dd, 1H), 7.21 (d, 1H), 7.34 (d, 2H), 7.60 (d, 2H), 7.96 (d, 1H).

(4-Amino-3-methylphenyl)-(4-trifluoromethylbenzyl)-carbamic acid tert-butyl ester A solution of Na₂S₂O₄ (3.00 g, 17.2 mmol) in water (20 mL) was added to a solution of (3-methyl-4-nitrophenyl)-(4-trifluoromethylbenzyl)-carbamic acid tert-butyl ester (1.41 g, 3.44 mmol) in tetrahydrofuran (20 mL), and the resulting mixture was stirred for 20 hours at +55° C. After cooling to room temperature, the water phase was saturated with potassium carbonate, the organic layer was separated, and the aqueous layer was extracted with ethyl acetate (2×20 mL). The combined organic layers were dried over sodium sulfate, solvents were evaporated, and the residue was purified on a FlashMaster system (silica, eluted with heptane/ethyl acetate mixtures) to yield the title compound as a white solid (1.09 g, 83%).

¹H NMR (CDCl₃): 1.41 (s, 9H), 2.10 (s, 3H), 3.59 (br. s, 2H), 4.78 (s, 2H), 6.56 (d, 1H), 6.76 (br. s, 2H), 7.36 (d, 2H), 7.55 (d, 2H).

Compounds of the Invention

Example 1

1a {4-[(Benzofuran-2-ylmethyl)-amino]-2-methylphenyl}-carbamic acid propyl ester A mixture of 0.1 M solution of (4-amino-2-methylphenyl)-carbamic acid propyl ester (0.35 mL, 0.035 mmol) and 0.1 M solution of benzofuran-2-carbaldehyde (0.35 mL) in tetrahydrofuran (THF) was kept at 55° C. for 60 minutes. Volatiles were removed in vacuo. To the obtained residue 0.2 M sodium cyanoborohydride (NaBH₃CN) (0.5 mL) in methanol and acetic acid (0.03 mL) were added. After sonication for 60 minutes the reaction mixture was evaporated in vacuo and the title compound was separated by preparative LC/MS to give 5.1 mg of colorless solid. Yield 43%. LC/MS (m/z) 339.2 ([M+H]⁺); RT=2.92, (UV, ELSD) 94%, 94%.

1b {4-[(5-Chloro-thiophen-2-ylmethyl)-amino]-2-methylphenyl}-carbamic acid ethyl ester LC/MS (m/z) 323.9 (M⁺); RT=2.67, (UV, ELSD) 94%, 100%.

1c {4-[(Benzo[b]thiophen-2-ylmethyl)-amino]-2-methylphenyl}-carbamic acid ethyl ester LC/MS (m/z) 340.0 (M⁺); RT=2.87, (UV, ELSD) 91%, 100%.

1d {2-Methyl-4-[(5-phenyl-thiophen-2-ylmethyl)-amino]-phenyl}-carbamic acid ethyl ester LC/MS (m/z) 365.3 ([M–H]⁺); RT=2.89, (UV, ELSD) 97%, 99%.

1e [4-(4-Isopropyl-benzylamino)-2-methylphenyl]-carbamic acid ethyl ester

LC/MS (m/z) 326.0 (M⁺); RT=2.50, (UV, ELSD) 84%, 98%.

1f
[4-(4-Fluoro-benzylamino)-2-methylphenyl]-carbamic acid propyl ester

LC/MS (m/z) 317.1 ([M+H]⁺); RT=2.32, (UV, ELSD) 82%, 96%.

1g (4-{[4-(4-Chloro-benzenesulfonyl)-3-methyl-thiophen-2-ylmethyl]-amino}-2-methylphenyl)-carbamic acid propyl ester LC/MS (m/z) 493.0 ([M+H]⁺); RT=3.18, (UV, ELSD) 91%, 97%.

1h {4-[(5-Methyl-thiophen-2-ylmethyl)-amino]-2-methylphenyl}-carbamic acid propyl ester LC/MS (m/z) 317.1 ([M–H]⁺); RT=2.41, (UV, ELSD) 76%, 93%.

1i {4-[(5-Bromo-thiophen-2-ylmethyl)-amino]-2-methylphenyl}-carbamic acid propyl ester LC/MS (m/z) 382.0 (M⁺); RT=2.96, (UV, ELSD) 70%, 87%.

1j {4-[(5-Chloro-thiophen-2-ylmethyl)-amino]-2-methylphenyl}-carbamic acid propyl ester LC/MS (m/z) 338.2 (M⁺); RT=2.92, (UV, ELSD) 85%, 84%.

1k {4-[(Benzo[b]thiophen-2-ylmethyl)-amino]-2-methylphenyl}-carbamic acid propyl ester LC/MS (m/z) 355.1 ([M+H]⁺); RT=3.08, (UV, ELSD) 93%, 97%.

1l {2-Methyl-4-[(5-phenyl-thiophen-2-ylmethyl)-amino]-phenyl}-carbamic acid propyl ester LC/MS (m/z) 379.3 ([M–H]⁺); RT=3.08, (UV, ELSD) 91%, 95%.

1m [4-(4-Isopropyl-benzylamino)-2-methylphenyl]-carbamic acid propyl ester

LC/MS (m/z) 341.2 ([M+H]⁺); RT=2.71, (UV, ELSD) 73%, 96%.

1o {4-[(5-Bromo-thiophen-2-ylmethyl)-amino]-2-chlorophenyl}-carbamic acid ethyl ester LC/MS (m/z) 389.0 ([M+H]$^+$); RT=3.24, (UV, ELSD) 98%, 99%.

1p {4-[(5-Chloro-thiophen-2-ylmethyl)-amino]-2-chlorophenyl}-carbamic acid ethyl ester LC/MS (m/z) 345.0 ([M+H]$^+$); RT=3.21, (UV, ELSD) 99%, 100%.

1q {4-[(Benzo[b]thiophen-2-ylmethyl)-amino]-2-chlorophenyl}-carbamic acid ethyl ester LC/MS (m/z) 361.0 ([M+H]$^+$); RT=3.28, (UV, ELSD) 95%, 100%.

1r [2-Chloro-4-(4-isopropyl-benzylamino)-phenyl]-carbamic acid ethyl ester

LC/MS (m/z) 346.0 (M$^+$); RT=3.48, (UV, ELSD) 95%, 100%.

1s [2-Chloro-4-(4-fluoro-benzylamino)-phenyl]-carbamic acid propyl ester

LC/MS (m/z) 337.1 ([M+H]$^+$); RT=3.20, (UV, ELSD) 97%, 99%.

1t 2-Chloro-4-{[4-(4-chloro-benzenesulfonyl)-3-methyl-thiophen-2-ylmethyl]-amino}-phenyl)-carbamic acid propyl ester LC/MS (m/z) 514.2 ([M+H]$^+$); RT=3.52, (UV, ELSD) 94%, 99%.

1u {4-[(5-Methyl-thiophen-2-ylmethyl)-amino]-2-chlorophenyl}-carbamic acid propyl ester LC/MS (m/z) 337.0 ([M−1]$^+$); RT=3.27, (UV, ELSD) 94%, 100%.

1v {4-[(5-Bromo-thiophen-2-ylmethyl)-amino]-2-chlorophenyl}-carbamic acid propyl ester LC/MS (m/z) 403.9 ([M+H]$^+$); RT=3.45, (UV, ELSD) 99%, 99%.

1w {2-Chloro-4-[(5-chloro-thiophen-2-ylmethyl)-amino]-phenyl}-carbamic acid propyl ester LC/MS (m/z) 356.9 ([M−H]$^+$); RT=3.43, (UV, ELSD) 98%, 95%.

1x {4-[(Benzo[b]thiophen-2-ylmethyl)-amino]-2-chlorophenyl}-carbamic acid propyl ester LC/MS (m/z) 372.9 ([M−H]$^+$); RT=3.49, (UV, ELSD) 93%, 99%.

1y {4-[(Benzofuran-2-ylmethyl)-amino]-2-chlorophenyl}-carbamic acid propyl ester LC/MS (m/z) 357.1 ([M−H]$^+$); RT=3.37, (UV, ELSD) 95%, 98%.

1z {4-[(5-Chloro-thiophen-2-ylmethyl)-amino]-2-cyanophenyl}-carbamic acid ethyl ester LC/MS (m/z) 335.0 (M$^+$); RT=2.91, (UV, ELSD) 99%, 100%.

1aa {4-[(Benzo[b]thiophen-2-ylmethyl)-amino]-2-methoxyphenyl}-carbamic acid methyl ester LC/MS (m/z) 341.1 (M$^+$); RT=2.62, (UV, ELSD) 96%, 100%.

1ab {4-[(5-Bromo-thiophen-2-ylmethyl)-amino]-2-methoxyphenyl}-carbamic acid isopropyl ester LC/MS (m/z) 400.0 (M$^+$); RT=2.93, (UV, ELSD) 96%, 100%.

1ac {4-[(5-Bromo-thiophen-2-ylmethyl)-amino]-phenyl}-carbamic acid propyl ester

LC/MS (m/z) 367.9 (M$^+$); RT=2.66, (UV, ELSD) 87.0%, 95.0%.

1ad {4-[(5-Chloro-thiophen-2-ylmethyl)-amino]-phenyl}-carbamic acid propyl ester LC/MS (m/z) 324.0 (M$^+$); RT=2.60, (UV, ELSD) 88.2%, 96.5%.

1ae [2-Cyano-4-(4-isopropylbenzylamino)-phenyl]-carbamic acid ethyl ester

LC/MS (m/z) 337.0 (M$^+$); RT=3.25, (UV, ELSD) 90.8%, 99.6%.

1af [2-Iodo-4-(4-isopropyl-benzylamino)-phenyl]-carbamic acid propyl ester

LC/MS (m/z) 452.0 (M$^+$); RT=3.72, (UV, ELSD) 88.0%, 97.7%.

1ag [4-(4-tert-Butyl-benzylamino)-2-iodophenyl]-carbamic acid propyl ester

LC/MS (m/z) 465.9 ([M−1]$^+$); RT=3.85, (UV, ELSD) 86.6%, 96.6%.

1ah [2-Iodo-4-(4-trifluoromethyl-benzylamino)-phenyl]-carbamic acid propyl ester LC/MS (m/z) 479.0 ([M+H]$^+$); RT=3.54, (UV, ELSD) 97.7%, 99.8%.

1ai [2-Iodo-4-(4-methylsulfanyl-benzylamino)-phenyl]-carbamic acid propyl ester

LC/MS (m/z) 454.8 ([M−1]$^+$); RT=3.38, (UV, ELSD) 98.0%, 99.8%.

1aj {2-Iodo-4-[4-(4-methylpiperazin-1-yl)-benzylamino]-phenyl}-carbamic acid propyl ester LC/MS (m/z) 508.9 ([M+H]$^+$); RT=1.90, (UV, ELSD) 62.0%, 79.2%.

1ak {4-[(5-Bromo-thiophen-2-ylmethyl)-amino]-2-trifluoromethyl-phenyl}-carbamic acid ethyl ester LC/MS (m/z) 421.9 (M+); RT=3.27, (UV, ELSD) 98.7%, 98.5%.

1al {4-[(5-Chloro-thiophen-2-ylmethyl)-amino]-2-trifluoromethyl-phenyl}-carbamic acid ethyl ester LC/MS (m/z) 378.0 (M+); RT=3.25, (UV, ELSD) 97.7%, 99.5%.

1am [4-(4-tert-Butyl-benzylamino)-2-trifluoromethyl-phenyl]-carbamic acid ethyl ester LC/MS (m/z) 394.2 (M+); RT=3.70, (UV, ELSD) 90.2%, 97.9%.

1an [4-(4-Methylsulfanyl-benzylamino)-2-trifluoromethyl-phenyl]-carbamic acid ethyl ester LC/MS (m/z) 384.1 (M+); RT=3.22, (UV, ELSD) 84.4%, 94.6%.

1ao {4-[(5-Bromo-thiophen-2-ylmethyl)-amino]-2-trifluoromethyl-phenyl}-carbamic acid propyl ester LC/MS (m/z) 438.1 ([M+H]+); RT=3.47, (UV, ELSD) 98.9%, 99.9%.

1ap [4-(4-Isopropylbenzylamino)-2-trifluoromethyl-phenyl]-carbamic acid propyl ester LC/MS (m/z) 393.3 ([M−1]+); RT=3.60, (UV, ELSD) 71.3%, 74.1%.

1aq [4-(4-tert-Butyl-benzylamino)-2-trifluoromethyl-phenyl]-carbamic acid propyl ester LC/MS (m/z) 408.3 (M+); RT=3.89, (UV, ELSD) 91.1%, 98.6%.

1ar [2-Trifluoromethyl-4-(4-trifluoromethyl-benzylamino)-phenyl]-carbamic acid propyl ester LC/MS (m/z) 421.1 ([M+H]+); RT=3.52, (UV, ELSD) 99.2%, 99.8%.

1as [4-(4-Dimethylamino-benzylamino)-2-trifluoromethyl-phenyl]-carbamic acid propyl ester LC/MS (m/z) 394.3 ([M−1]+); RT=2.02, (UV, ELSD) 63.4%, 100.0%.

1at [4-(4-Methylsulfanyl-benzylamino)-2-trifluoromethyl-phenyl]-carbamic acid propyl ester LC/MS (m/z) 398.1 (M+); RT=3.40, (UV, ELSD) 92.5%, 98.1%.

1au {4-[(5-Bromo-thiophen-2-ylmethyl)-amino]-2-cyanophenyl}-carbamic acid propyl ester LC/MS (m/z) 394.0 ([M+H]+); RT 3.15, UV, ELSD) 97.5%, 89.8%.

1av {4-[(5-Chloro-thiophen-2-ylmethyl)-amino]-2-cyanophenyl}-carbamic acid propyl ester LC/MS (m/z) 348.9 (M+); RT=3.11, (UV, ELSD) 99.7%, 96.3%.

1aw [2-Cyano-4-(4-trifluoromethyl-benzylamino)-phenyl]-carbamic acid propyl ester LC/MS (m/z) 378.3 ([M+H]+); RT=3.25, (UV, ELSD) 99.6%, 99.7%.

1ax {2-Bromo-4[(5-bromo-thiophen-2-ylmethyl)-amino]-phenyl}-carbamic acid propyl ester LC/MS (m/z) 447.9 ([M+H]+); RT=3.48, (UV, ELSD) 99.3%, 99.3%.

1ay {2-Bromo-4-[(5-chloro-thiophen-2-ylmethyl)-amino]-phenyl}-carbamic acid propyl ester LC/MS (m/z) 402.9 ([M+H]+); RT=3.47, (UV, ELSD) 95.7%, 99.6%.

1az [2-Bromo-4-(4-isopropylbenzylamino)-phenyl]-carbamic acid propyl ester

LC/MS (m/z) 406.1 ([M+H]+); RT=3.72, (UV, ELSD) 80.2%, 93.9%.

1ba [2-Bromo-4-(4-tert-butyl-benzylamino)-phenyl]-carbamic acid propyl ester

LC/MS (m/z) 418.2 (M+); RT=3.86, (UV, ELSD) 87.2%, 96.8%.

1bb [2-Bromo-4-(4-trifluoromethyl-benzylamino)-phenyl]-carbamic acid propyl ester LC/MS (m/z) 431.0 ([M+H]+); RT 3.55, (UV, ELSD) 95.9%, 99.8%.

1bc [2-Bromo-4-(4-methylsulfanyl-benzylamino)-phenyl]-carbamic acid propyl ester LC/MS (m/z) 409.0 ([M+H]+); RT=3.36, (UV, ELSD) 98.4%, 99.7%.

1bd N-{4-[(5-Bromo-thiophen-2-ylmethyl)-amino]-2-methoxyphenyl}-butyramide

LC/MS (m/z) 382.0+; RT=2.66, (UV, ELSD) 95.9%, 99.3%.

1be N-{4-[(5-Chloro-thiophen-2-ylmethyl)-amino]-2-methoxyphenyl}-butyramide

LC/MS (m/z) 339.2 ([M+H]+); RT=2.61, (UV, ELSD) 96.4%, 98.4%.

1bf N-[4-(4-Isopropylbenzylamino)-2-methoxyphenyl]-butyramide

LC/MS (m/z) 341.1 ([M+H]+); RT=2.49, (UV, ELSD) 91.1%, 100.0%.

1bg N-[4-(4-tert-Butyl-benzylamino)-2-methoxyphenyl]-butyramide

LC/MS (m/z) 355.2 ([M+H]$^+$); RT=2.65, (UV, ELSD) 97.0%, 100.0%.

1bh N-[2-Methoxy-4-(4-trifluoromethyl-benzylamino)-phenyl]-butyramide

LC/MS (m/z) 367.2 ([M+H]$^+$); RT=2.79, (UV, ELSD) 93.9%, 96.6%.

1bi {4-[(5-Chloro-thiophen-2-ylmethyl)-amino]-2-furan-2-yl-phenyl}-carbamic acid propyl ester LC/MS (m/z) 390.1 (M$^+$); RT=3.38, (UV, ELSD) 92.9%, 99.8%.

1bj [2-Furan-2-yl-4-(4-isopropylbenzylamino)-phenyl]-carbamic acid propyl ester LC/MS (m/z) 393.2 ([M+H]$^+$); RT=3.41, (UV, ELSD) 89.9%, 100.0%.

1bk [5-(4-Fluorobenzylamino)-biphenyl-2-yl]-carbamic acid propyl ester

LC/MS (m/z) 379.3 ([M+H]$^+$); RT=3.06, UV, ELSD) 83.7%, 99.7%.

1bl {5-[(5-Chloro-thiophen-2-ylmethyl)-amino]-biphenyl-2-yl}-carbamic acid propyl ester LC/MS (m/z) 400.0 (M$^+$); RT=3.48, (UV, ELSD) 89.8%, 98.7%.

1bm [5-(4-Isopropylbenzylamino)-biphenyl-2-yl]-carbamic acid propyl ester

LC/MS (m/z) 403.2 ([M+H]$^+$); RT=3.37, (UV, ELSD) 73.8%, 98.7%.

1zz N-{2-Chloro-4-[(5-chloro-thiophen-2-ylmethyl)-amino]-phenyl}-2,2,2-trifluoroacetamide Data for this compound are reported above in the synthesis of intermediates of the general formulas XII-XXIII

Example 2

2a {4-[(4-Fluoro-benzyl)-(methyl)amino]-2-methoxyphenyl}-carbamic acid propyl ester A mixture of (4-Amino-2-methoxyphenyl)-carbamic acid propyl ester (0.3 mL, 0.1 M solution in tetrahydrofuran (THF)) and 4-fluorobenzaldehyde (0.3 mL, 0.1 M solution in tetrahydrofuran (THF)) was heated to 50° C. for 60 minutes and evaporated in vacuo. To the obtained residue, sodium cyanoborohydride (NaBH$_3$CN) (0.6 mL, 0.2 M solution in methanol) and acetic acid (0.03 mL) were added. The reaction mixture was kept at room temperature for 30 minutes, then formaldehyde (0.03 mL, 37% in water) and acetic acid (0.03 mL) were added. After 30 minutes the reaction mixture was evaporated in vacuo. The title compound was separated by preparative LC/MS to give 4.3 mg of colorless solid, yield 41%. $^1$H NMR (1:4 DMSO-H$_6$/DMSO-D$_6$): 8.04 (br. s, NH), 7.25 (m, 2H), 7.13 (m, 3H), 6.36 (s, 1H), 6.24 (d, 1H), 4.53 (s, 2H, CH$_2$), 3.93 (t, 2H), 3.70 (s, 3H, OMe), 2.97 (s, NMe), 1.57 (m, 2H), 0.89 (t, 3H). LC/MS (m/z) 347.2 ([M+H]$^+$); RT=2.32, (UV, ELSD) 96%, 100%.

The following compounds were prepared analogously from appropriate anilines and aldehydes:

2b [4-(Benzo[b]thiophen-2-ylmethyl-(methyl)amino)-2-methoxy-phenyl]-carbamic acid propyl ester $^1$H NMR (1:4 DMSO-H$_6$/DMSO-D$_6$): 8.07 (br. s, NH), 7.86 (d, 1H), 7.76 (d, 1H), 7.30 (m, 4H), 6.49 (s, 1H), 6.36 (d, 1H), 4.83 (s, 2H, CH$_2$), 3.94 (t, 2H), 3.75 (s, 3H, OMe), 2.98 (s, NMe), 1.58 (m, 2H), 0.89 (t, 3H).). LC/MS (m/z) 385.0 ([M+H]$^+$); RT=3.25, (UV, ELSD) 99%, 100%.

2c {4-[(5-Chloro-thiophen-2-ylmethyl)-(methyl)amino]-2-methoxy-phenyl}-carbamic acid propyl ester LC/MS (m/z) 367.9 (M$^+$); RT=3.07, (UV, ELSD) 99%, 100%.

2d {4-[(5-Bromo-thiophen-2-ylmethyl)-(methyl)amino]-2-methoxy-phenyl}-carbamic acid propyl ester LC/MS (m/z) 412.1 (M$^+$); RT=3.12, (UV, ELSD) 99%, 100%.

2e {2-Methoxy-4-[methyl-(5-methyl-thiophen-2-ylmethyl)-amino]-phenyl}-carbamic acid propyl ester LC/MS (m/z) 348.0 (M$^+$); RT=2.46, (UV, ELSD) 95%, 100%.

2f {4-[(5-Bromo-thiophen-2-ylmethyl)-(methyl)amino]-2-methylphenyl}-carbamic acid propyl ester LC/MS (m/z) 398.0 ([M+2]$^+$); RT=3.10, (UV, ELSD) 97.0%, 98.1%.

2g {4-[(4-Isopropylbenzyl)-(methyl)amino]-2-methylphenyl}-carbamic acid propyl ester LC/MS (m/z) 355.2 ([M+H]$^+$); RT=2.70, (UV, ELSD) 85.4%, 99.5%.

2h {2-Methyl-4-[methyl-(4-trifluoromethyl-benzyl)-amino]-phenyl}-carbamic acid propyl ester LC/MS (m/z) 380.3 (M$^+$); RT=3.18, (UV, ELSD) 95.2%, 98.5%.

2i {2-Methyl-4-[methyl-(4-methylsulfanyl-benzyl)-amino]-phenyl}-carbamic acid propyl ester LC/MS (m/z) 358.0 (M$^+$); RT=2.42, (UV, ELSD) 97.9%, 99.0%.

2j {4-[(4-tert-Butyl-benzyl)-(methyl)amino]-2-chlorophenyl}-carbamic acid ethyl ester LC/MS (m/z) 374.9 ([M+H]$^+$); RT=3.92, (UV, ELSD) 97.8%, 100.0%.

2k {2-Chloro-4-[methyl-(4-trifluoromethyl-benzyl)-amino]-phenyl}-carbamic acid ethyl ester LC/MS (m/z) 387.3 ([M+H]$^+$); RT=3.59, (UV, ELSD) 99.9%, 100.0%.

2l {2-Chloro-4-[methyl-(4-methylsulfanyl-benzyl)-amino]-phenyl}-carbamic acid ethyl ester LC/MS (m/z) 363.1 ([M−1]$^+$); RT=3.36, (UV, ELSD) 92.1%, 99.6%.

2m {4-[(5-Bromo-thiophen-2-ylmethyl)-(methyl)amino]-2-chlorophenyl}-carbamic acid propyl ester LC/MS (m/z) 418.1 ([M+H]$^+$); RT=3.80, (UV, ELSD) 99.3%, 100.0%.

2n {2-Chloro-4-[(5-chloro-thiophen-2-ylmethyl)-(methyl)amino]-phenyl}-carbamic acid propyl ester LC/MS (m/z) 374.0 ([M+H]$^+$); RT=3.77, (UV, ELSD) 99.6%, 99.9%.

2o {4-[(4-tert-Butyl-benzyl)-(methyl)amino]-2-chlorophenyl}-carbamic acid propyl ester LC/MS (m/z) 389.2 ([M+H]$^+$); RT=4.09, (UV, ELSD) 99.6%, 99.9%.

2p {2-Chloro-4-[methyl-(4-trifluoroethyl-benzyl)-amino]-phenyl}-carbamic acid propyl ester LC/MS (m/z) 401.1 ([M+H]$^+$); RT=3.81, (UV, ELSD) 99.8%, 100.0%.

2q {4-[(5-Bromo-thiophene-2-ylmethyl)-(methyl)amino]-2-trifluoromethyl-phenyl}-carbamic acid ethyl ester LC/MS (m/z) 435.9 ([M−1]$^+$); RT=3.56, (UV, ELSD) 99.4%, 100.0%.

2r {4-[(5-Chloro-thiophen-2-ylmethyl)-(methyl)amino]-2-trifluoromethyl-phenyl}-carbamic acid ethyl ester LC/MS (m/z) 392.3 (M$^+$); RT=3.56, (UV, ELSD) 99.0%, 100.0%.

2s {4-[(4-Isopropyl-benzyl)-(methyl)amino]-2-trifluoromethyl-phenyl}-carbamic acid ethyl ester LC/MS (m/z) 395.3 ([M+H]$^+$); RT=3.85, (UV, ELSD) 99.0%, 100.0%.

2t {4-[(4-tert-Butyl-benzyl)-(ethyl)amino]-2-trifluoromethyl-phenyl}-carbamic acid ethyl ester LC/MS (m/z) 409.2 ([M+H]$^+$); RT=3.98, (UV, ELSD) 97.9%, 99.8%.

2u {4-[Methyl-(4-trifluoromethyl-benzyl)-amino]-2-trifluoromethyl-phenyl}-carbamic acid ethyl ester LC/MS (m/z) 421.2 ([M+H]$^+$); RT=3.59, (UV, ELSD) 92.9%, 98.5%.

2v {4-[Methyl-(4-methylsulfanyl-benzyl)-amino]-2-trifluoromethyl-phenyl}-carbamic acid ethyl ester LC/MS (m/z) 397.0 ([M−1]$^+$); RT=3.48, (UV, ELSD) 99.4%, 99.9%.

2w {4-[(5-Bromo-thiophen-2-ylmethyl)-methyl-amino]-2-trifluoromethyl-phenyl}-carbamic acid propyl ester LC/MS (m/z) 449.9 ([M−1]$^+$); RT=3.76, (UV, ELSD) 99.5%, 100.0%.

2x {4-[(5-Chloro-thiophen-2-ylmethyl)-(methyl)amino]-2-trifluoromethyl-phenyl}-carbamic acid propyl ester LC/MS (m/z) 405.9 (M$^+$); RT=3.73, (UV, ELSD) 98.4%, 100.0%.

2y {4-[(4-Isopropyl-benzyl)-(methyl)amino]-2-trifluoromethyl-phenyl}-carbamic acid propyl ester LC/MS (m/z) 409.2 ([M+H]$^+$); RT=4.04, (UV, ELSD) 99.3%, 99.9%.

2z {4[(4-tert-Butyl-benzyl)-methyl)amino]-2-trifluoromethyl-phenyl}-carbamic acid propyl ester LC/MS (m/z) 423.1 ([M+H]$^+$); RT=4.29, (UV, ELSD) 98.9%, 99.7%.

2aa {4-[Methyl-(4-trifluoromethyl-benzyl)-amino]-2-trifluoromethyl-phenyl}-carbamic acid propyl ester LC/MS (m/z) 435.3 ([M+H]$^+$); RT=3.77, (UV, ELSD) 99.7%, 99.9%.

2ab {4-[Methyl-(4-methylsulfanyl-benzyl)-amino]-2-trifluoromethyl-phenyl}-carbamic acid propyl ester LC/MS (m/z) 412.0 (M$^+$); RT=3.67, (UV, ELSD) 99.3%, 99.8%.

2ac {4-[(5-Bromo-thiophen-2-ylmethyl)-(methyl)amino]-2-cyanophenyl}-carbamic acid propyl ester LC/MS (m/z) 407.0 (M$^+$); RT=3.39, (UV, ELSD) 97.7%, 99.6%.

2ad {4-[(4-tert-Butyl-benzyl)-(methyl)amino]-2-cyanophenyl}-carbamic acid propyl ester LC/MS (m/z) 380.3 ([M+H]$^+$); RT=3.83, (UV, ELSD) 99.4%, 99.9%.

2ae {2-Cyano-4-[methyl-(4-trifluoromethyl-benzyl)-amino]-phenyl}-carbamic acid propyl ester LC/MS (m/z) 392.3 ([M+H]$^+$); RT=3.44, (UV, ELSD) 98.9%, 99.9%.

2af {2-Bromo-4-[(5-bromo-thiophen-2-ylmethyl)-(methyl)amino]-phenyl}-carbamic acid propyl ester LC/MS (m/z) 462.1 ([M+H]$^+$); RT=3.84, (UV, ELSD) 98.2%, 99.9%.

2ag {2-Bromo-4-[(5-chloro-thiophen-2-ylmethyl)-(methyl)amino]-phenyl}-carbamic acid propyl ester LC/MS (m/z) 418.1 ([M+H]$^+$); RT=3.83, (UV, ELSD) 99.3%, 100.0%.

2ah {2-Bromo-4-[(4-isopropylbenzyl)-(methyl)amino]-phenyl}-carbamic acid propyl ester LC/MS (m/z) 420.2 ([M+H]$^+$); RT=4.04, (UV, ELSD) 98.8%, 99.7%.

2ai {2-Bromo-4-[(4-tert-butyl-benzyl)-(methyl)amino]-phenyl}-carbamic acid propyl ester LC/MS (m/z) 432.1 (M$^+$); RT=4.15, (UV, ELSD) 99.3%, 100.0%.

2aj {2-Bromo-4-[methyl-(4-trifluoromethyl-benzyl)-amino]-phenyl}-carbamic acid propyl ester LC/MS (m/z) 447.0 ([M+H]$^+$); RT=3.84, (UV, ELSD) 98.4%, 99.9%.

2zz N-{2-Chloro-4-[(5-chloro-thiophen-2-ylmethyl)-(methyl)amino]-phenyl}-2,2,2-trifluoroacetamide Data for this compound are reported above in the synthesis of intermediates of the general formula XIII-XXIII Example 3

3a {4-[(4-Fluorobenzyl)-(methyl)-amino]-2-isopropoxyphenyl}-carbamic acid ethyl ester 4-(4-Fluorobenzyl)-(methyl)-amino-2-isopropoxyaniline (0.29 g) was dissolved in dry dioxane (3 mL). N,N-Diisopropylethylamine (0.27 mL) and ethyl chloroformate (0.15 mL) were added, and the reaction mixture was stirred at room temperature over night. Water (5 mL) was added, and the resulting mixture was extracted with ethyl acetate (3×10 mL). The organic phase was dried over sodium sulfate and filtered. The solvent was evaporated in vacuo, and the crude product was purified by flash chromatography (silica gel, heptane/ethyl acetate 19:1, 1% triethylamine, gradient). Evaporation of the solvent in vacuo furnished the title compound (0.20 g, 55%) as a colourless oil. LC-MS (m/z) 361.3 ([M+H]$^+$); RT=2.58, (UV, ELSD) 90%, 98%.

Example 4

4a [4-(3-Fluorobenzylamino)-2-methoxyphenyl]-carbamic acid ethyl ester

A solution of 3-fluorobenzaldehyde in dry methanol (84 μL, 476 mM) was added to a solution of (4-Amino-2-methyloxyphenyl)-carbamic acid ethyl ester (84 μL, 0.476 M in dry methanol). The resulting mixture was heated to 40° C. for 30 minutes. The solvent was evaporated in vacuo, and the remaining material was dissolved in 1,2-dichloroethane (1 mL). Sodium triacetoxyborohydrate (20 mg) was added, and the resulting mixture was kept at room temperature for 2 hours, under 2 periods of sonication for 10 minutes, respectively. The reaction mixture was filtered through silica gel (500 mg), and the column was washed with 1,2-dichloroethane (3 mL). The solvent was evaporated in vacuo yielding the title compound (5.7 mg, 45%).

LC-MS (m/z) 318.1 (M$^+$); RT=2.33, (UV, ELSD) 93%, 100%.

The following compounds were prepared in an analogous fashion:

4b [4-(4-Isopropylbenzylamino)-2-methoxyphenyl]-carbamic acid ethyl ester

LC-MS (m/z) 341.3 (M$^+$); RT=2.51, (UV, ELSD) 86%, 100%.

4c {2-Methoxy-4-[(3-methylthiophen-2-ylmethyl)-amino]-phenyl}-carbamic acid ethyl ester LC-MS (m/z) 319.9 (M$^+$); RT=2.10, (UV, ELSD) 79%, 99%.

4d [4-(2,4-Difluorobenzylamino)-2-methoxyphenyl]-carbamic acid ethyl ester

LC-MS (m/z) 337.2 ([M+H]$^+$); RT=2.44, (UV, ELSD) 93%, 100%.

Example 5

5a [2-Cyclopentyloxy-4-(4-methoxybenzylamino)-phenyl]-carbamic acid ethyl ester (2-Cyclopentyloxy-4-nitrophenyl)-carbamic acid ethyl (294 mg) was dissolved in ethanol (26 mL). Zinc granules (1.63 g) and aqueous hydrochloric acid (5.0 mL, 2 M) were added. The resulting mixture was sonicated at room temperature for 6.5 hours, and then kept standing at room temperature over night. Aqueous saturated sodium bicarbonate (100 mL) was added, and the mixture was extracted with ethyl acetate (2×100 mL). The organic phase was washed with water (100 mL) and brine (100 mL), dried over magnesium sulfate, and evaporated in vacuo. The resulting oil was dissolved in methanol (1.82 mL), and an aliquot (40 μL) of this solution was mixed with a solution of 4-methoxybenzaldehyde (40 μL, 0.466 M in methanol). The resulting mixture was heated to 40° C. for 20 minutes. The solvent was evaporated in vacuo, and the remaining material was dissolved in 1,2-dichloroethane (1 mL). Sodium triacetoxyborohydrate (20 mg) was added, and the resulting mixture was kept at room temperature for 2 hours, under 2 periods of sonication for 10 minutes, respectively. The reaction mixture was filtered through silica gel (500 mg), and the column was washed with 1,2-dichloroethane (3 mL). The solvent was evaporated in vacuo yielding the title compound (6.0 mg, 84% from aldehyde).

LC-MS (m/z) 384.1 (M$^+$); RT=2.40, (UV, ELSD) 76%, 96%.

The following compounds were prepared in an analogous fashion:

5b [2-Cyclopentyloxy-4-(3-fluoro-2-methylbenzylamino)-phenyl]-carbamic acid ethyl ester The product was purified by preparative LC-MS.
LC-MS (m/z) 386.2 (M$^+$); RT=3.22, (UV, ELSD) 80%, 91%.

5c [4-(3-Fluoro-2-methylbenzylamino)-2-phenethyloxyphenyl]-carbamic acid ethyl ester The product was purified by preparative LC-MS.
LC-MS (m/z) 422.3 (M$^+$); RT=3.38, (UV, ELSD) 84%, 91%.

5d [2-Benzyloxy-4-(3-fluoro-2-methylbenzylamino)-phenyl]-carbamic acid ethyl ester The product was purified by preparative LC-MS.
LC-MS (m/z) 409.2 ([M+H]$^+$); RT=3.30, (UV, ELSD) 80%, 89%.

5e [2-Benzyloxy-4-(4-methylsulfanylbenzylamino)-phenyl]-carbamic acid ethyl ester LC-MS (m/z) 422.1 (MN); RT=2.92, (UV, ELSD) 83%, 89%.

5f {4-[(Benzo[b]thiophen-3 ylmethyl)-amino]-2-cyclopentyloxyphenyl}-carbamic acid ethyl ester The product was purified by preparative LC-MS.
LC-MS (m/z) 411.1 ([M+H]$^+$); RT=3.12, (UV, ELSD) 79%, 85%.

5g [4-(3-Fluoro-2-methylbenzylamino)-2-isopropoxyphenyl]-carbamic acid ethyl ester The product was purified by preparative LC-MS.
LC-MS (m/z) 361.2 ([M+H]$^+$); RT=2.95, (UV, ELSD) 77%, 86%.

5h [2-Benzyloxy-4-(3-methoxybenzylamino)-phenyl]-carbamic acid ethyl ester

LC-MS (m/z) 407.3 ([M+H]$^+$) RT=2.81, (UV, ELSD) 76%, 87%.

5i {4-[(Benzo[1,3]dioxol-5-ylmethyl)-amino]-2-isopropoxyphenyl}-carbamic acid ethyl ester LC-MS (m/z) 372.1 (M$^+$); RT=2.24, (UV, ELSD) 76%, 86%.

Example 6

6o N-{2-Chloro-4-[(N-chloro-thiophen-2-ylmethyl)-(methyl)amino]-phenyl}-3-cyclohexylpropionamide Method A: To a mixture of 2-Chloro-N(4)-(5-chloro-thiophen-2-ylmethyl)-N(4)-methyl-benzene-1,4-diamine (14 mg) and triethyl amine (0.04 mL) in acetonitrile (1 mL) 3-cyclohexyl-proionyl chloride (0.03 mL) was added. Volatiles were evaporated in vacuo and the title compound was separated by preparative LC-MS.

Method B: To a stirred mixture of 2-Chloro-N(4)-(5-chloro-thiophen-2-ylmethyl)-N(4)-methyl-benzene-1,4-diamine (470 mg, 1.64 mmol) and sodium bicarbonate in acetonitrile (40 mL) 3-cyclohexyl-proionyl chloride (372 mg, 2.13 mmol) was added. After 1 hour the reaction mixture was quenched with water (100 mL) and ice. The title compound was separated by filtration as a grey-brown solid. Yield 0.422 g, 60%. LC/MS (m/z) 425.4 ([M+H]$^+$); RT=4.09, (UV, ELSD) 97%, 100%. $^1$H NMR (DMSO-d$_6$): 0.87 (m, 2H), 1.05-1.29 (m, 4H), 1.47 (q, 2H), 1.56-1.76 (m, 5H), 2.29 (t, 2H), 2.91 (s, 3H), 4.67 (s, 2H), 6.76 (dd, 1H), 6.83 (d, 1H), 6.88 (d, 1H), 6.96 (d, 1H), 7.27 (d, 1H).

The following compounds were prepared analogously by the method A from corresponding anilines and appropriate acid chlorides, chloroformiates, carbamyl chlorides, isocyanates, or di-tert-butyl dicarbonate (Boc$_2$O). Triethyl amine was used as a base in case of acid chlorides. Pyridine was used as a base in case of chloroformiates and carbamyl chlorides. No base was used in case of isocyanates and Boc$_2$O. In case of (4-amino-3-chlorophenyl)-(5-chloro-thiophen-2-ylmethyl)-carbamic acid tert-butyl ester as an aniline, the residue after evaporation was treated with 2% solution of anisol in a 1:1 mixture of trifluoroacetic acid and methylene chloride for 1 hour and evaporated again before preparative LC-MS:

6a N-{2-Chloro-4-[(5-chloro-thiophen-2-ylmethyl)-(methyl)amino]-phenyl}-2-phenylacetamide LC/MS (m/z) 406.2 ([M+2]$^+$); RT=3.58, (UV, ELSD) 95.5%, 100.0%.

6b N-{2-Chloro-4-[(5-chloro-thiophen-2-ylmethyl)-(methyl)amino]-phenyl}-3,3-dimethylbutyramide LC/MS (m/z) 384.1 (M$^+$); RT=3.72, (UV, ELSD) 98.3%, 100.0%.

6c N-{2-Chloro-4-[(5-chloro-thiophen-2-ylmethyl)-(methyl)amino]-phenyl}-3-phenylpropionamide LC/MS (m/z) 418.1 (M$^+$); RT=3.66, (UV, ELSD) 98.8%, 100.0%.

6d N-{2-Chloro-4-[(5-chloro-thiophen-2-ylmethyl)-(methyl)amino]-phenyl}-butyramide LC/MS (m/z) 356.1 (M$^+$); RT=3.32, (UV, ELSD) 99.4%, 100.0%.

6e Pentanoic acid {2-chloro-4-[(5-chloro-thiophen-2-ylmethyl)-(methyl)amino]-phenyl}-amide LC/MS (m/z) 371.1 ([M+H]$^+$); RT=3.55, (UV, ELSD) 98.3%, 100.0%.

6f Cyclopropanecarboxylic acid {2-chloro-4-[(5-chloro-thiophen-2-ylmethyl)-(methyl)amino]-phenyl}-amide LC/MS (m/z) 355.0 ([M+H]$^+$); RT=3.23, (UV, ELSD) 98.6%, 100.0%.

6g Cyclobutanecarboxylic acid {2-chloro-4-[(5-chloro-thiophen-2-ylmethyl)-(methyl)amino]-phenyl}-amide LC/MS (m/z) 368.1 (M$^+$); RT=3.46, (UV, ELSD) 93.4%, 98.5%.

6h Cyclopentanecarboxylic acid {2-chloro-4-[(5-chloro-thiophen-2-ylmethyl)-(methyl)amino]-phenyl}-amide LC/MS (m/z) 382.0 (M$^+$); RT=3.65, (UV, ELSD) 95.2%, 99.2%.

6i Cyclohexanecarboxylic acid {2-chloro-4-[(5-chloro-thiophen-2-ylmethyl)-(methyl)amino]-phenyl}-amide LC/MS (m/z) 396.1 (M$^+$); RT=3.83, (UV, ELSD) 97.3%, 99.8%.

6j N-{2-Chloro-4[(5-chloro-thiophen-2-ylmethyl)-(methyl)amino]-phenyl}-2 thiophen-2-yl-acetamide LC/MS (m/z) 412.0 ([M+2]$^+$); RT=3.54, (UV, ELSD) 79.3%, 96.4%.

6k N-{2-Chloro-4-[(5-chloro-thiophen-2-ylmethyl)-(methyl)amino]-phenyl}-2-(3-methoxyphenyl)-acetamide LC/MS (m/z) 435.0 ([M+H]$^+$); RT=3.54, (UV, ELSD) 90.9%, 100.0%.

6l N-{2-Chloro-4-[(5-chloro-thiophen-2-ylmethyl)-(methyl)amino]-phenyl}-2-(4-chloro-phenyl)-acetamide LC/MS (m/z) 438.0 (M$^+$); RT=3.78, (UV, ELSD) 98.9%, 100.0%.

6m N-{2-Chloro-4-[(5-chloro-thiophen-2-ylmethyl)-(methyl)amino]-phenyl}-2-(4-methoxy-phenyl)-acetamide LC/MS (m/z) 436.0 ([M+2]$^+$); RT=3.53, (UV, ELSD) 92.0%, 99.4%.

6n N-{2-Chloro-4-[(5-chloro-thiophen-2-ylmethyl)-(methyl)amino]-phenyl}-2-(4-fluoro-phenyl)-acetamide LC/MS (m/z) 421.9 (M$^+$); RT=3.58, (UV, ELSD) 92.2%, 100.0%.

6p N-{2-Chloro-4[(5-chloro-thiophen-2-ylmethyl)-amino]-phenyl}-2,2-dimethylpropionamide LC/MS (m/z) 357.0 ([M+H]$^+$); RT=3.34, (UV, ELSD) 96.4%, 99.5%.

6q N-{2-Chloro-4-[(5-chloro-thiophen-2-ylmethyl)-amino]-phenyl}-2-phenoxyacetamide LC/MS (m/z) 406.9 ([M+H]$^+$); RT=3.54, (UV, ELSD) 93.9%, 100.0%.

6r N-{2-Chloro-4[(5-chloro-thiophen-2-ylmethyl)-amino]-phenyl}-2-phenylacetamide LC/MS (m/z) 391.1 ([M+H]$^+$); RT=3.29, (UV, ELSD) 98.0%, 100.0%.

6s N-{2-Chloro-4-[(5-chloro-thiophen-2-ylmethyl)-amino]-phenyl}-3,3-dimethylbutyramide LC/MS (m/z) 371.1 ([M+H]$^+$); RT=3.40, (UV, ELSD) 94.1%, 98.1%.

6t N-{2-Chloro-4-[(5-chloro-thiophen-2-ylmethyl)-amino]-phenyl}-butyramide

LC/MS (m/z) 343.0 ([M+H]$^+$); RT=3.01, (UV, ELSD) 77.8%, 88.9%.

6u Pentanoic acid {2-chloro-4-[(5-chloro-thiophen-2-ylmethyl)-amino]-phenyl}-amide LC/MS (m/z) 357.1 ([M+H]; RT=3.24, (UV, ELSD) 95.7%, 100.0%.

6v Cyclopropanecarboxylic acid {2-chloro-4-[(5-chloro-thiophen-2-ylmethyl)-amino]-phenyl}-amide LC/MS (m/z) 340.8 (M$^+$); RT 2.93, (UV, ELSD) 97.6%, 100.0%.

6w Cyclobutanecarboxylic acid {2-chloro-4-[(5-chloro-thiophen-2-ylmethyl)-amino]-phenyl}-amide LC/MS (m/z) 355.0 ([M+H]$^+$); RT=3.15, (UV, ELSD) 95.1%, 100.0%.

6x Cyclopentanecarboxylic acid {2-chloro-4-[(5-chloro-thiophen-2-ylmethyl)-amino]-phenyl}-amide LC/MS (m/z) 368.8 ([M+H]$^+$); RT=3.34, (UV, ELSD) 99.0%, 100.0%.

6y Cyclohexanecarboxylic acid {2-chloro-4-[(5-chloro-thiophen-2-ylmethyl)-amino]-phenyl}-amide LC/MS (m/z) 384.0 ([M+2]$^+$); RT=3.50, (UV, ELSD) 98.2%, 100.0%.

6z N-{2-Chloro-4-[(5-chloro-thiophen-2-ylmethyl)-amino]-phenyl}-2-thiophen-2-yl-acetamide LC/MS (m/z) 397.0 ([M+H]$^+$); RT=3.24, (UV, ELSD) 94.8%, 100.0%.

6aa N-{2-Chloro-4-[(5-chloro-thiophen-2-ylmethyl)-amino]-phenyl}-2-(3-methoxyphenyl)-acetamide LC/MS (m/z) 420.9 ([M+H]$^+$); RT=3.26, (UV, ELSD) 64.6%, 99.8%.

6ab N-{2-Chloro-4-[(5-chloro-thiophen-2-ylmethyl)-amino]-phenyl}-2-(4-chlorophenyl)-acetamide LC/MS (m/z) 425.0 ([M+H]$^+$); RT=3.50, (UV, ELSD) 98.9%, 100.0%.

6ac N-{2-Chloro-4-[(5-chloro-thiophen-2-ylmethyl)-amino]-phenyl}-2-(4 methoxyphenyl)-acetamide LC/MS (m/z) 421.2 ([M+H]$^+$); RT=3.24, (UV, ELSD) 95.3%, 99.6%.

6ad N-{2-Chloro-4-[(5-chloro-thiophen-2-ylmethyl)-amino]-phenyl}-2-(4-fluorophenyl)-acetamide LC/MS (m/z) 409.0 ([M+H]$^+$); RT=3.31, (UV, ELSD) 97.2%, 100.0%.

6ae, 2,3-Dihydro-benzo[1,4]dioxine-6-carboxylic acid {2-chloro-4-[(5-chloro-thiophen-2-ylmethyl)-amino]-phenyl}-amide LC/MS (m/z) 434.9 ([M+H]$^+$); RT=3.21, (UV, ELSD) 92.7%, 100.0%.

6af 2,3-Dihydro-benzofuran-5-carboxylic acid {2-chloro-4-[(5-chloro-thiophen-2-ylmethyl)-amino]-phenyl}-amide LC/MS (m/z) 419.3 ([M+H]$^+$); RT=3.26, (UV, ELSD) 81.6%, 94.8%.

6ag N-{2-Chloro-4-[(5-chloro-thiophen-2-ylmethyl)-amino]-phenyl}-3-cyclohexylpropionamide LC/MS (m/z) 411.1 ([M+H]$^+$); RT=3.89, (UV, ELSD) 95.3%, 99.5%.

6ah N-{4-[(5-Chloro-thiophen-2-ylmethyl)-(methyl)amino]-2-methyl-phenyl}-2,2-dimethylpropionamide LC/MS (m/z) 350.1 (M$^+$); RT=2.98, (UV, ELSD) 91.8%, 99.1%.

6ai N-{4-[(5-Chloro-thiophen-2-ylmethyl)-(methyl)amino]-2-methyl-phenyl}-2-phenylacetamide LC/MS (m/z) 384.1 (M$^+$); RT=3.04, (UV, ELSD) 95.8%, 100.0%.

6aj N-{4-[(5-Chloro-thiophen-2-ylmethyl)-(methyl)amino]-2-methyl-phenyl}-3,3-dimethylbutyramide LC/MS (m/z) 364.1 (M$^+$); RT=3.10, (UV, ELSD) 93.0%, 99.7%.

6ak N-{4-[(5-Chloro-thiophen-2-ylmethyl)-methyl)amino]-2-methyl-phenyl}-3-phenylpropionamide LC/MS (m/z) 399.1 ([M+H]$^+$); RT=3.12, (UV, ELSD) 98.2%, 99.9%.

6al N-{4-[(5-Chloro-thiophen-2-ylmethyl)-(methyl)amino]-2-methyl-phenyl}-butyramide LC/MS (m/z) 337.3 ([M+H]$^+$); RT=2.68, (UV, ELSD) 92.5%, 99.7%.

6am 2,2,2-Trichloro-N-{4-[(5-chloro-thiophen-2-ylmethyl)-(methyl)amino]-2-methyl-phenyl}-acetamide LC/MS (m/z) 411.9 ([M+H]$^+$); RT=3.65, (UV, ELSD) 97.3%, 100.0%.

6an Cyclopropanecarboxylic acid {4-[(5-chloro-thiophen-2-ylmethyl)-(methyl)amino]-2-methyl-phenyl}-amide LC/MS (m/z) 335.1 ([M+H]$^+$); RT=2.58, (UV, ELSD) 86.4%, 97.8%.

6ao Cyclobutanecarboxylic acid {4-[(5-chloro-thiophen-2-ylmethyl)-(methyl)amino]-2-methylphenyl}-amide LC/MS (m/z) 348.0 (M$^+$); RT=2.79, (UV, ELSD) 95.4%, 100.0%.

6ap Cyclopentanecarboxylic acid {4-[(5-chloro-thiophen-2-ylmethyl)-(methyl)amino]-2-methylphenyl}-amide LC/MS (m/z) 363.2 ([M+H]$^+$); RT=2.99, UV, ELSD) 97.7%, 99.9%.

6aq Cyclohexanecarboxylic acid {4-[(5-chloro-thiophen-2-ylmethyl)-(methyl)amino]-2-methylphenyl}-amide LC/MS (m/z) 377.1 ([M+H]$^+$); RT=3.16, (UV, ELSD) 88.0%, 97.5%.

6ar N-{4-[(5-Chloro-thiophen-2-ylmethyl)-(methyl)amino]-2-methylphenyl}-2-thiophen-2-yl-acetamide LC/MS (m/z) 390.0 (M$^+$); RT=3.02, (UV, ELSD) 97.2%, 99.9%.

6as N-{4-[(5-Chloro-thiophen-2-ylmethyl)-(methyl)amino]-2-methylphenyl}-2-(3-methoxyphenyl)-acetamide LC/MS (m/z) 416.0 ([M+2]$^+$); RT=3.03, (UV, ELSD) 92.9%, 100.0%.

6at N-{4-[(5-Chloro-thiophen-2-ylmethyl)-(methyl)amino]-2-methylphenyl}-malonamic acid methyl ester LC/MS (m/z) 366.1 (M$^+$); RT=2.53, (UV, ELSD) 94.5%, 100.0%.

6au 2-(4-Chlorophenyl)-N-{4-[(5-chloro-thiophen-2-ylmethyl)-(methyl)amino]-2-methylphenyl}-acetamide LC/MS (m/z) 418.1 (M$^+$); RT=3.31, (UV, ELSD) 97.3%, 99.9%.

6av N-{4-[(5-Chloro-thiophen-2-ylmethyl)-(methyl)amino]-2-methylphenyl}-2-(4-methoxyphenyl)-acetamide LC/MS (m/z) 415.2 ([M+H]$^+$); RT=2.99, (UV, ELSD) 87.8%, 98.1%.

6aw N-{4-[(5-Chloro-thiophen-2-ylmethyl)-(methyl)amino]-2-methylphenyl}-2-(4-fluorophenyl)-acetamide LC/MS (m/z) 403.2 ([M+H]$^+$); RT=3.10, (UV, ELSD) 94.5%, 99.9%.

6ax N-{4-[(5-Chloro-thiophen-2-ylmethyl)-(methyl)amino]-2-methylphenyl}-3-cyclohexylpropionamide LC/MS (m/z) 405.1 ([M+H]$^+$); RT=3.61, (UV, ELSD) 92.6%, 98.9%.

6ba {2-Chloro-4-[(5-chloro-thiophen-2-ylmethyl)-(methyl)amino]-phenyl}-carbamic acid phenyl ester LC/MS (m/z) 406.2 (M$^+$); RT=3.78, (UV, ELSD) 96.3%, 99.4%.

6bb {2-Chloro-4-[(5-chloro-thiophen-2-ylmethyl)-(methyl)amino]-phenyl}-carbamic acid benzyl ester LC/MS (m/z) 422.1 ([M+2]$^+$); RT=3.91, (UV, ELSD) 92.7%, 99.3%.

6bc {2-Chloro-4-[(5-chloro-thiophen-2-ylmethyl)-(methyl)amino]-phenyl}-carbamic acid isobutyl ester LC/MS (m/z) 388.1 ([M+2]$^+$); RT=3.99, (UV, ELSD) 99.0%, 100.0%.

6bd {2-Chloro-4-[(5-chloro-thiophen-2-ylmethyl)-(methyl)amino]-phenyl}-carbamic acid butyl ester LC/MS (m/z) 386.0 (M$^+$); RT=4.03, (UV, ELSD) 97.1%, 99.9%.

6be {2-Chloro-4-[(5-chloro-thiophen-2-ylmethyl)-(methyl)amino]-phenyl}-carbamic acid hexyl ester LC/MS (m/z) 415.9 ([M+2]$^+$); RT=4.44, (UV, ELSD) 91.7%, 98.9%.

6bf {2-Chloro-4-[(5-chloro-thiophen-2-ylmethyl)-(methyl)amino]-phenyl}-carbamic acid 4-nitrobenzyl ester LC/MS (m/z) 465.0 (M$^+$); RT=3.80, (UV, ELSD) 91.7%, 97.9%.

6bg {2-Chloro-4-[(5-chloro-thiophen-2-ylmethyl)-(methyl)amino]-phenyl}-carbamic acid but-3-enyl ester LC/MS (m/z) 383.9 (M$^+$); RT=3.82, (UV, ELSD) 93.9%, 99.6%.

6bh {2-Chloro-4-[(5-chloro-thiophen-2-ylmethyl)-(methyl)amino]-phenyl}-carbamic acid but-2-ynyl ester LC/MS (m/z) 384.0 ([M+2]$^+$); RT=3.61, (UV, ELSD) 76.3%, 99.0%.

6bi {2-Chloro-4-[(5-chloro-thiophen-2-ylmethyl)-(methyl)amino]-phenyl}-carbamic acid 2,2-dimethylpropyl ester LC/MS (m/z) 399.9 (M$^+$); RT=4.11, (UV, ELSD) 98.8%, 99.6%.

6bj {2-Chloro-4-[(5-chloro-thiophen-2-ylmethyl)-(methyl)amino]-phenyl}-carbamic acid 2-chlorobenzyl ester LC/MS (m/z) 453.9 (M$^+$); RT=4.12, (UV, ELSD) 97.5%, 99.8%.

6bk {2-Chloro-4-[(5-chloro-thiophen-2-ylmethyl)-(methyl)amino]-phenyl}-carbamic acid 3-chloropropyl ester LC/MS (m/z) 407.9 ([M+2]$^+$); RT=3.72, (UV, ELSD) 88.7%, 97.5%.

6bl {2-Chloro-4-[(5-chloro-thiophen-2-ylmethyl)-(methyl)amino]-phenyl}-carbamic acid 2-benzyloxyethyl ester LC/MS (m/z) 464.0 (M$^+$); RT=3.86, (UV, ELSD) 89.1%, 98.7%.

6bm 3-{2-Chloro-4-[(5-chloro-thiophen-2-ylmethyl)-(methyl)amino]-phenyl}-1-methyl-1-propyl-urea LC/MS (m/z) 388.1 ([M+3]$^+$); RT=3.38, (UV, ELSD) 86.0%, 99.5%.

6bo 1-{2-Chloro-4-[(5-chloro-thiophen-2-ylmethyl)-(methyl)amino]-phenyl}-3-(2-fluorophenyl)-urea LC/MS (m/z) 425.0 ([M+2]$^+$); RT=3.65, (UV, ELSD) 94.9%, 99.9%.

Example 7

7a N-(4-{[5-(4-Chlorophenoxy)-1,3-dimethyl-1H-pyrazol-4-ylmethyl]-amino}-2-methylphenyl)-2,2-dimethylpropionamide A mixture of N-(4-Amino-2-methylphenyl)-2,2-dimethylpropionamide (300 mg, 1.45 mmol) and 5-(4-Chlorophenoxy)-1,3-dimethyl-1H-pyrazole-4-carbaldehyde (360 mg, 1.45 mmol) in acetonitrile (4 mL) was heated and stirred at 170° C. under microwave irradiation for 20 minutes. The obtained reaction mixture was added carefully into solution of sodium cyanoborohydride (0.36 g) in methanol followed by acetic acid (1 mL). After 60 minutes it was partitioned between ethyl acetate and saturated aqueous sodium bicarbonate solution and the organic layer was evaporated. The title compound was separated by flash chromatography on SiO$_2$ with gradient heptane-ethyl acetate and then precipitated from ethyl acetate with heptane. Yield 112 mg, 18%. LC/MS-TOF (m/z) 441; RT=2.34, (UV, ELSD) 98%, 100%. $^1$H NMR (DMSO-d$_6$): 1.18 (s, 9H), 1.96 (s, 3H), 2.15 (s, 3H), 3.47 (s, 3H), 3.75 (d, 2H), 5.4 (t, 1H, NH), 6.29 (dd, 1H), 6.33 (d, 1H), 6.24 (d, 1H), 6.99 (d, 2H), 7.41 (d, 2H), 8.58 (s, 1H, NH).

The following compounds were prepared analogously from corresponding anilines and aldehydes:

7b 2,2-Dimethyl-N-{2-methyl-4-[(6-phenoxypyridin-3-ylmethyl)-amino]-phenyl}-propionamide LC/MS-TOF (m/z) 390; RT=2.54, (UV, ELSD) 90%, 100%.

7c 2,2-Dimethyl-N-{2-methyl-4-[(3-methyl-5-phenylisoxazol-4-ylmethyl)-amino]-phenyl}-propionamide LC/MS-TOF (m/z) 378; RT=2.82, (UV, ELSD) 97%, 100%. $^1$H NMR (DMSO-d$_6$): 1.19 (s, 9H), 1.96 (s, 3H), 2.3 (s, 3H), 4.11 (d, 2H), 5.85 (t, 1H, NH), 6.42 (overlapping m, 2H), 6.79 (d, 1H), 7.55 (m, 3H), 7.72 (d, 2H), 8.61 (s, 1H, NH).

7d 2-(4-Fluorophenyl)-N-{2-methyl-4[(6-trifluoromethylpyridin-3-ylmethyl)-amino]-phenyl}-acetamide LC/MS-TOF (m/z) 418.4 ([M+H]$^+$); RT=2.75, (UV, ELSD) 99%, 100%. $^1$H NMR (DMSO-d$_6$): 1.98 (s, 3H), 3.54

(s, 2H), 4.39 (d, 2H), 6.28 (t, 1H, NH), 6.36 (dd, 1H), 6.43 (d, 1H), 6.91 (d, 1H), 7.14 (t, 2H), 7.35 (dd, 2H), 7.85 (d, 1H), 7.99 (dd, 1H), 8.74 (d, 1H), 9.21 (s, 1H, NH).

7e 3,3-Dimethyl-N-{2-methyl-4-[(6-trifluoromethylpyridin-3-ylmethyl)-amino]-phenyl}-butyramide LC/MS-TOF (m/z) 380.5 ([M+H]$^+$); RT=2.75, (UV, ELSD) 97%, 99%.

7f 2-(4-Fluorophenyl)-N-{2-methyl-4-[(6-p-tolyloxypyridin-3-ylmethyl)-amino]-phenyl}-acetamide LC/MS (m/z) 456.2 ([M+H]$^+$); RT=2.79, (UV, ELSD) 82.5%, 99.8%

7g 3,3-Dimethyl-N-{2-methyl-4-[(6-p-tolyloxypyridin-3-ylmethyl)-amino]-phenyl}-butyramide LC/MS (m/z) 418.3 ([M+H]$^+$); RT=2.75, (UV, ELSD) 62%, 93%

7h N-(4-{[6-(4-Cyanophenoxy)-pyrimidin-3-ylmethyl]-amino}-2-methylphenyl)-2-(4 fluorophenyl)-acetamide LC/MS (m/z) 467.2 ([M+H]$^+$); RT=2.65, (UV, ELSD) 72%, 96%

7i N-{4-[(6-Chloropyridin-3-ylmethyl)-amino]-2-methylphenyl}-2-(4-fluorophenyl)-acetamide LC/MS (m/z) 384.1 ([M+H]$^+$); RT=2.46, (UV, ELSD) 87%, 99%

7j 2-(4-Fluorophenyl)-N-{2-methyl-4-[(4-methyl-2-phenylpyrimidin-5-ylmethyl)-amino]-phenyl}-acetamide LC/MS (m/z) 441.4 ([M+H]$^+$); RT=2.97, (UV, ELSD) 90%, 100%

7k 3,3-Dimethyl-N-{2-methyl-4-[(2-phenylpyrimidin-5-ylmethyl)-amino]-phenyl}-butyramide LC/MS-TOF (m/z) 389.6 ([M+H]$^+$); RT=2.83, (UV, ELSD) 89%, 95%

Example 8

{4-[(5-Dimethylamino-3-methyl-benzo[b]thiophen-2-ylmethyl)-amino]-2-methylphenyl}-carbamic acid propyl ester A solution of (4-amino-2-methylphenyl)-carbamic acid propyl ester (21 mg, 0.10 mmol) and 5-dimethylamino-3-methyl-benzo[b]thiophene-2-carbaldehyde (26 mg, 0.12 mmol) in acetonitrile (0.5 mL) was heated at 170° C. for 2 minutes using a Personal Chemistry Smith Synthesizer microwave device. After cooling to room temperature, a solution of sodium cyanoborohydride (25 mg, 0.40 mmol) in methanol (0.1 mL) was added followed by acetic acid (50 µL), and the mixture was stirred for 30 minutes. It was partitioned between saturated aqueous sodium bicarbonate (10 mL) and ethyl acetate (10 mL), and the organic layer was dried over sodium sulfate and evaporated. Preparative LC-MS afforded the title compound (32 mg, 77% yield).

LC/MS-TOF (m/z) 412.4 ([M+H]$^+$); RT=2.02, (UV, ELSD) 81%, 97%.

The following compounds were prepared analogously from appropriate anilines and aldehydes:

8b [4-(3-Fluoro-4-trifluoromethyl-benzylamino)-2-methylphenyl]-carbamic acid ethyl ester LC/MS (m/z) 371.2 ([M+H]$^+$); RT=3.10, (UV, ELSD) 83%, 96%.

8c [4-(4-Chloro-benzylamino)-2-methylphenyl]-carbamic acid ethyl ester

LC/MS (m/z) 319.0 ([M+H]$^+$); RT=2.57, (UV, ELSD) 79%, 95%.

3d {4-[(6-Methoxy-benzo[b]thiophen-2-ylmethyl)-amino]-2-methylphenyl}-carbamic acid propyl ester LC/MS-TOF (m/z) 384.4 (M$^+$); RT=3.07, (UV, ELSD) 97%, 94%.

8e {4-[(7-Dimethylamino-benzo[b]thiophen-2-ylmethyl)-amino]-2-methylphenyl}-carbamic acid propyl ester LC/MS-TOF (m/z) 398.4 ([M+H]$^+$); RT=2.64, (UV, ELSD) 97%, 100%.

8f {4-[(6-Methoxy-benzo[b]thiophen-2-ylmethyl)-amino]-2-methylphenyl}-carbamic acid ethyl ester LC/MS-TOF (m/z) 370.4 (M$^+$); RT=2.79, (UV, ELSD) 98%, 99%.

8g 4[(3-Methyl-4-propoxycarbonylamino-phenylamino)-methyl]-benzoic acid methyl ester LC/MS (m/z) 356.1 (Ma); RT=2.52, (UV, ELSD) 80%, 100%.

Example 9

9a N-[2-Methyl-4-(4-trifluoromethyl-benzylamino)-phenyl]-butyramide

To a solution of (4-amino-3-methylphenyl)-(4-trifluoromethyl-benzyl)-carbamic acid tert-butyl ester (500 mg, 1.31 mmol) in dry tetrahydrofuran (10 mL) at 0° C. was added pyridine (159 mL, 1.97 mmol) followed by butyryl chloride (164 µL, 1.58 mmol) dropwise. After 5 minutes, the reaction mixture was allowed to warm to room temperature, and stirring was continued for 1 hour. The reaction mixture was then diluted with ethyl acetate, washed with 2 N HCl, saturated aqueous sodium bicarbonate twice, and brine, and was then dried over magnesium sulfate. Solvents were evaporated in vacuo and the residue was dissolved in a 1:1 mixture of dichloromethane and trifluoroacetic acid. After 30 minutes at room temperature the mixture was evaporated to dryness, the residue was dissolved in ethyl acetate (10 mL), the solution was washed twice with saturated aqueous sodium bicarbonate, twice with water, and was then dried over sodium sulfate. Evaporation of the solvents and recrystallization of the residue from ethyl acetate:heptane gave the title compound as a colorless solid (226 mg, 49%).

¹H NMR (DMSO-d₆): 0.90 (t, 3H), 1.58 (sextet, 2H), 2.01 (s, 3H), 2.19 (t, 2H), 4.35 (d, 2H), 6.24 (t, 1H), 6.32 (dd, 1H), 6.41 (d, 1H), 6.87 (d, 1H), 7.55 (d, 2H), 7.67 (d, 2H), 8.91 (s, 1H). LC/MS (m/z) 350.2 (M⁺); RT=2.77, (UV, ELSD) 95%, 100%.

The following compound was prepared analogously:

9b [2-Methyl-4-(4-trifluoromethyl-benzylamino)-phenyl]-carbamic acid ethyl ester Yield: 254 mg (55%).
LC/MS (m/z) 353.2 ([M+H]⁺); RT=2.93, (UV, ELSD) 97%, 100%.
¹H NMR (DMSO-d₆): 1.19 (br. s, 3H), 2.03 (s, 3H), 4.02 (q, 2H), 4.35 (s, 2H), 6.29 (br. s, 1H), 6.33 (dd, 1H), 6.41 (d, 1H), 6.86 (br. d, 1H), 7.55 (d, 2H), 7.67 (d, 2H), 8.39 (br. s, 1H).

Example 10

10a N-[2-Methyl-4-(4-trifluoromethyl-benzylamino)-phenyl]-2-piperidin-1-yl-acetamide To a solution of (4-amino-3-methylphenyl)-(4-trifluoromethyl-benzyl)-carbamic acid tert-butyl ester (15.2 mg, 40 mol) in DMF (100 μL) was added a solution of O-(7-azabenzotriazol-1-yl)-N,N,N',N'-tetramethyluronium hexafluorophosphate (HATU, 27.4 mg, 72 mol) in DMF (100 μL), followed by i-Pr₂NEt (25 μL, 144 mol) and piperidin-1-yl-acetic acid (8.6 mg, 60 mol). The resulting mixture was shaken at room temperature for 3 hours after which it was diluted with ethyl acetate (10 mL), washed with saturated aqueous ammonium chloride (2×10 mL), dried over sodium sulfate, and evaporated. The residue was purified on a FlashMaster system (silica, eluted with heptane/ethyl acetate mixtures) to yield [3-methyl-4-(2-piperidin-1-yl-acetylamino)-phenyl]-(4-trifluoromethylbenzyl)-carbamic acid tert-butyl ester as a white solid (10.7 mg, 53%). This was dissolved in dichloromethane (200 μL) and trifluoroacetic acid (200 μL), and the solution was kept at room temperature for 30 minutes, after which volatiles were evaporated and the residue was dried in vacuo at 0.1 mmHg and +40° C. for 1 hour. The resulting trifluoroacetic acid addition salt of the title compound was obtained as a yellow semisolid in quantitative yield.
LC/MS-TOF (m/z) 406.4 ([M+H]⁺); RT=2.02, (UV, ELSD) 99%, 98%.

The following compounds were prepared analogously from the appropriate anilines and carboxylic acids:

10b N-[2-Methyl-4-(4-trifluoromethyl-benzylamino)-phenyl]-2-pyrrolidin-1-yl-acetamide LC/MS-TOF (m/z) 392.3 ([M+H]⁺); RT=2.04, (UV, ELSD) 98%, 99%.

10c N-[2-Methyl-4-(4-trifluoromethyl-benzylamino)-phenyl]-2-morpholin-4-yl-acetamide LC/MS-TOF (m/z) 408.3 ([M+H]⁺); RT=1.98, (UV, ELSD) 99%, 100%.

10d (S)-2-Amino-4-methyl-pentanoic acid [2-methyl-4-(4-trifluoromethyl-benzylamino)-phenyl]-amide LC/MS-TOF (m/z) 394 ([M+H]⁺); RT=2.12, (UV, ELSD) 75%, 73%.

10e (R)-2-Amino-4-methyl-pentanoic acid [2-methyl-4-(4-trifluoromethyl-benzylamino)-phenyl]-amide LC/MS-TOF (m/z) 394 ([M+H]⁺); RT=2.29, (UV, ELSD) 89%, 100%.

10f 1-Amino-cyclopropanecarboxylic acid [2-methyl-4-(4-trifluoromethyl-benzylamino)-phenyl]-amide LC/MS-TOF (m/z) 365; RT=1.98, (UV, ELSD) 94%, 89%.

Example 11

Pentanoic acid {4-[(5-chloro-thiophen-2-ylmethyl)-(methyl)amino]-2-methylphenyl}-amide To a solution of N(4)-(5-Chloro-thiophen-2-ylmethyl)-2,N(4)-dimethyl-benzene-1,4-diamine (54 mg, 0.20 mmol) and triethylamine (84 μL, 0.60 mmol) in dry tetrahydrofuran (1 mL) was added pentanoyl chloride (36 μL, 0.30 mmol), and the mixture was stirred for 1 hour at room temperature after which it was partitioned between saturated aqueous sodium bicarbonate (5 mL) and ethyl acetate (5 mL). The organic layer was dried over sodium sulfate, volatiles were evaporated, and the residue was purified on a FlashMaster system (silica, eluted with heptane/ethyl acetate mixtures) to yield the title compound as a white solid (61 mg, 86%).
LC/MS (m/z) 351.3 ([M+H]⁺); RT=3.06, (UV, ELSD) 100%, 99%.

Example 12

12a {2-Benzyloxy-4-[(4-fluorobenzyl)-(methyl)amino]-phenyl}-thiocarbamic acid S-ethyl ester (3-Benzyloxy-4-nitrophenyl)(4-fluorobenzyl)methylamine (50 mg) was dissolved in tetrahydrofuran (2 mL). Acetic acid (0.1 mL) and zinc powder (200 mg) were added and the resulting mixture was sonicated for 1 hour. Additional zinc powder (100 mg) was added, and sonication was continued for 1 hour. The reaction mixture was filtered through silica (500 mg) and evaporated to dryness. 1,2-Dichloroethane (1 mL) was added, followed by diphosgene (0.03 mL). The reaction mixture was kept at room temperature for 15 minutes and then heated to 80° C. for 3 hours. After cooling to room temperature, triethylamine (0.12 mL) was added. An aliquot of the resulting mixture (one quarter) was mixed with thioethanol (0.026 mL), and the resulting mixture was shaken at room temperature over night. The mixture was evaporated to dryness, dissolved in dimethylsulfoxide (0.2 mL) and subjected to preparative LC-MS to yield 7.6 mg of the title compound. Yield: 52%.
LC-MS (m/z) 425.2 ([M+H]⁺); RT 3.35, (UV, ELSD) 95%, 99%.

The following compounds were prepared analogously from the appropriate nitro compounds and nucleophiles:

12b {2-Cyclopentyloxy-4-[(4-fluorobenzyl)-(methyl)amino]-phenyl}-thiocarbamic acid S-ethyl ester LC-MS (m/z) 403.1 ([M+H]⁺); RT=3.30, (UV, ELSD) 99%, 100%.

12c 1-{2-Cyclopentyloxy-4-[(4-fluorobenzyl)-(methyl)amino]-phenyl}-3-ethyl-urea Ethylamine was used instead of thioethanol LC-MS (m/z) 386.2 ([M+H]$^+$); RT=2.08, (UV, ELSD) 97%, 100%.

Example 13

13a N-{2-Chloro-4-[(5-chloro-thiophen-2-ylmethyl)-(methyl)amino]-phenyl}-2-(4-chlorophenyl)-acetamide 2-Chloro-N(4)-(5-chloro-thiophen-2-ylmethyl)-N(4)-methyl-benzene-1,4-diamine (100 mg) was added to a solution of 4-chlorophenylacetyl chloride (69 mg) in dry acetonitrile (2 mL) in a rubber-capped glass vial. The reaction mixture was heated in a microwave device to 150° C. for 15 minutes. The reaction mixture was poured into saturated aqueous sodium bicarbonate (5 mL) and extracted with ethyl acetate (5 mL). The organic phase was washed with water (5 mL) and brine (5 mL), dried over sodium sulfate, filtered, and evaporated to dryness. The crude product was purified by flash chromatography (heptane/ethyl acetate, gradient) to furnish 25.2 mg title compound. Yield: 16%.

LC-MS (m/z) 441.2 ([M+2]$^+$); RT=3.83, (UV, ELSD) 91%, 99%.

The following compound was prepared analogously (2-phenylpropionic acid chloride was prepared by heating 2-phenylpropionic acid in thionyl chloride and subsequent evaporation):

13b N-{2-Chloro-4-[(5-chloro-thiophen-2-ylmethyl)-(methyl)amino]-phenyl}-2-(4-chlorophenyl)-propionamide LC-MS (m/z) 453.0 (M$^+$); RT=4.01, (UV, ELSD) 91%, 99%.

Example 14

14a 4-[(5-Chloro-thiophen-2-ylmethyl)-amino]-2-iodophenyl)-carbamic acid ethyl ester (4-Amino-2-iodophenyl)-carbamic acid ethyl ester (2.3 g) and 5-chloro-thiophene-2-carbaldehyde (1.15 g) were dissolved in methanol (8 mL) and heated in a sealed glass tube for 3 minutes to 130° C. under microwave irradiation. After cooling to room temperature, a solution of sodium cyanoborohydride (4.7 g) in methanol (10 mL) was added, and the resulting mixture was again heated in a sealed glass tube for 5 minutes to 130° C. under microwave irradiation. After cooling to room temperature, the mixture was poured into water (50 mL) and extracted with ethyl acetate (50 mL). The aqueous phase was extracted with ethyl acetate (50 mL), and the combined organic phases were washed with water (2 times 80 mL) and brine (2 times 80 mL). The organic phase was dried over magnesium sulfate, filtered, and the solvent removed in vacuo. The resulting oil was purified by flash chromatography (silica gel, heptane/ethyl acetate gradient). The resulting product was lyophillised from dioxane/water to furnish the title compound (2 g, 63%) as orange solid.

$^1$H NMR (CDCl$_3$): 1.31 (t, 3H), 4.02 (b, 1H), 4.21 (q, 2H), 4.35 (d, 2H), 6.53 (b, 1H), 6.63 (dd, 1H), 6.75 (s, 2H), 7.06 (d, 1H), 7.63 (bs, 1H).

The following compound was prepared analogously:

14b N-{4-[(5-Chloro-thiophen-2-ylmethyl)-amino]-2-iodophenyl}-2-(4-fluorophenyl)-acetamide $^1$H NMR (CDCl$_3$): 3.72 (s, 2H), 4.01 (b, 1H), 4.35 (d, 2H), 6.62 (dd, 1H), 6.75 (s, 2H), 7.00 (d, 1H), 7.09-7.12 (m, 3H), 7.35 (dd, 2H), 7.85 (d, 1H).

Example 15

N-{5-[(5-Chloro-thiophen-2-ylmethyl)-amino]-4'-dimethylamino-biphenyl-2-yl}-2-(4-fluorophenyl)-acetamide {4-[(5-Chloro-thiophen-2-ylmethyl)-amino]-2-iodophenyl}-carbamic acid ethyl ester (270 mg), 4-dimethylaminophenylboronic acid (445 mg), and palladium(II) acetate (ca. 10 mg) were suspended in acetone (5 mL). Potassium carbonate (0.54 mL, 5M aqueous solution) was added, and the mixture was heated in a sealed glass tube in a microwave synthesizer for 10 minutes at 125° C. After cooling to room temperature, the organic phase was separated, evaporated on silica gel, and subjected three times to flash chromatography (heptane/ethyl acetate, gradient). The resulting solid was recrystallised three times from acetonitrile to furnish 38 mg of the title compound as a colorless solid. The combined mother liquors were evaporated on silica gel and subjected to flash chromatography. The resulting product was recrystallised from methanol to furnish a second crop (12 mg) which was combined with the first crop to yield a total of 50 mg (19%) of the title compound.

$^1$H NMR (DMSO-d$_6$): 2.91 (s, 6H), 3.44 (s, 2H), 4.39 (d, 2H), 6.32 (t, 1H), 6.51 (dd, 2H), 6.61 (d, 2H), 6.93 (dd, 2H), 7.02-7.04 (m, 3H), 7.07-7.10 (m, 2H), 7.22-7.23 (m, 2H), 9.01 (s, 1H).

LC-MS (m/z) 494.2 (M$^+$); RT=2.50, (UV, ELSD) 95%, 99%.

Example 16

16a {4-[(5-Chloro-thiophen-2-ylmethyl)-amino]-2-quinolin-3-yl-phenyl}-carbamic acid ethyl ester {4-[(5-Chloro-thiophen-2-ylmethyl)-amino]-2-iodophenyl}-carbamic acid ethyl ester (15 mg), 3-quinolineboronic acid (29.7 mg), palladium(II) acetate (ca. 1 mg), potassium carbonate (0.035 mL, 5M aqueous solution), and acetone (2 mL) were mixed and heated in heated in a sealed glass tube in a microwave synthesizer for 10 minutes at 125° C. After cooling to room temperature, the reaction mixture was extracted with ethyl acetate (4 mL), the organic phase washed with water (2×2 mL), and brine (2×2 mL), dried over magnesium sulfate, and filtered. The solvent was removed in vacuo, and the crude product was purified by preparative LC-MS. The collected fraction was evaporated in: vacuo, redissolved in ethyl acetate (5 mL), and the organic phase was washed with saturated aqueous sodium bicarbonate (3 mL), water (3 mL), and brine (2×2 mL). The organic phase was dried over magnesium sulfate, filtered, and the solvent was removed in vacuo to furnish the title compound (5 mg, 33%).

LC-MS (m/z) 438.0 ([M+H]$^+$); RT=2.32, (UV, ELSD) 89%, 100%.

The following compounds were prepared analogously:

16b {4-[(5-Chloro-thiophen-2-ylmethyl)-amino]-2-pyridin-3-yl-phenyl}-carbamic acid ethyl ester LC-MS (m/z) 388.2 ([M+H]$^+$); RT=2.01, (UV, ELSD) 97%, 100%.

16c {4-[(5-Chloro-thiophen-2-ylmethyl)-amino]-2-pyridin-4-yl-phenyl}-carbamic acid ethyl ester LC-MS (m/z) 388.1 ([M+H]$^+$); RT=1.95, (UV, ELSD) 98%, 100%.

16d {4-[(5-Chloro-thiophen-2-ylmethyl)-amino]-2-(6-methoxypyridin-3-yl)-phenyl}-carbamic acid ethyl ester LC-MS (m/z) 418.3 ([M+H]$^+$); RT=2.37, (UV, ELSD) 79%, 100%.

16e {4-[(5-Chloro-thiophen-2-ylmethyl)-amino]-2-quinolin-5-yl-phenyl}-carbamic acid ethyl ester LC-MS (m/z) 438.0 ([M+H]$^+$); RT=2.13, (UV, ELSD) 79%, 99%.

In Vitro and In Vivo Testing

The compounds of the invention have been tested and shown effect in one or more of the below models:

Relative Efflux Through the KCNQ2 Channel.

This exemplifies a KCNQ2 screening protocol for evaluating compounds of the present invention. The assay measures the relative efflux through the KCNQ2 channel, and was carried out according to a method described by Tang et al. (Tang, W. et. al., *J. Biomol. Screen.* 2001, 6, 325-331) for hERG potassium channels with the modifications described below.

An adequate number of CHO cells stably expressing voltage-gated KCNQ2 channels were plated at a density sufficient to yield a mono-confluent layer on the day of the experiment. Cells were seeded on the day before the experiment and loaded with 1 µCi/ml [$^{86}$Rb] over night. On the day of the experiment cells were washed with a HBSS-containing buffer. Cells were pre-incubated with drug for 30 minutes and the $^{86}$Rb$^+$ efflux was stimulated by a submaximal concentration of 15 mM KCl in the continued presence of drug for additional 30 minutes. After a suitable incubation period, the supernatant was removed and counted in a liquid scintillation counter (Tricarb). Cells were lysed with 2 mM NaOH and the amount of $^{86}$Rb+ was counted. The relative efflux was calculated $((CPM_{super}/(CPM_{super}+CPM_{cell}))_{Cmpd}/(CPM_{super}/(CPM_{super}+CPM_{cell}))_{15mM\,KCl})*100-100$.

The compounds of the invention have an EC$_{50}$ of less than 20000 nM, in most cases less than 200 nM and in many cases less than 200 nM. Accordingly, the compounds of the invention are considered to be useful in the treatment of diseases associated with the KCNQ family potassium channels.

Electrophysiological Patch-Clamp Recordings.

Voltage-activated KCNQ2 currents were recorded from mammalian CHO cells by use of conventional patch-clamp recordings techniques in the whole-cell patch-clamp configuration (Hamill O P et. al. *Pflügers Arch* 1981; 391: 85-100). CHO cells with stable expression of voltage-activated KCNQ2 channels were grown under normal cell culture conditions in CO$_2$ incubators and used for electrophysiological recordings 1-7 days after plating. KCNQ2 potassium channels were activated by voltage steps up to +80 mV in increments of 5-20 mV (or with a ramp protocol) from a membrane holding potential between −100 mV and −40 mV (Tatulian L et al. *J Neuroscience* 2001; 21 (15): 5535-5545). The electrophysiological effects induced by the compounds were evaluated on various parameters of the voltage-activated KCNQ2 current. Especially effects on the activation threshold for the current and on the maximum induced current were studied.

Some of the compounds of the invention have been tested in this test. A left-ward shift of the activation threshold or an increase in the maximum induced potassium current is expected to decrease the activity in neuronal networks and thus make the compounds useful in diseases with increased neuronal activity—like epilepsy.

Maximum Electroshock

The test was conducted in groups of male mice using corneal electrodes and administering a square wave current of 26 mA for 0.4 seconds in order to induce a convulsion characterised by a tonic hind limb extension (Wlaz et al. *Epilepsy Research* 1998, 30, 219-229).

Pilocarpine Induced Seizures

Pilocarpine induced seizures are induced by intraperitoneal injection of pilocarpine 250 mg/kg to groups of male mice and observing for seizure activity resulting in loss of posture within a period of 30 minutes (Starr et al. *Pharmacology Biochemistry and Behavior* 1993, 45, 321-325)

Electrical Seizure-Threshold Test

A modification of the up-and-down method (Kimball et a., *Radiation Research* 1957, 1-12) was used to determine the median threshold to induce tonic hind-limb extension in response to corneal electroshock in groups of male mice. The first mouse of each group received an electroshock at 14 mA, (0.4 s, 50 Hz) and was observed for seizure activity. If a seizure was observed the current was reduced by 1 mA for the next mouse, however, if no seizure was observed then the current was increased by 1 mA. This procedure was repeated for all 15 mice in the treatment group.

Chemical Seizure-Threshold Test

The threshold dose of pentylenetetrazole required to induce a clonic convulsion was measured by timed infusion of pentylenetetrazole (5 mg/ml at 0.5 ml/minute) into a lateral tail vein of groups of male mice (Nutt et al. *J Pharmacy and Pharmacology* 1986, 38, 697-698).

Amygdala Kindling

Rats underwent surgery to implantation of tri-polar electrodes into the dorsolateral amygdala. After surgery the animals were allowed to recover before the groups of rats received either varying doses of test compound or the drug's vehicle. The animals were stimulated with their initial after discharge threshold+25 µA daily for 3-5 weeks and on each occasion seizure severity, seizure duration, and duration of electrical after discharge were noted. (Racine. *Electroencephalography and Clinical Neurophysiology* 1972, 32, 281-294).

Side Effects

Central nervous system side effects were measured by measuring the time mice would remain on rotarod apparatus (Capacio et al. *Drug and Chemical Toxicology* 1992, 15, 177-201); or by measuring their locomotor activity by counting the number of infra-red beams crossed in a test cage ((Watson et al. *Neuropharmacology* 1997, 36, 1369-1375). Hypothermic actions on the animals core body temperature of the compound were measured by either rectal probe or implanted radiotelemetry transmitters capable of measuring temperature (Keeney et al. *Physiology and Behaviour* 2001, 74, 177-184.

Pharmacokinetics

The pharmacokinetic properties of the compounds were determined via. i.v. and p.o. dosing to Spraque Dawley rats, and, thereafter, drawing blood samples over 20 hours. Plasma concentrations were determined with LC/MS/MS.

The invention claimed is:
1. A substituted p-diaminobenzene derivative of the general formula I

$$\text{(I)}$$

wherein:
s is 0 or 1;
U is O, S, $SO_2$, $SONR^{11}$, or $CONR^{11}$; wherein:
  $R^{11}$ is hydrogen, $C_{1-6}$-alk(en/yn)yl, $C_{3-8}$-cycloalk(en)yl, or $C_{3-8}$-cycloalk(en)yl-$C_{1-6}$-alk(en/yn)yl; or
  $R^2$ and $R^{11}$ taken together with the nitrogen atom form a 5-8 membered saturated or unsaturated ring, which optionally contains 1, 2 or 3 further heteroatoms;
q is 0 or 1;
X is CO or $SO_2$; with the proviso that q is 0 when X is $SO_2$;
Z is O or S;
$R^1$ is hydrogen, $C_{1-6}$-alk(en/yn)yl, $C_{3-8}$-cycloalk(en)yl, $C_{3-8}$-cycloalk(en)yl-$C_{1-6}$-alk(en/yn)yl, acyl, hydroxy-$C_{1-6}$-alk(en/yn)yl, hydroxy-$C_{3-8}$-cycloalk(en)yl, hydroxy-$C_{3-8}$-cycloalk(en)yl-$C_{1-6}$-alk(en/yn)yl, halo-$C_{1-6}$-alk(en/yn)yl, halo-$C_{3-8}$-cycloalk(en)yl, halo-$C_{3-8}$-cycloalk(en)yl-$C_{1-6}$-alk(en/yn)yl, cyano-$C_{1-6}$-alk(en/yn)yl, cyano-$C_{3-8}$-cycloalk(en)yl or cyano-$C_{3-8}$-cycloalk(en)yl-$C_{1-6}$-alk(en/yn)yl;
$R^2$ is hydrogen, $C_{1-6}$-alk(en/yn)yl, $C_{3-8}$-cycloalk(en)yl, $C_{3-8}$-cycloalk(en)yl-$C_{1-6}$-alk(en/yn)yl, Ar, Ar—$C_{1-6}$-alk(en/yn)yl, Ar—$C_{3-8}$-cycloalk(en)yl, Ar—$C_{3-8}$-cycloalk(en)yl-$C_{1-6}$-alk(en/yn)yl, acyl, hydroxy-$C_{1-6}$-alk(en/yn)yl, hydroxy-$C_{3-8}$-cycloalk(en)yl, hydroxy-$C_{3-8}$-cycloalk(en)yl-$C_{1-6}$-alk(en/yn)yl, halogen, halo-$C_{1-6}$-alk(en/yn)yl, halo-$C_{3-8}$-cycloalk(en)yl, halo-$C_{3-8}$-cycloalk(en)yl-$C_{1-6}$-alk(en/yn)yl, cyano, cyano-$C_{1-6}$-alk(en/yn)yl, cyano-$C_{3-8}$-cycloalk(en)yl, cyano-$C_{3-8}$-cycloalk(en)yl-$C_{1-6}$-alk(en/yn)yl, $NR^{10}R^{10'}$—$C_{1-6}$-alk(en/yn)yl, $NR^{10}R^{10'}$—$C_{3-8}$-cycloalk(en)yl or $NR^{10}R^{10'}$—$C_{3-8}$-cycloalk(en)yl-$C_{1-6}$-alk(en/yn)yl;
wherein:
  $R^{10}$ and $R^{10'}$ are each independently hydrogen, $C_{1-6}$-alk(en/yn)yl, $C_{3-8}$-cycloalk(en)yl, $C_{3-8}$-cycloalk(en)yl-$C_{1-6}$-alk(en/yn)yl, hydroxy-$C_{1-6}$-alk(en/yn)yl, hydroxy-$C_{3-8}$-cycloalk(en)yl, hydroxy-$C_{3-8}$-cycloalk(en)yl-$C_{1-6}$-alk(en/yn)yl, halo-$C_{1-6}$-alk(en/yn)yl, halo-$C_{3-8}$-cycloalk(en)yl, halo-$C_{3-8}$-cycloalk(en)yl-$C_{1-6}$-alk(en/yn)yl, cyano-$C_{1-6}$-alk(en/yn)yl, cyano-$C_{3-8}$-cycloalk(en)yl or cyano-$C_{3-8}$-cycloalk(en)yl-$C_{1-6}$-alk(en/yn)yl; or
  $R^{10}$ and $R^{10'}$ taken together with the nitrogen atom form a 5-8 membered saturated or unsaturated ring, which optionally contains 1, 2 or 3 further heteroatoms; with the proviso that:

when $R^2$ is halogen or cyano, then s is 0; and
when s is 1 and $R^2$ is a hydrogen atom or acyl, then U is O or S;
$R^3$ is $C_{1-6}$-alk(en/yn)yl, $C_{3-8}$-cycloalk(en)yl, heterocycloalk(en)yl, $C_{3-8}$-cycloalk(en)yl-$C_{1-6}$-alk(en/yn)yl, $C_{1-6}$-alk(en/yn)yl-$C_{3-8}$-cycloalk(en)yl, $C_{1-6}$-alk(en/yn)yl-heterocycloalk(en)yl, heterocycloalk(en)yl-$C_{1-6}$-alk(en/yn)yl, $C_{1-6}$-alk(en/yn)yloxy-$C_{1-6}$-alk(en/yn)yl, $C_{3-8}$-cycloalk(en)yloxy-$C_{1-6}$-alk(en/yn)yl, $C_{1-6}$-alk(en/yn)yloxy-$C_{3-8}$-cycloalk(en)yl, $C_{1-6}$-alk(en/yn)yloxy-heterocycloalk(en)yl, $C_{1-6}$-alk(en/yn)yloxy-carbonyl-$C_{1-6}$-alk(en/yn)yl, $C_{3-8}$-cycloalk(en)yloxy-carbonyl-$C_{1-6}$-alk(en/yn)yl, $C_{3-8}$-cycloalk(en)yl-$C_{1-6}$-alk(en/yn)yloxy-carbonyl-$C_{1-6}$-alk(en/yn)yl, hydroxy-$C_{1-6}$-alk(en/yn)yl, hydroxy-$C_{3-8}$-cycloalk(en)yl, hydroxy-heterocycloalk(en)yl, hydroxy-$C_{3-8}$-cycloalk(en)yl-$C_{1-6}$-alk(en/yn)yl, hydroxy-$C_{1-6}$-alk(en/yn)yl-$C_{3-8}$-cycloalk(en)yl, hydroxy-$C_{1-6}$-alk(en/yn)yl-heterocycloalk(en)yl, halo-$C_{3-8}$-cycloalk(en)yl, halo-heterocycloalk(en)yl, halo-$C_{3-8}$-cycloalk(en)yl-$C_{1-6}$-alk(en/yn)yl, halo-$C_{1-6}$-alk(en/yn)yl-$C_{3-8}$-cycloalk(en)yl, halo-$C_{1-6}$-alk(en/yn)yl-heterocycloalk(en)yl, cyano-$C_{1-6}$-alk(en/yn)yl, cyano-$C_{3-8}$-cycloalk(en)yl, cyano-heterocycloalk(en)yl, cyano-$C_{3-8}$-cycloalk(en)yl-$C_{1-6}$-alk(en/yn)yl, cyano-$C_{1-6}$-alk(en/yn)yl-$C_{3-8}$-cycloalk(en)yl, cyano-$C_{1-6}$-alk(en/yn)yl-heterocycloalk(en)yl, acyl-$C_{1-6}$-alk(en/yn)yl, acyl-$C_{3-8}$-cycloalk(en)yl, acyl-heterocycloalk(en)yl, acyl-$C_{3-8}$-cycloalk(en)yl-$C_{1-6}$-alk(en/yn)yl, acyl-$C_{1-6}$-alk(en/yn)yl-$C_{3-8}$-cycloalk(en)yl, acyl-$C_{1-6}$-alk(en/yn)yl-heterocycloalk(en)yl, $NR^{12}R^{12'}$, optionally substituted $NR^{12}R^{12'}$-$C_{1-6}$-alk(en/yn)yl, optionally substituted $NR^{12}R^{12'}$-$C_{3-8}$-alk(en/yn)yl, or optionally substituted $NR^{12}R^{12'}$-$C_{3-8}$-alk(en/yn)yl-$C_{1-6}$-alk(en/yn)yl; wherein:
  $R^{12}$ and $R^{12'}$ are each independently hydrogen, $C_{1-6}$-alk(en/yn)yl, $C_{3-8}$-cycloalk(en)yl, $C_{3-8}$-cycloalk(en)yl-$C_{1-6}$-alk(en/yn)yl, Ar, Ar—$C_{1-6}$-alk(en/yn)yl, Ar—$C_{3-8}$-cycloalk(en)yl, Ar—$C_{3-8}$-cycloalk(en)yl-$C_{1-6}$-alk(en/yn)yl, Ar-heterocycloalk(en)yl, Ar-oxy-$C_{1-6}$-alk(en/yn)yl, Ar-oxy-$C_{3-8}$-cycloalk(en)yl, Ar-oxy-$C_{3-8}$-cycloalk(en)yl-$C_{1-6}$-alk(en/yn)yl, Ar-oxy-heterocycloalk(en)yl, hydroxy-$C_{1-6}$-alk(en/yn)yl, hydroxy-$C_{3-8}$-cycloalk(en)yl, hydroxy-$C_{3-8}$-cycloalk(en)yl-$C_{1-6}$-alk(en/yn)yl, halo-$C_{1-6}$-alk(en/yn)yl, halo-$C_{3-8}$-cycloalk(en)yl, halo-$C_{3-8}$-cycloalk(en)yl-$C_{1-6}$-alk(en/yn)yl, cyano-$C_{1-6}$-alk(en/yn)yl, cyano-$C_{3-8}$-cycloalk(en)yl, or cyano-$C_{3-8}$-cycloalk(en)yl-$C_{1-6}$-alk(en/yn)yl; or
  $R^{12}$ and $R^{12'}$ taken together with the nitrogen atom form a 5-8 membered saturated or unsaturated ring, which optionally contains 1, 2 or 3 further heteroatoms; with the proviso that when $R^3$ is $NR^{12}R^{12'}$ then q is 0; and
Y is a group of formula XXXXI:

$$\text{XXXXI}$$

wherein:
"|" represents a bond attaching the group represented by Y to the carbon atom;
V is C or CH; and
k is 0, 1, 2 or 3; and
each $R^5$ is independently $C_{1-6}$-alk(en/yn)yl, $C_{3-8}$-cycloalk(en)yl, $C_{3-8}$-cycloalk(en)yl-$C_{1-6}$-alk(en/yn)yl, Ar, Ar—$C_{1-6}$-alk(en/yn)yl, Ar—$C_{3-8}$-cycloalk(en)yl, Ar—$C_{3-8}$-cycloalk (en)yl-$C_{1-6}$-alk(en/yn)yl, Ar-oxy, Ar-oxy-$C_{1-6}$alk(en/yn)yl, Ar-oxy-$C_{3-8}$-cycloalk(en)yl, $C_{1-6}$-alk (en)yl -heterocycloalk(en)yl, Ar-oxy-$C_{3-8}$-cycloalk(en)yl-$C_{1-6}$-alk(en/yn)yl, acyl, $C_{1-6}$-alk (en/yn) yloxy, $C_{3-8}$-cycloalk(en)yloxy, $C_{3-8}$-cycloalk(en)yl-$C_{1-6}$-alk(en/yn)yloxy, $C_{1-6}$-alk(en/yn)yloxy-carbonyl, halogen, halo-$C_{1-6}$-alk(en/yn)yl, halo-$C_{3-8}$-cycloalk (en)yl, halo-$C_{3-8}$-cycloalk(en)yl-$C_{1-6}$-alk(en/yn)yl, —CO—$NR^6R^{6'}$, cyano, cyano-$C_{1-6}$-alk(en/yn)yl, cyano-$C_{3-8}$-cycloalk (en)yl, cyano-$C_{3-8}$-cycloalk(en)yl-$C_{1-6}$-alk(en/yn)yl, $NR^7R^{7'}$, S—$R^8$ or $SO_2R^8$; or two adjacent $R^5$ groups taken together with the aromatic group form a 5-8 membered ring, which optionally contains one or two heteroatoms; wherein:

$R^6$ and $R^{6'}$ are each independently hydrogen, $C_{1-6}$-alk(en/yn)yl, $C_{3-8}$-cycloalk(en)yl, $C_{3-8}$-cycloalk(en)yl-$C_{1-6}$-alk(en/yn)yl or Ar;

$R^7$ and $R^{7'}$ are each independently hydrogen, $C_{1-6}$-alk(en/yn)yl, $C_{3-8}$-cycloalk(en)yl, $C_{3-8}$-cycloalk(en)yl-$C_{1-6}$-alk(en/yn)yl, Ar, heterocycloalk(en)yl-$C_{1-6}$-alk(en/yn)yl, heterocycloalk(en)yl-$C_{3-8}$-cycloalk(en)yl, heterocycloalk(en)yl-$C_{3-8}$-cycloalk(en)yl-$C_{1-6}$-alk(en/yn)yl, heterocycloalk(en)yl-Ar or acyl; or $R^7$ and $R^{7'}$ taken together with the nitrogen atom form a 5-8 membered saturated or unsaturated ring which optionally contains 1, 2 or 3 further heteroatoms; and $R^8$ is hydrogen, $C_{1-6}$-alk(en/yn)yl, $C_{3-8}$-cycloalk(en)yl, $C_{3-8}$-cycloalk(en)yl-$C_{1-6}$-alk(en/yn)yl, Ar or —$NR^9R^{9'}$; wherein:

$R^9$ and $R^{9'}$ are each independently hydrogen, $C_{1-6}$-alk(en/yn)yl, $C_{3-8}$-cycloalk(en)yl or $C_{3-8}$-cycloalk(en)yl-$C_{1-6}$-alk(en/yn)yl;

or salts thereof.

2. The compound according to claim 1, wherein $R^1$ is $C_{1-6}$-alk(en/yn)yl or a hydrogen atom.

3. The compound according to claim 1, wherein s is 0.

4. The compound according to claim 1, wherein s is 1.

5. The compound according to claim 4, wherein U is an oxygen atom.

6. The compound according to claim 1, wherein $R^2$ is hydrogen, $C_{1-6}$-alk(en/yn)yl, $C_{3-8}$-cycloalk(en)yl, Ar, Ar—$C_{1-6}$-alk(en/yn)yl, halogen, halo-$C_{1-6}$-alk(en/yn)yl or cyano; with the provisos that when $R^2$ is halogen or cyano, then s is 0; and when s is 1 and $R^2$ is a hydrogen atom, then U is O or S.

7. The compound according to claim 1, wherein Z is an oxygen atom.

8. The compound according to claim 1, wherein Z is a sulfur atom.

9. The compound according to claim 1, wherein q is 0.

10. The compound according to claim 1, wherein q is 1.

11. The compound according to claim 1, wherein X is CO.

12. The compound according to claim 1, wherein $R^3$ is $C_{1-6}$-alk(en/yn)yl, $C_{3-8}$-cycloalk(en)yl, $C_{3-8}$-cycloalk(en)yl-$C_{1-6}$-alk(en/yn)yl, heterocycloalk (en)yl-$C_{1-6}$-alk(en/yn)yl, heterocycloalk(en)yl, Ar, Ar—$C_{1-6}$-alk(en/yn)yl, Ar-oxy-$C_{1-6}$-alk (en/yn)yl, Ar—$C_{1-6}$-alk(en/yn)yloxy-$C_{1-6}$-alk(en/yn)yl, $C_{1-6}$-alk(en/yn)yloxy-carbonyl-$C_{1-6}$-alk(en/yn)yl, halo-$C_{1-6}$-alk(en/yn)yl, $NR^{12}R^{12'}$, optionally substituted $NR^{12}R^{12'}$—$C_{1-6}$-alk(en/yn)yl, or optionally substituted $NR^{12}R^{12'}$—$C_{3-8}$-cycloalk(en)yl.

13. The compound according to claim 12, wherein $R^{12}$ and $R^{12'}$ are each independently hydrogen, $C_{1-6}$-alk(en/yn)yl or Ar.

14. The compound according to claim 1, wherein V is CH.

15. The compound according to claim 1, wherein each $R^5$ is independently $C_{1-6}$-alk(en/yn)yl, $C_{1-6}$-alk(en/yn)yl-heterocycloalk(en)yl, Ar, $C_{1-6}$-alk(en/yn)yloxy, Ar-oxy, $C_{1-6}$-alk(en/yn)yloxy-carbonyl, halogen, halo-$C_{1-6}$-alk(en/yn)yl, $NR^7R^{7'}$, S—$R^8$ or $SO_2R^8$; or two adjacent $R^5$ groups taken together with the aromatic group form a 5-8 membered ring, which optionally contains one or two heteroatoms.

16. The compound according to claim 15, wherein both $R^7$ and $R^{7'}$ are $C_{1-6}$-alk(en/yn)yl.

17. The compound according to claim 15, wherein $R^8$ is $C_{1-6}$-alk(en/yn)yl or Ar.

18. The compound according to claim 1, wherein the compound is:

2-(4-Fluorophenyl)-N-{2-methyl-4-[(6-p-tolyloxypyridin-3-ylmethyl)-amino]-phenyl}-acetamide;

2-(4-Fluorophenyl)-N-{2-methyl-4-[(6-trifluoromethylpyridin-3-ylmethyl)-amino]-phenyl}-acetamide;

3,3-Dimethyl-N-{2-methyl-4-[(6-p-tolyloxypyridin-3-ylmethyl)-amino]-phenyl }-butyramide;

3,3-Dimethyl-N-{2-methyl-4-[(6-trifluoromethylpyridin-3-ylmethyl)-amino]-phenyl}-butyramide;

N-(4-{[6-(4-Cyanophenoxy)-pyridin-3-ylmethyl]-amino}-2-methylphenyl)-2-(4-fluorophenyl) -acetamide;

N-{4-[(6-Chloropyridin-3-ylmethyl)-amino]-2-methylphenyl}-2-(4-fluorophenyl)-acetamide; or 2,2-Dimethyl-N-{2-methyl-4-[(6-phenoxypyridin-3-ylmethyl)-amino]-phenyl }-proprionamide;

or a salt thereof.

19. A pharmaceutical composition comprising one or more pharmaceutically acceptable carriers or diluents and a compound according to claim 1.

* * * * *